US010145852B2

(12) United States Patent
Smith et al.

(10) Patent No.: US 10,145,852 B2
(45) Date of Patent: *Dec. 4, 2018

(54) MULTIPLES MULTIPLEX IMMUNOHISTOCHEMICAL ASSAY USING PRIMARY ANTIBODIES OF THE SAME HOST SPECIES

(71) Applicant: Ventana Medical Systems, Inc., Tucson, AZ (US)

(72) Inventors: Jacquelyn Smith, Tucson, AZ (US); Harry James Hnatyszyn, Sunol, CA (US); Erik Olson, Tucson, AZ (US); Noah Theiss, Tucson, AZ (US); Alton Yates, Tucson, AZ (US); Eric Kaldjian, Ann Arbor, MI (US); Bharathi Vennapusa, Tucson, AZ (US)

(73) Assignee: VENTANA MEDICAL SYSTEMS, INC., Tucson, AZ (US)

(*) Notice: Subject to any disclaimer, the term of this patent is extended or adjusted under 35 U.S.C. 154(b) by 0 days.

This patent is subject to a terminal disclaimer.

(21) Appl. No.: 15/841,914

(22) Filed: Dec. 14, 2017

(65) Prior Publication Data
US 2018/0106816 A1 Apr. 19, 2018

Related U.S. Application Data

(63) Continuation of application No. 15/585,115, filed on May 2, 2017, now Pat. No. 9,874,571, which is a continuation of application No. 14/914,345, filed as application No. PCT/EP2014/067810 on Aug. 21, 2014, now Pat. No. 9,689,875.

(60) Provisional application No. 61/871,230, filed on Aug. 28, 2013.

(51) Int. Cl.
| | | |
|---|---|---|
| *G01N 31/00* | (2006.01) | |
| *G01N 33/53* | (2006.01) | |
| *G01N 33/574* | (2006.01) | |
| *G01N 33/68* | (2006.01) | |
| *G01N 1/30* | (2006.01) | |
| *G01N 1/31* | (2006.01) | |
| *G01N 33/543* | (2006.01) | |

(52) U.S. Cl.
CPC ......... *G01N 33/57492* (2013.01); *G01N 1/30* (2013.01); *G01N 1/312* (2013.01); *G01N 33/54306* (2013.01); *G01N 33/54393* (2013.01); *G01N 33/6872* (2013.01); *G01N 2001/302* (2013.01); *G01N 2333/7051* (2013.01); *G01N 2333/70535* (2013.01); *G01N 2333/70596* (2013.01)

(58) Field of Classification Search
None
See application file for complete search history.

(56) References Cited

U.S. PATENT DOCUMENTS 9,689,875 B2 * 6/2017 Smith .............. G01N 33/57492
9,874,571 B2 * 1/2018 Smith ............... G01N 33/6872
2012/0171668 A1 7/2012 May et al.

OTHER PUBLICATIONS

Bojarska-Junak et al., Natural killer-like T CD3+/CD16+CD56+ cells in chronic lymphocytic leukemia: Intracellular Cytokine Expression and Relationship with Clinical Outcome, Oncology Reports, 2010, pp. 803-810, vol. 24.
Carrega et al., Natural Killer Cells Infiltrating Human Nonsmall-Cell Lung Cancer Are Enriched in CD56BrightCD16- Cells and Display an Impaired Capability to Kill Tumor Cells, Cancer, 2008, pp. 863-875, vol. 112, No. 4.
De Blic et al., Rejection in Lung Transplantation—An Immunohistochemical Study of Transbronchial Biopsies, Transplantation, 1992, pp. 639-644, vol. 54, No. 4.
Dejarnette et al., Specific requirement for CD3ϵ in T cell development, Immunology, 1998, pp. 14909-14914, vol. 95.
Dietrich et al., Role of CD3γ in T Cell Receptor Assembly, The Journal of Cell Biology, 1996, pp. 299-310, vol. 132.
Galon et al., Type, Density, and Location of Immune Cells Within Human Colorectal Tumors Predict Clinical Outcome, Science, 2006, pp. 1960-1965, vol. 313.
Gerdes et al., GA201 (RG7160): A Novel, Humanized, Glycoengineered Anti- EGFR Antibody with Enhanced ADCC and Superior In Vivo Efficacy Compared with Cetuximab, Clinical Cancer Research, 2013, pp. 1126-1138, vol. 19, No. 5.
International Search Report dated Nov. 25, 2014 in corresponding PCT/EP2014/067810 filed Aug. 21, 2014.
Lanier et al., Functional Properties of a Unique Subset of Cytotoxic CD3+ T Lymphocytes that express Fc Receptors for IgG (CD16/LEU-11 Antigen), J. Exp. Med., 1985, pp. 2089-2106, vol. 162.
Nimmerjahn et al., Translating basic mechanisms of IgG effector activity into next generation cancer therapies, Cancer Immunity, 2012, pp. 13-19, vol. 12.
PCT Written Opinion dated Nov. 25, 2014 in corresponding PCT/EP2014/067810 filed Aug. 21, 2014.
Sconocchia et al., Tumor infiltration by FCyRIII (CD16)+ myeloid cells is associated with improved survival in patients with colorectal carcinoma, Int J Cancer, 2011, pp. 2663-2672, vol. 128 No. 11.
Searle et al., Phenotypic Analysis and Proliferative Responses of Human Endometrial Granulated Lyphocytes During the Menstrual Cycle, Biology of Reproduction, 1999, pp. 871-878, vol. 60.
Shibuya et al., Clinical Significance of Poor CD3 Response in Head and Neck Cancer, Clinical Cancer Research, Mar. 2002, pp. 745-751, vol. 8.

(Continued)

Primary Examiner — Lisa V Cook
(74) Attorney, Agent, or Firm — Ventana Medical Systems, Inc.

(57) ABSTRACT

Disclosed herein are methods and systems for detecting CD3 and CD16 in the same sample of a colorectal, head & neck, or lung tumor using immunohistochemical methods using primary antibodies from the same host species and secondary antibodies immunoreactive with antibodies of the host species of the primary antibodies. Methods to denature and block the first primary antibody contacted with the sample are provided.

25 Claims, 35 Drawing Sheets
(31 of 35 Drawing Sheet(s) Filed in Color)

(56) References Cited

OTHER PUBLICATIONS

Troy et al., CD1A Dendritic Cells Predominate in Transitional Cell Carcinom of Bladder and Kidney But are Minimally Activated, Journal of Urology, Jun. 1999, pp. 1962-1967, vol. 161, No. 6.
Turesson et al., Increased CD4+ T Cell Infiltrates in Rheumoid arthritis-Associated Interstitial Pneumonitis Compared with Idiopathic Interstitial Pneumonitis, Arthritis & Rheumatism, Jan. 2005, pp. 73-79, vol. 52, No. 1.

\* cited by examiner

FIG. 1A Head & Neck 91S-4130-E1 H&E
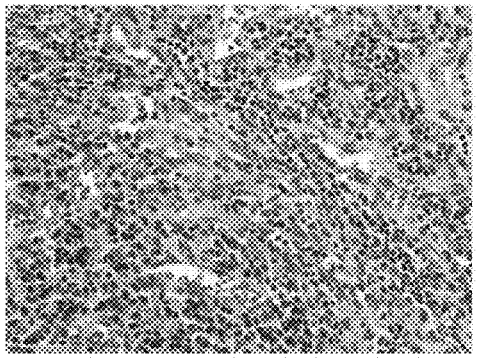
FIG. 1B Head & Neck 91S-4130-E1
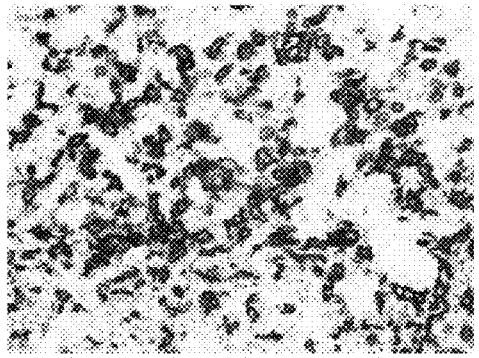
FIG. 1C Colorectal 5931 H&E
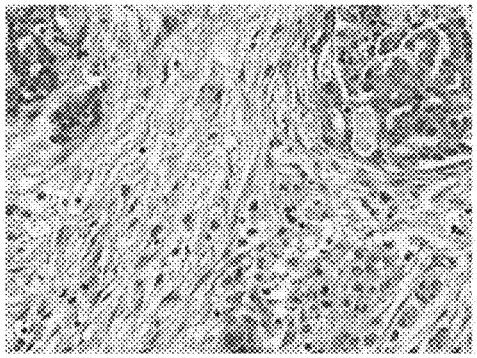
FIG. 1D Colorectal 5931
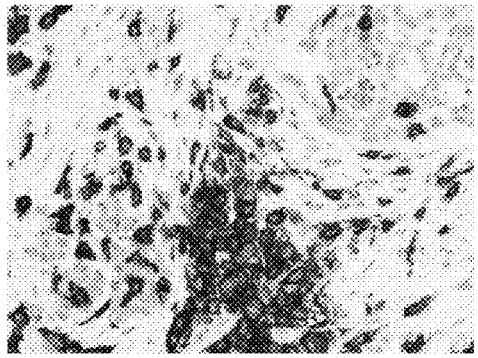
FIG. 1E NNSCLC 90S-3514-C4B H&E
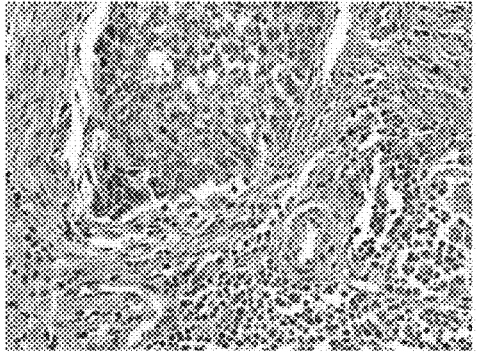
FIG. 1F NSCLC 90S-3514-C4B
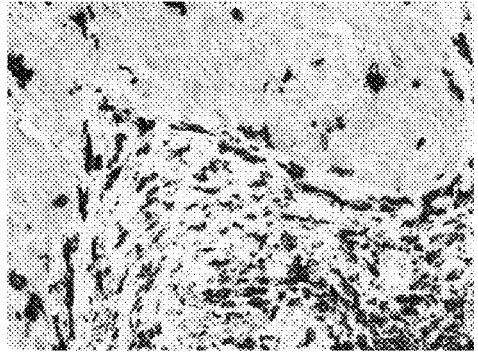

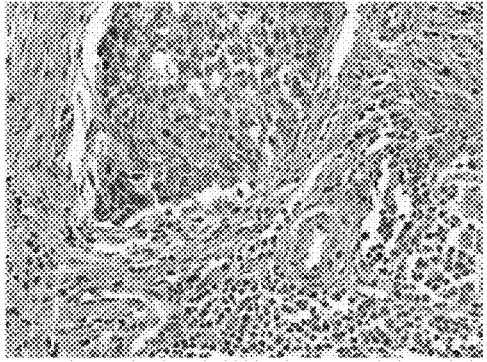
FIG. 2A H&E
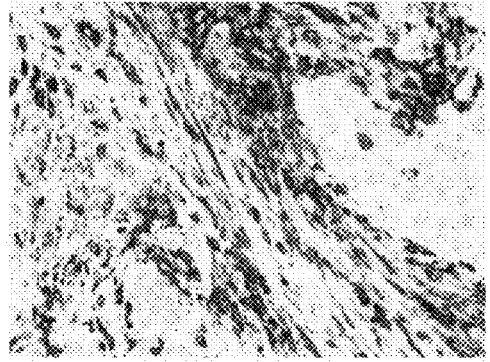
FIG. 2B 1:2000
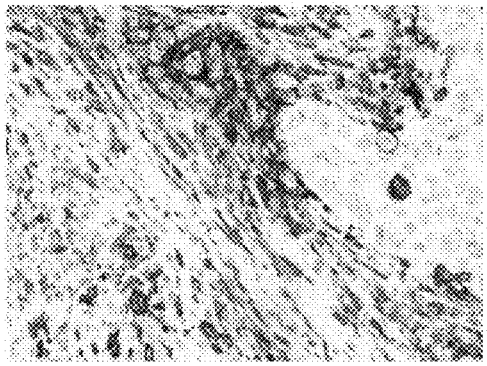
FIG. 2C 1:4000
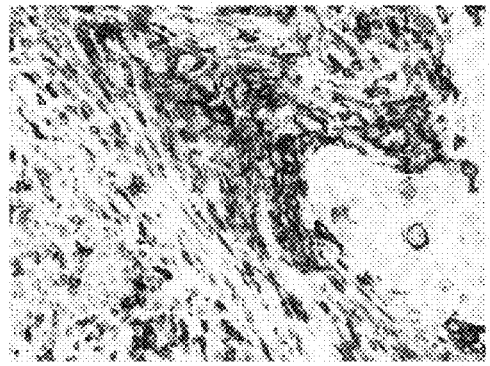
FIG. 2D 1:5000
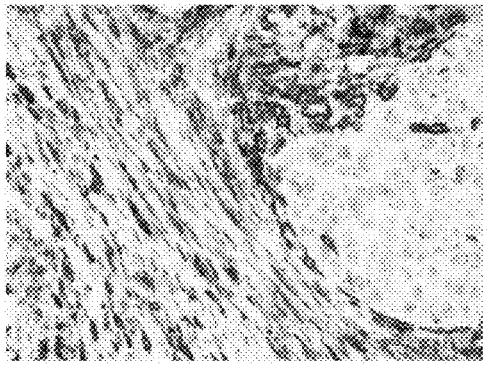
FIG. 2E 1:8000
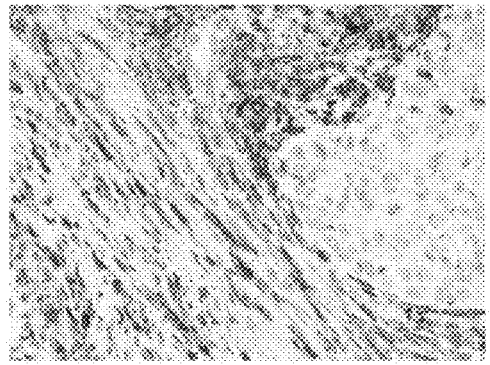
FIG. 2F 1:10000

FIG. 3A NSCLC 90S-3514-C4B H&E 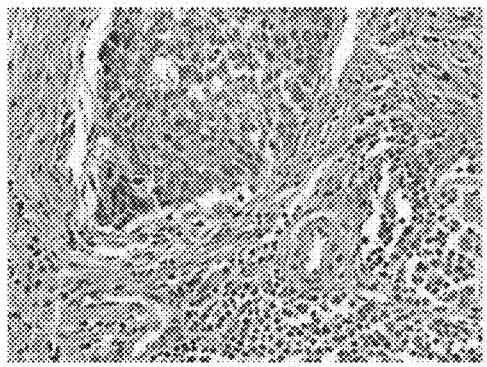

FIG. 4A Head & Neck 91S-4130-E1 H&E
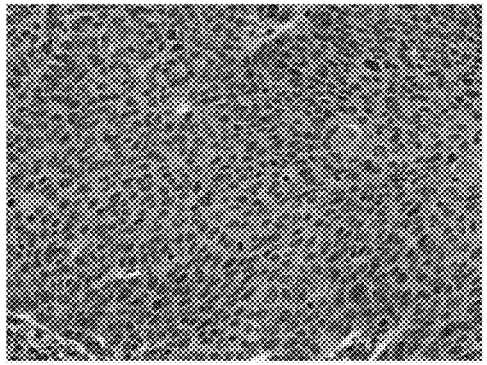
FIG. 4B Head & Neck 91S-4130-E1
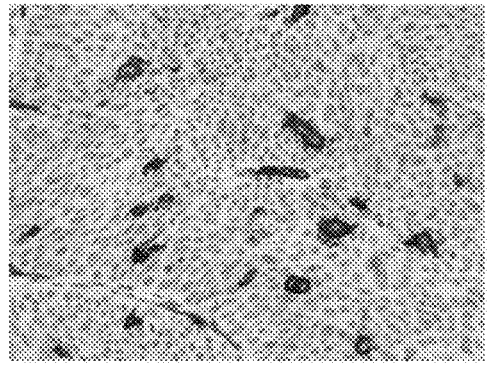
FIG. 4C Colorectal 5931 H&E
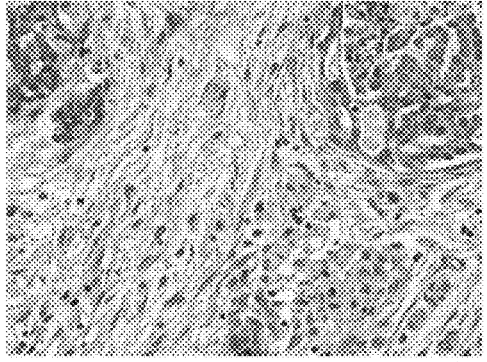
FIG. 4D Colorectal 5931
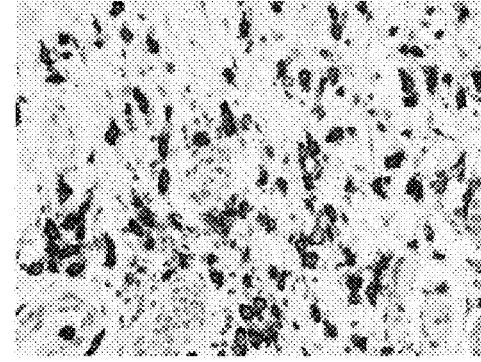
FIG. 4E NSCLC 90S-3514-C4B H&E
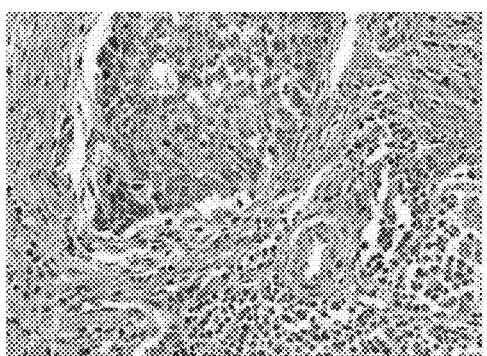
FIG. 4F NSCLC 90S-3514-C4B
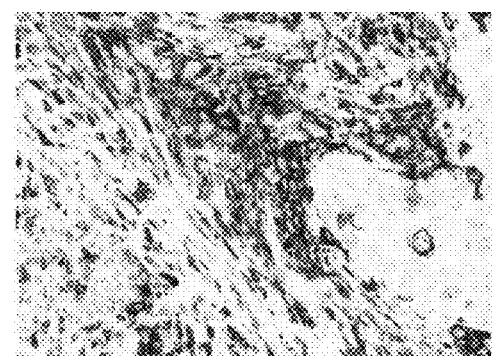

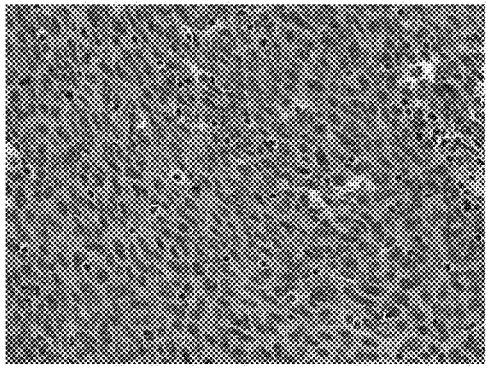
FIG. 5A Head & Neck 91S-4130-E1 H&E
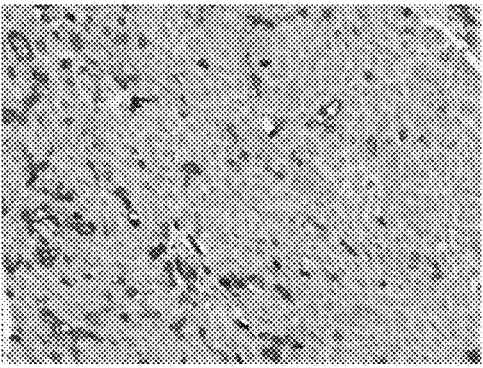
FIG. 5B Head & Neck 91S-4130-E1
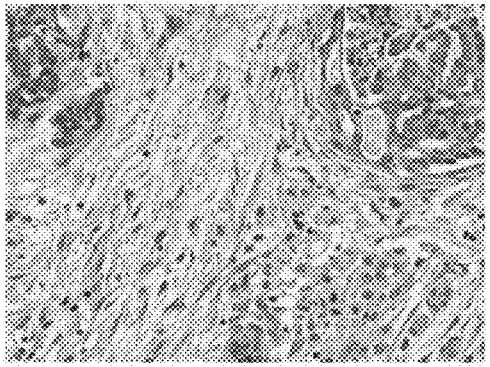
FIG. 5C Colorectal 5931 H&E
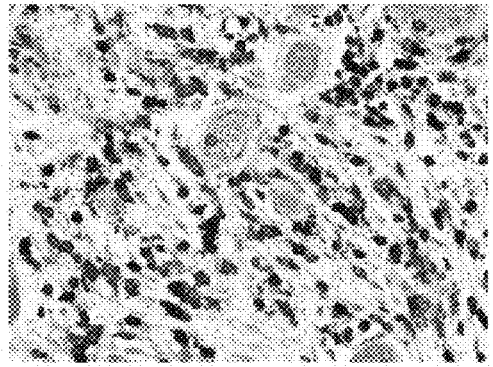
FIG. 5D Colorectal 5931
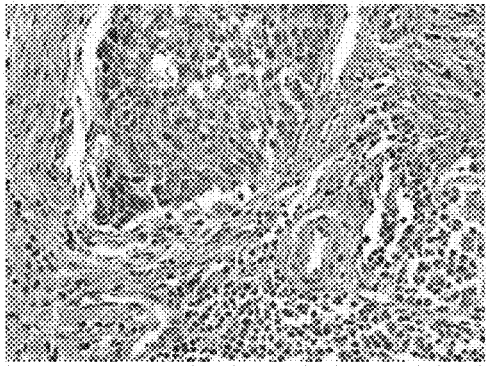
FIG. 5E NSCLC 90S-3514-C4B H&E
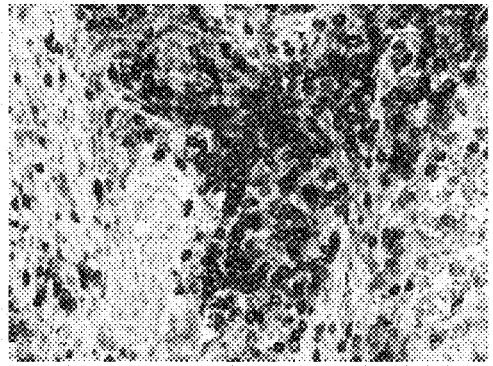
FIG. 5F NSCLC 90S-3514-C4B

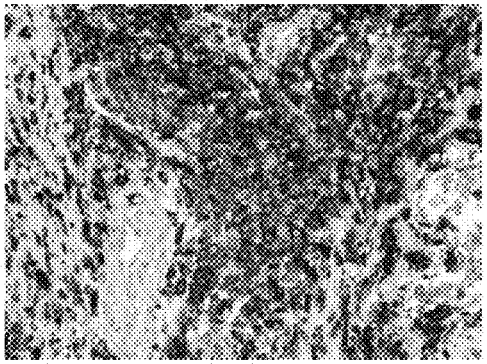
FIG. 6A 56 minutes
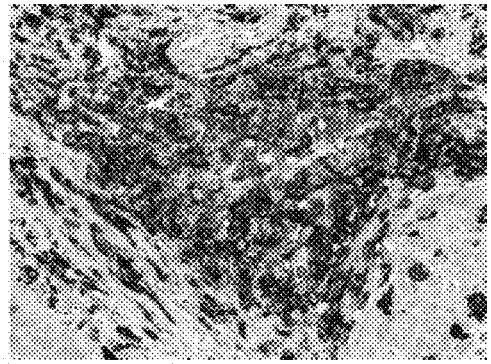
FIG. 6B 48 minutes
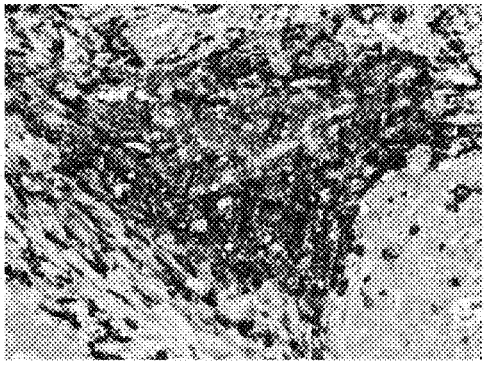
FIG. 6C 40 minutes
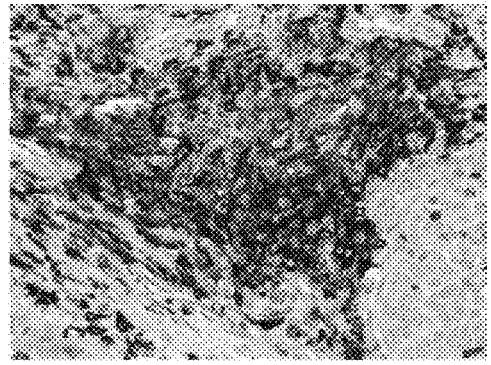
FIG. 6D 32 minutes FIG. 7A No CC
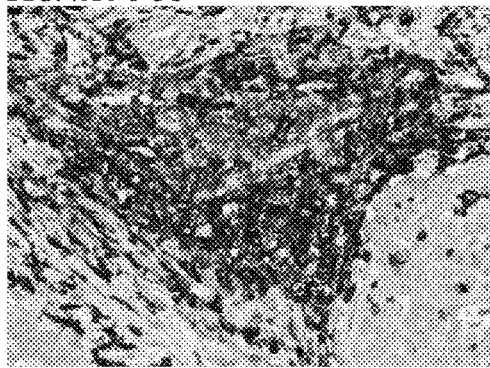
FIG. 7B 8 minutes
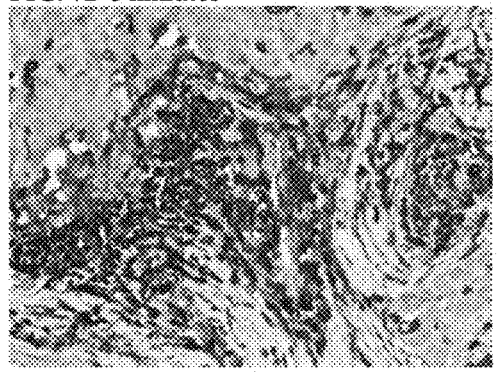
FIG. 7C 16 minutes
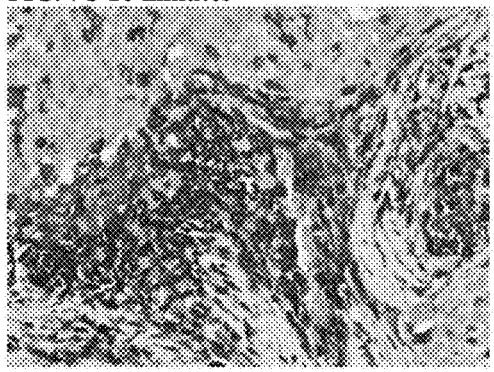

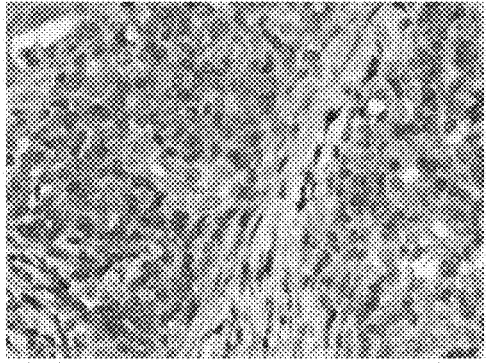
FIG. 8A 4 minutes
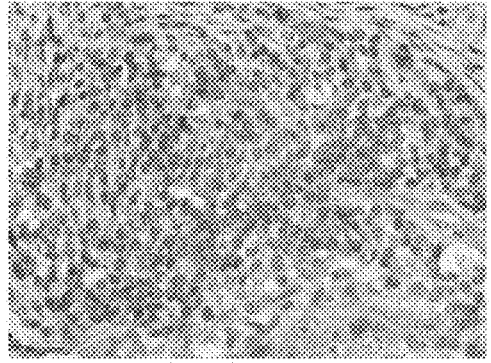
FIG. 8B 8 minutes
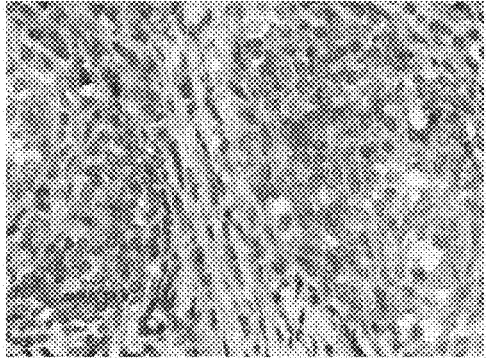
FIG. 8C 12 minutes

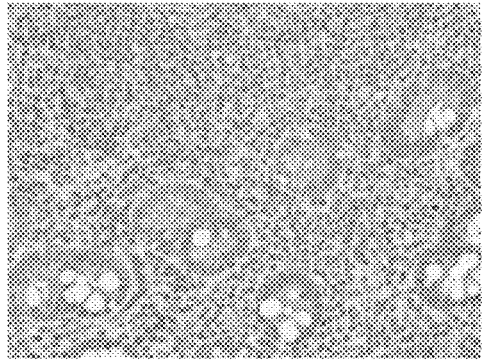
FIG. 9A 1:10
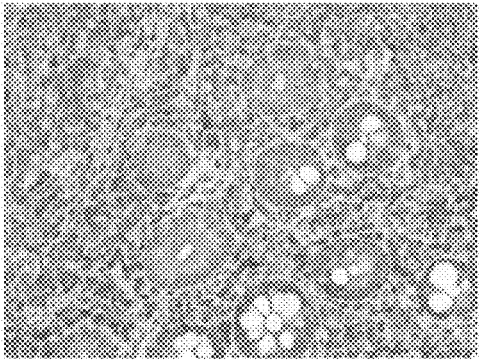
FIG. 9B 1:50
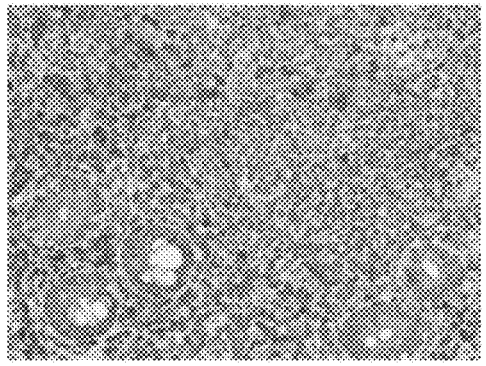
FIG. 9c 1:75
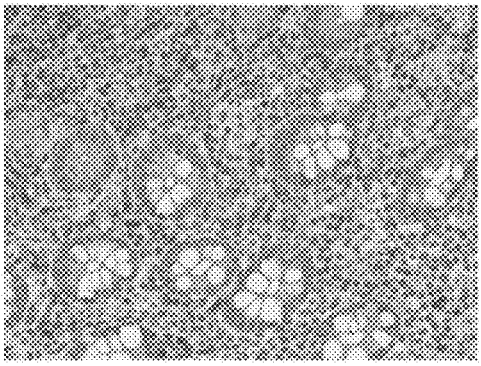
FIG. 9D 1:100

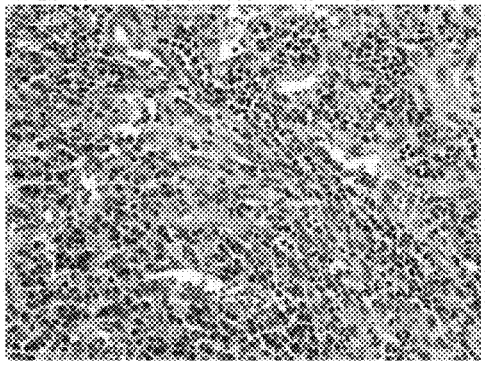
FIG. 10A Head & Neck 91S-4130-E1 H&E
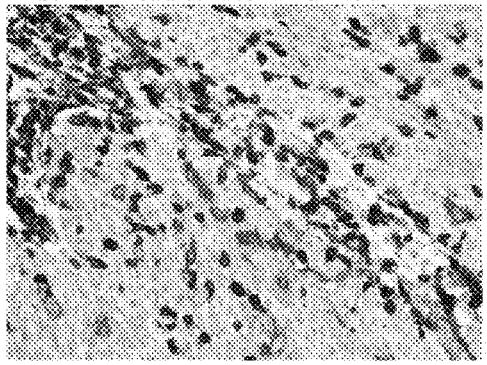
FIG. 10B Head & Neck 91S-4130-E1
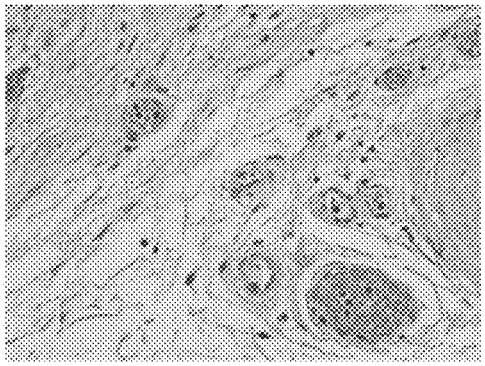
FIG. 10C Colorectal 5931 H&E
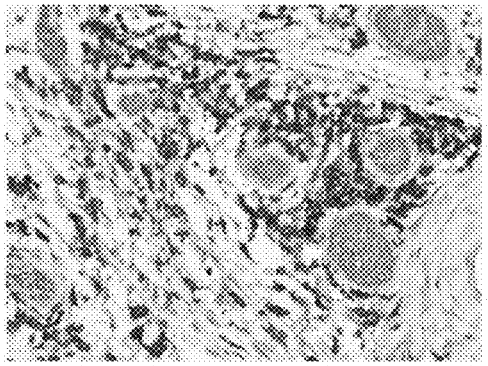
FIG. 10D Colorectal 5931
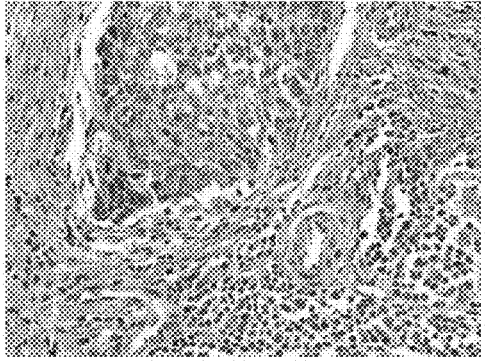
FIG. 10E NSCLC 90S-3514-C4B H&E
FIG. 10F NSCLC 90S-3514-C4B FIG. 11A Core 11 Tonsil H&E
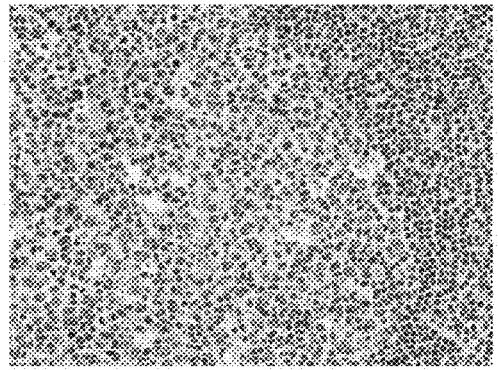
FIG. 11B Core 11 Tonsil(CD3 95, CD16 5)
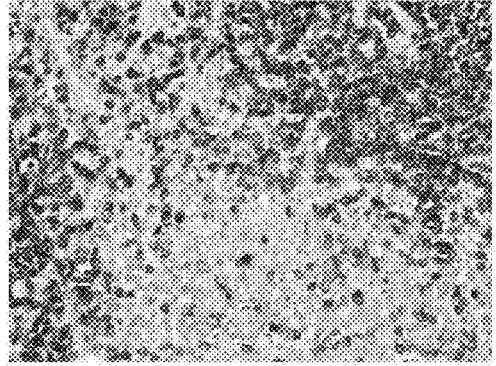
FIG. 11C Core 34 Breast Cancer H&E
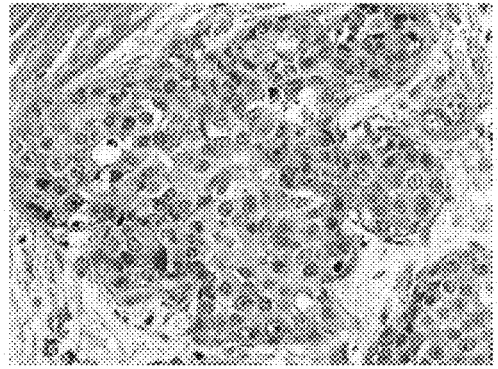
FIG. 11D Core 34 Breast Cancer(CD3 0, CD16 7)
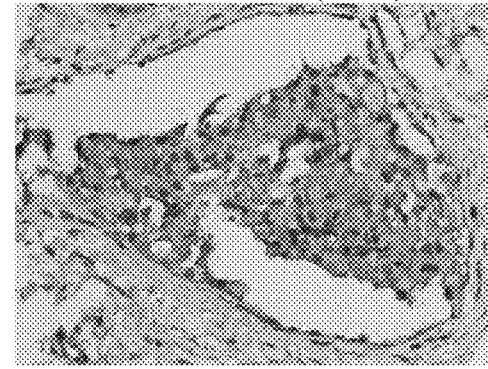
FIG. 11E Core 39 Lung Cancer H&E
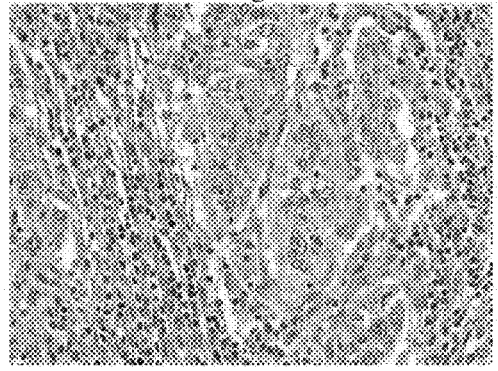
FIG. 11F Core 39 Lung Cancer (CD3 25, CD16 44)
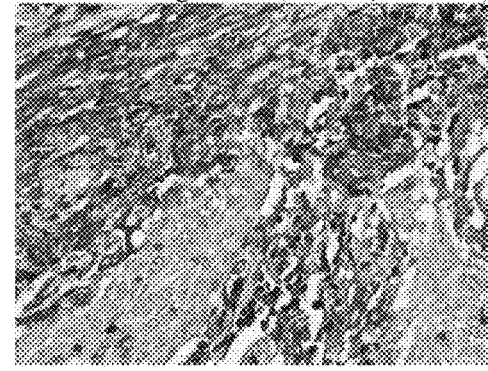

FIG. 12A Inter-Run Pathology Analysis of CD3
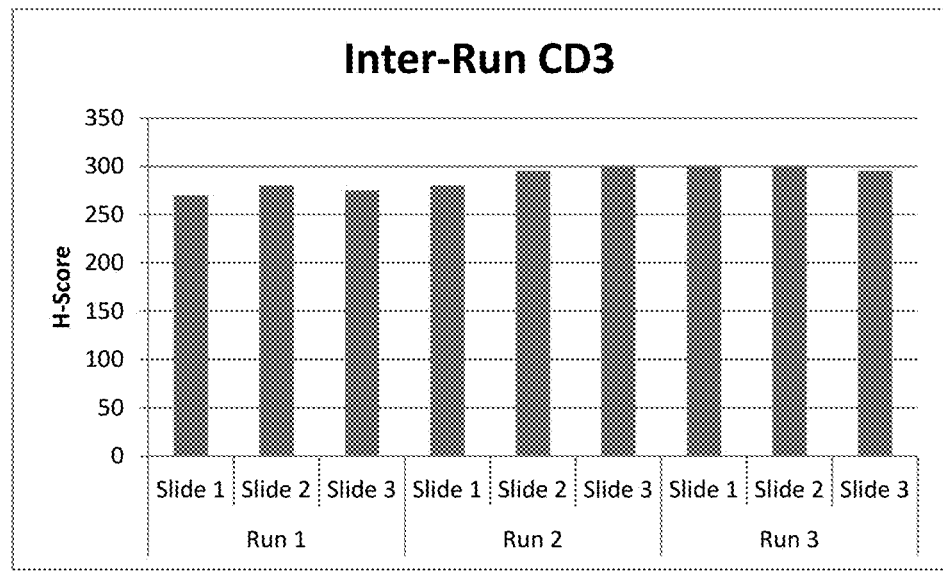
FIG. 12B Inter-Run Pathology Analysis of CD16
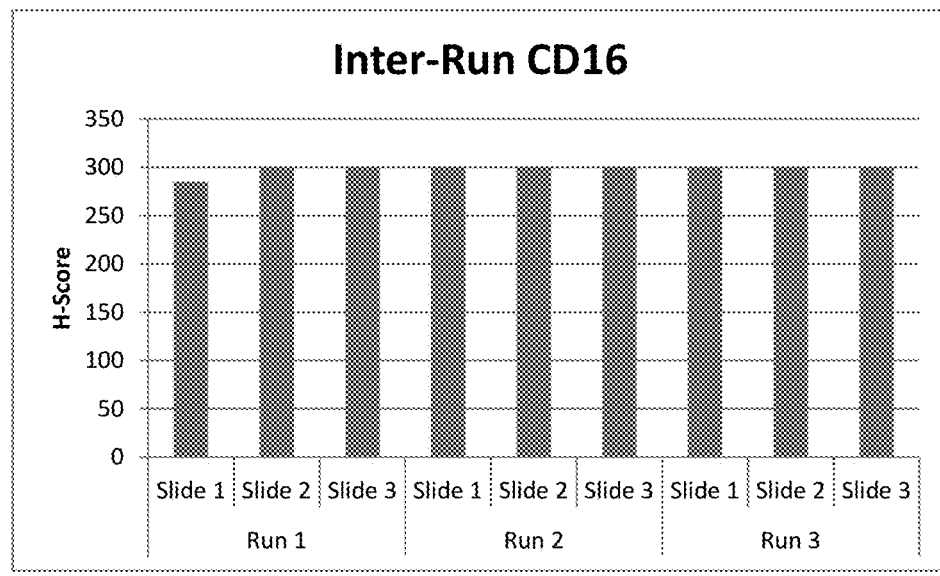

FIG. 12C  Inter-Instrument Pathology Analysis of CD3
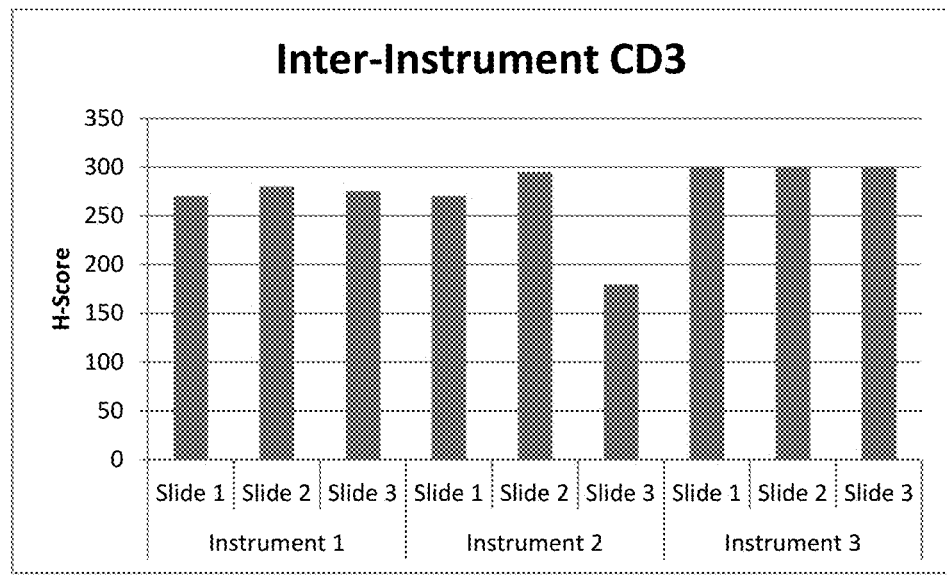
FIG. 12D  Inter-Instrument Pathology Analysis of CD16
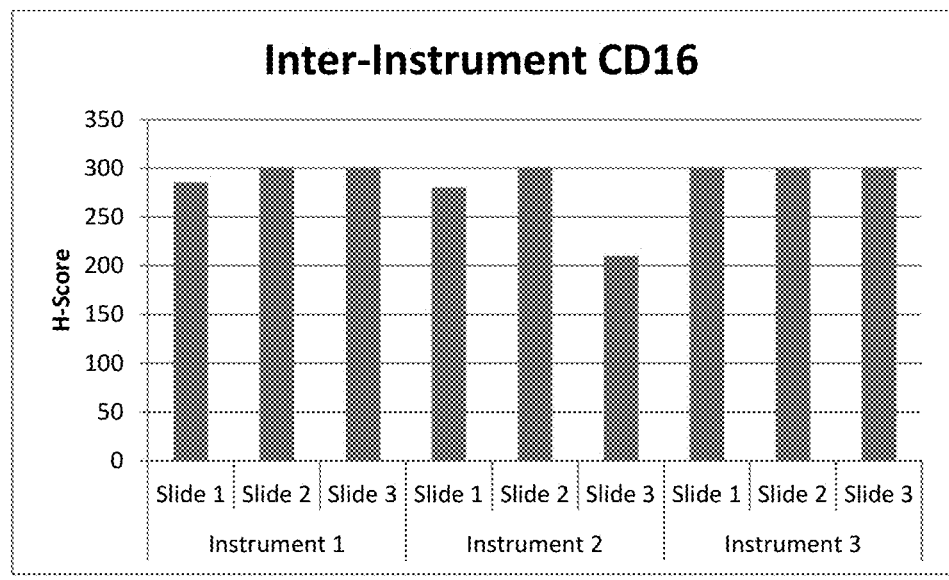

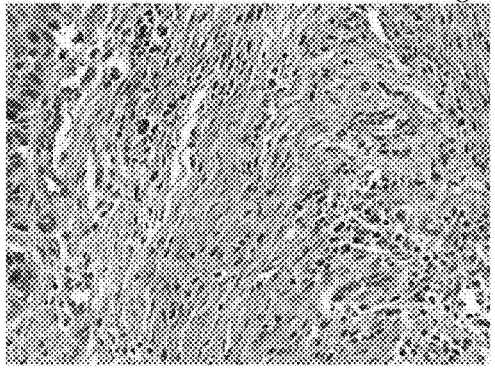
FIG. 13A 90S-3514-C4B Non-Small Cell Lung H&E
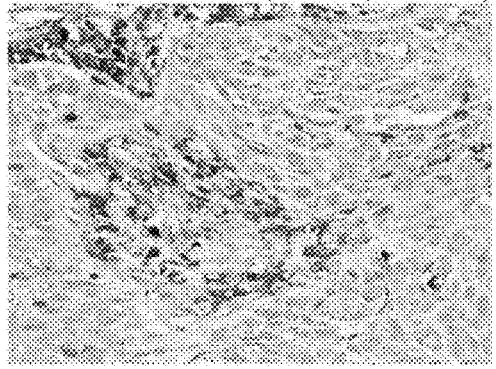
FIG. 13B Run 1 Slide 1 (CD3=270, CD16=285)
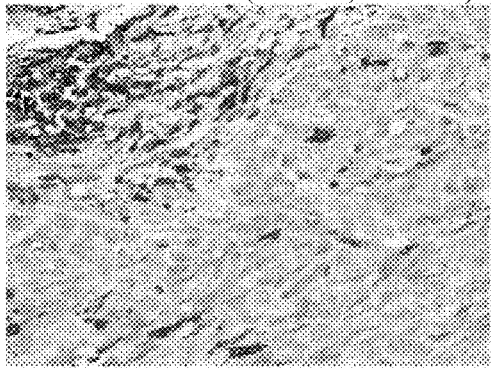
FIG. 13C Run 2 Slide 1 (CD3=280, CD16=300)
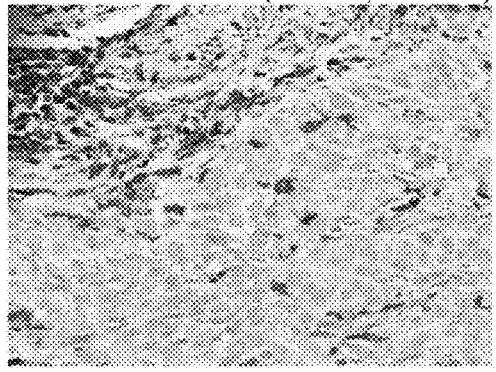
FIG. 13D Run 3 Slide 1 (CD3=275, CD16=300)
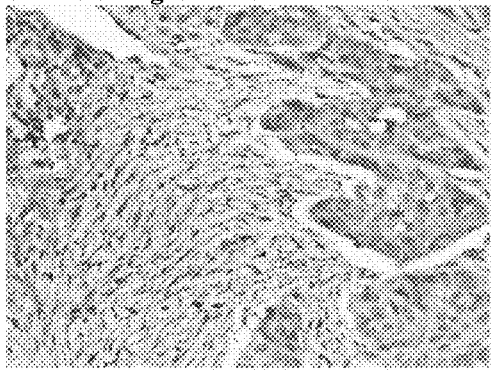
FIG. 13E Negative Control

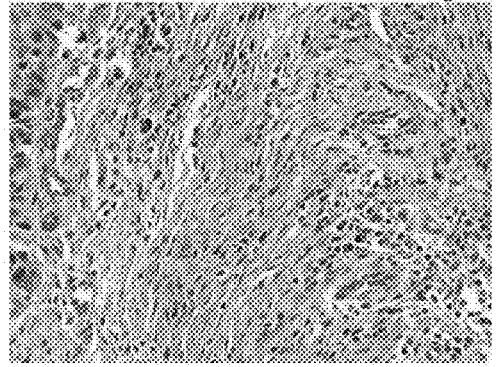
FIG. 14A 90S-3514-C4B Non-Small Cell Lung H&E
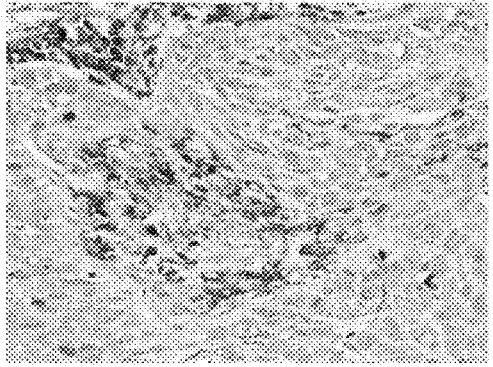
FIG. 14B Inst. 1, Slide 1 (CD3=270, CD16=285)
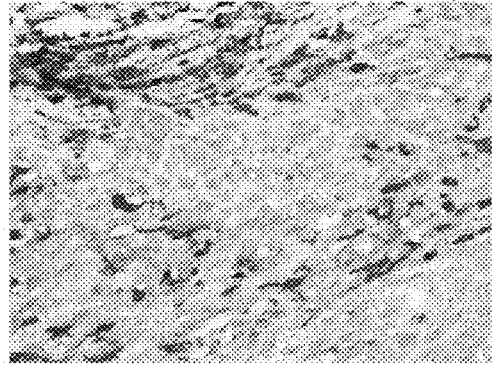
FIG. 14C Inst. 2, Slide 1 (CD3=270, CD16=280)
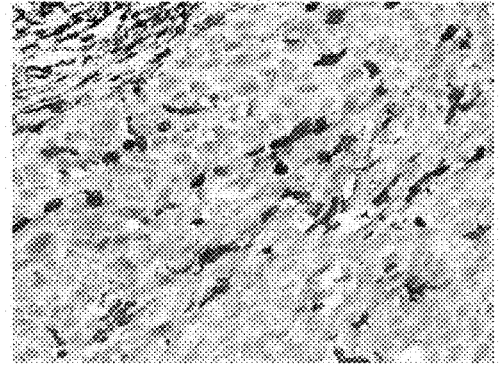
FIG. 14D Inst. 3, Slide 1 (CD3=300, CD16=300)
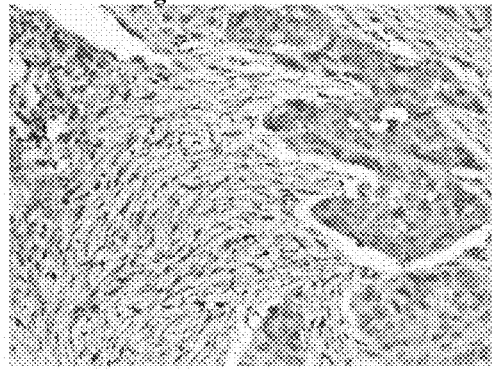
FIG. 14E Negative Control

FIG. 16A Core A08 H&E
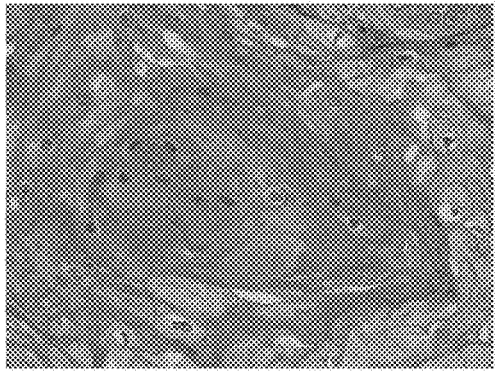
FIG. 16B Core A08 (CD3 0, CD16 0)
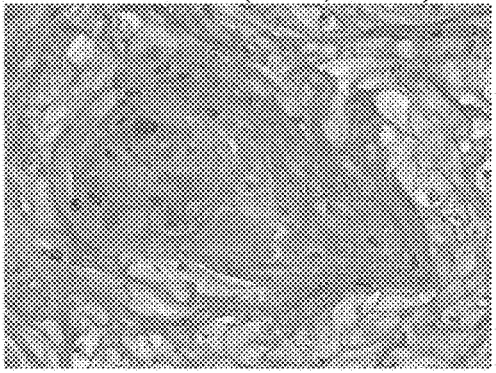
FIG. 16C Core C04 H&E
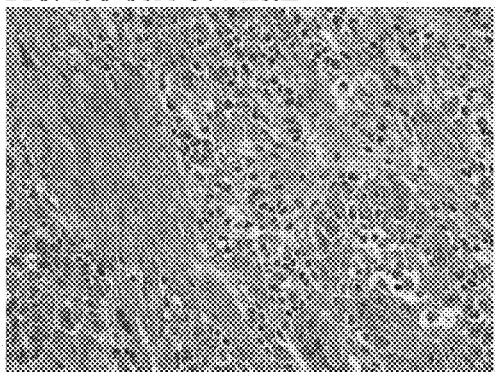
FIG. 16D Core C04 (CD3 66, CD16 68)
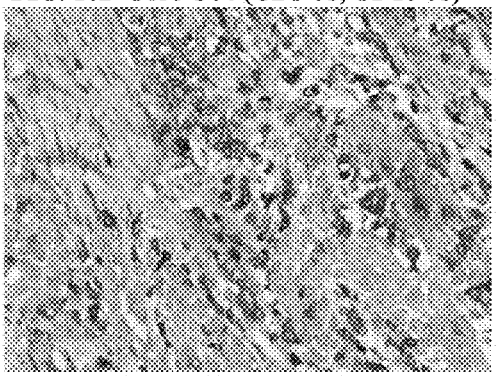
FIG. 16E Core H11 H&E
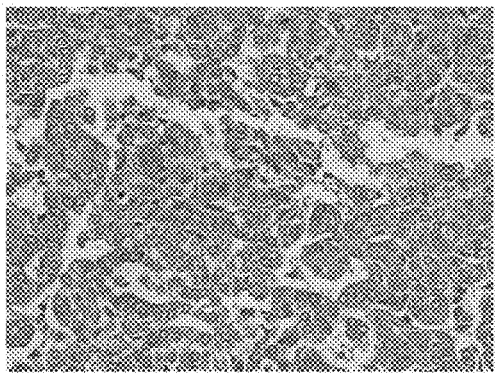
FIG. 16F Core H11 (CD3 4, CD16 63)
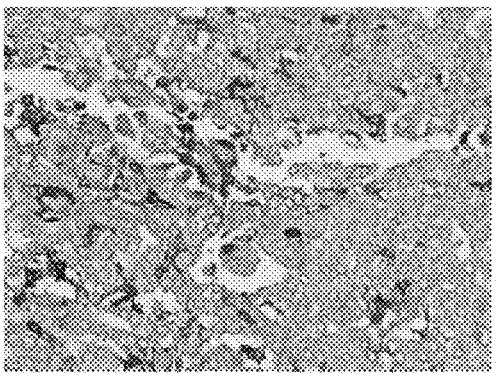

FIG. 18A Core A09 H&E
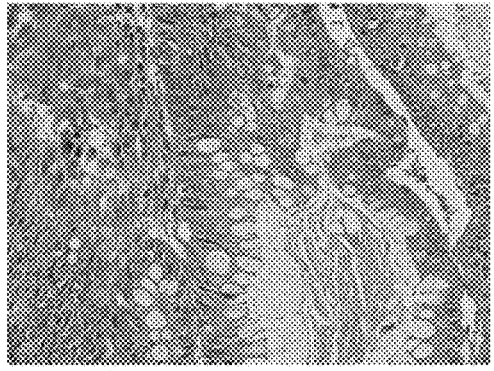
FIG. 18B Core A09 (CD3 42, CD16 13)
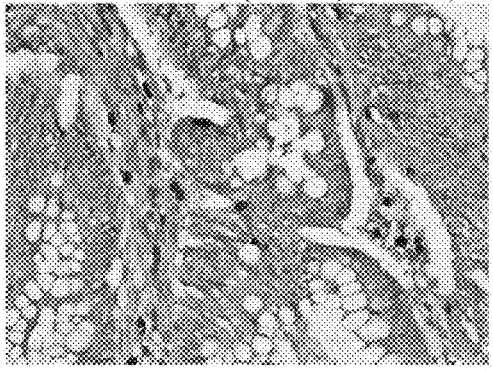
FIG. 18C Core D03 H&E
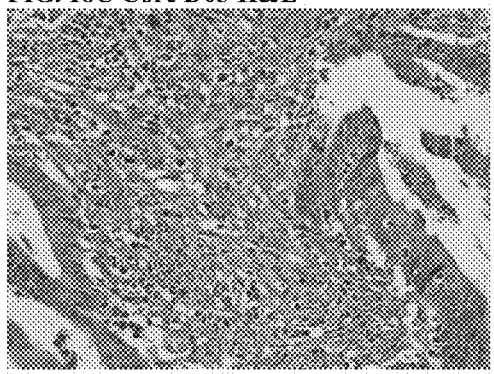
FIG. 18D Core D03 (CD3 53, CD16 52)
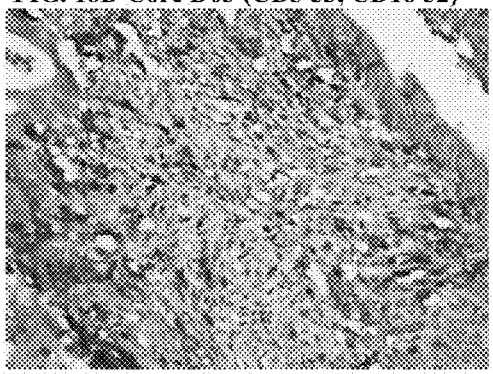
FIG. 18E Core G11 H&E
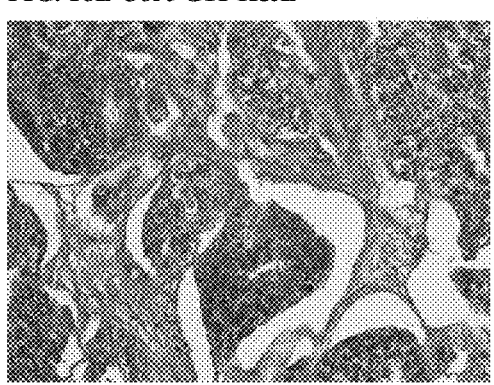
FIG. 18F Core G11 (CD3 0, CD16 0)
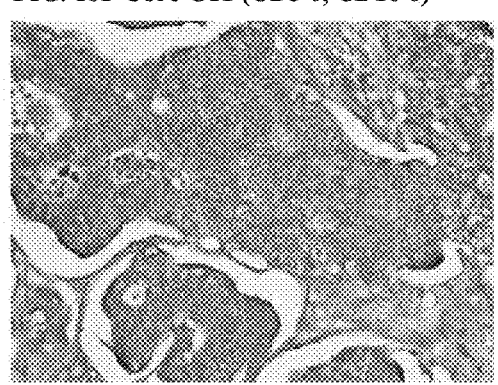

FIG. 20A Core C06 H&E
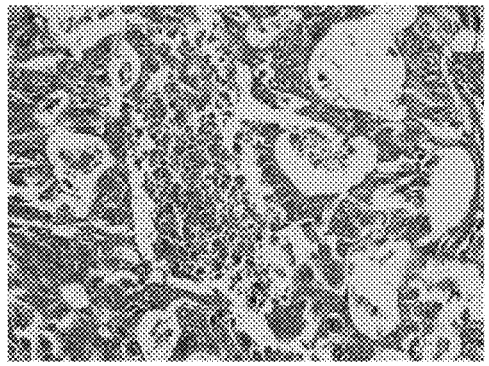
FIG. 20B Core C06 (CD3 0, CD16 0)
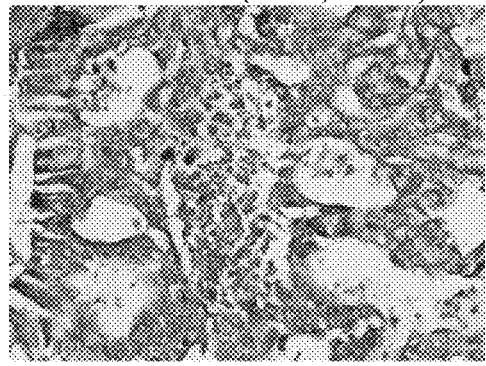
FIG. 20C Core E06 H&E
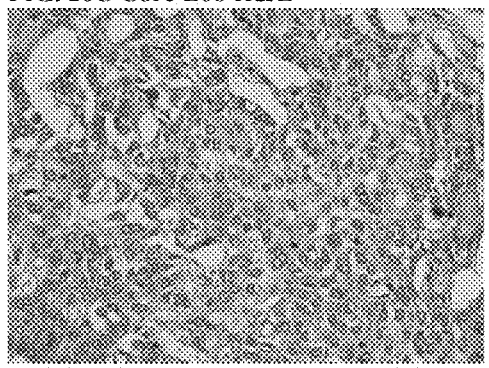
FIG. 20D Core E06 (CD3 26, CD16 28)
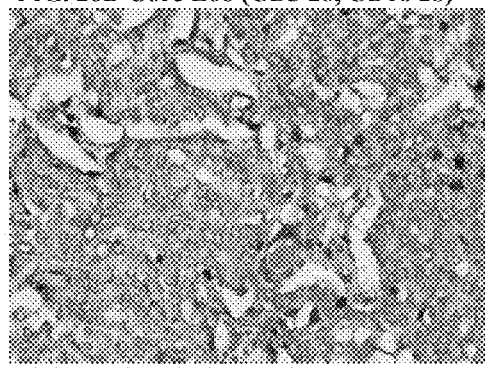
FIG. 20E Core F05 H&E
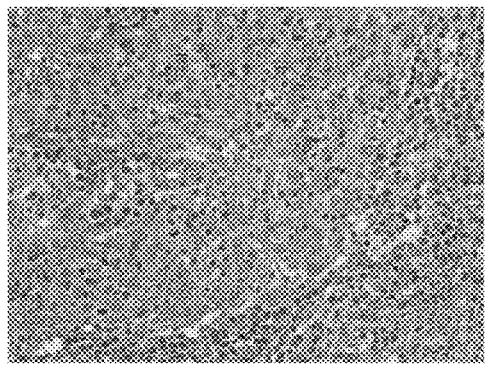
FIG. 20F Core F05 (CD3 160, CD16 51)
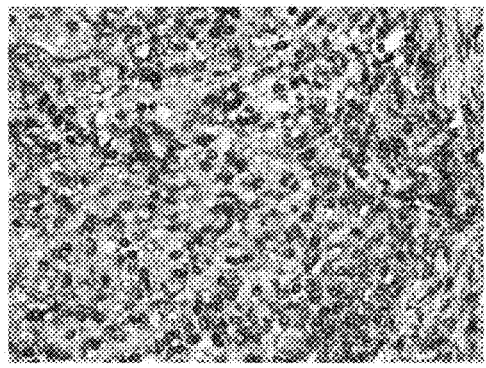

FIG. 22A HCC17 H&E
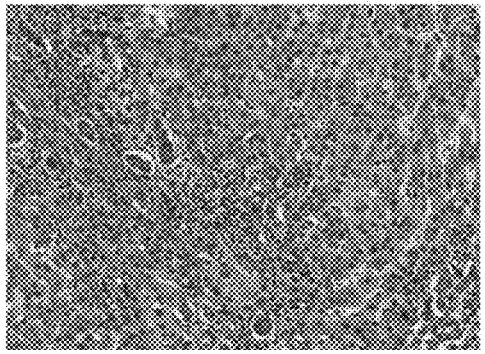
FIG. 22B HCC17 (CD3: 48, CD16: 63)
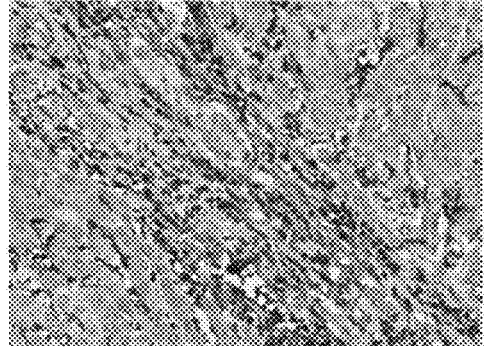
FIG. 22C. VR-384-10-35 H&E
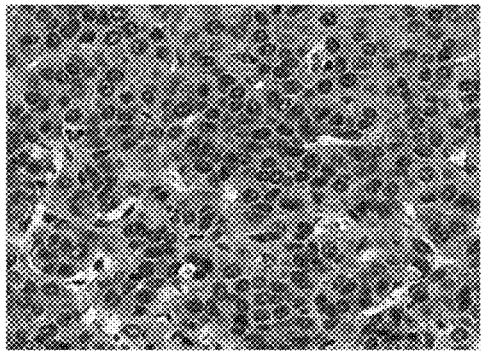
FIG. 22D. VR-384-10-35 (CD3: 18, CD16: 131)
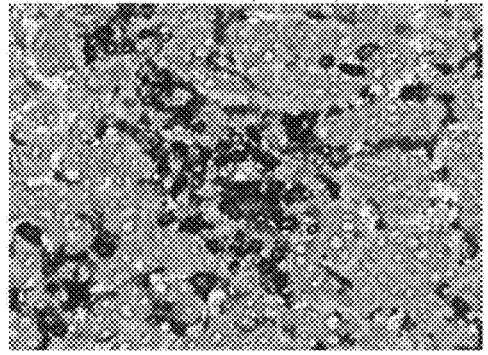
FIG. 22E. LV8012 Core E8 H&E
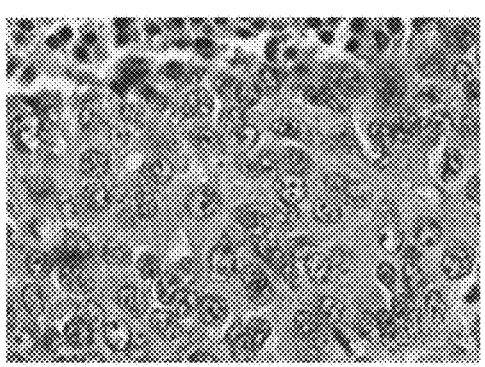
FIG. 22F. LV8012 Core E8 (CD3: 0, CD16: 1)
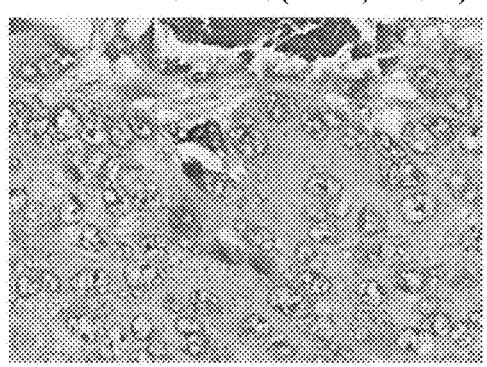

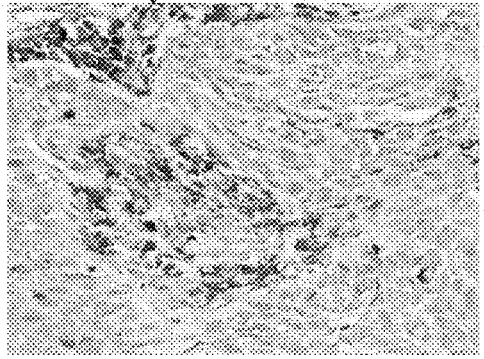
FIG. 23A Day 0
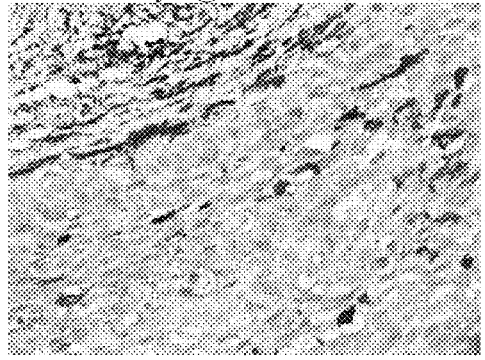
FIG. 23B Day 7 @ 45°C

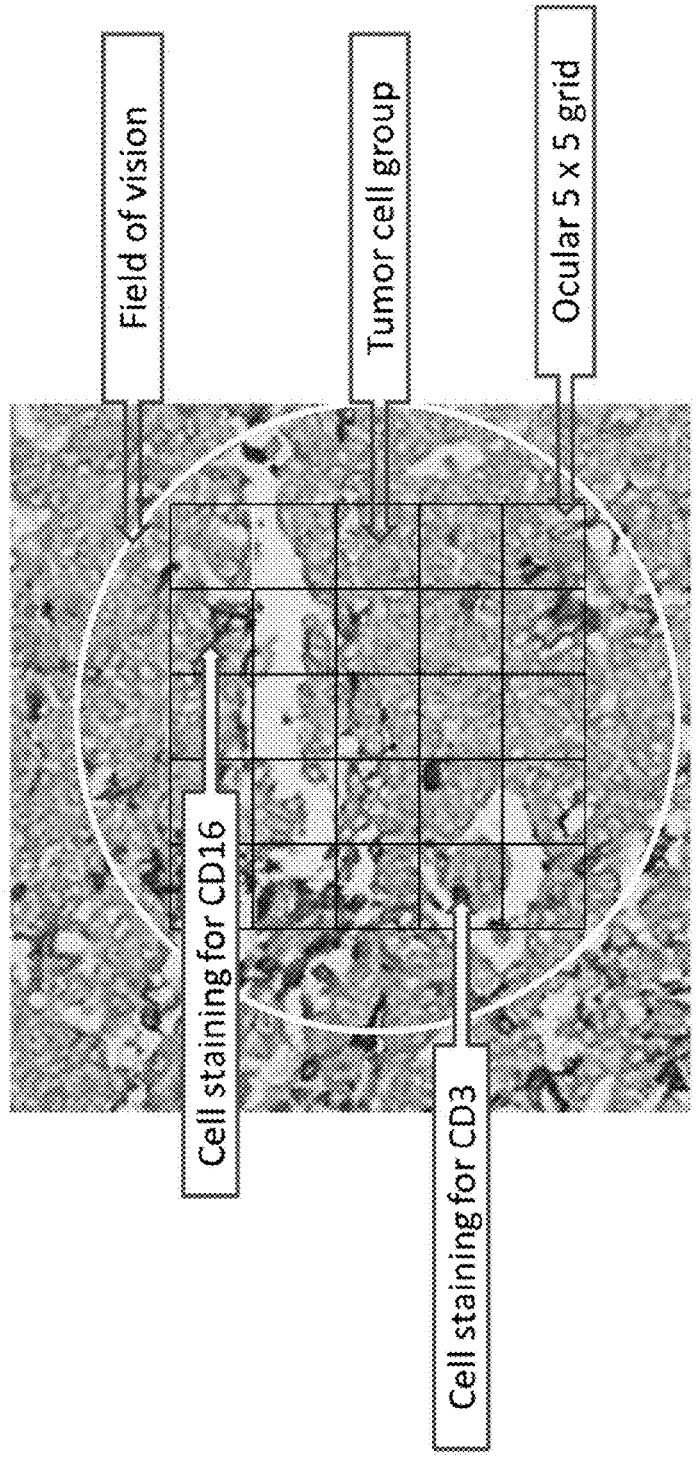

CD3/CD16 scoring by using area of staining

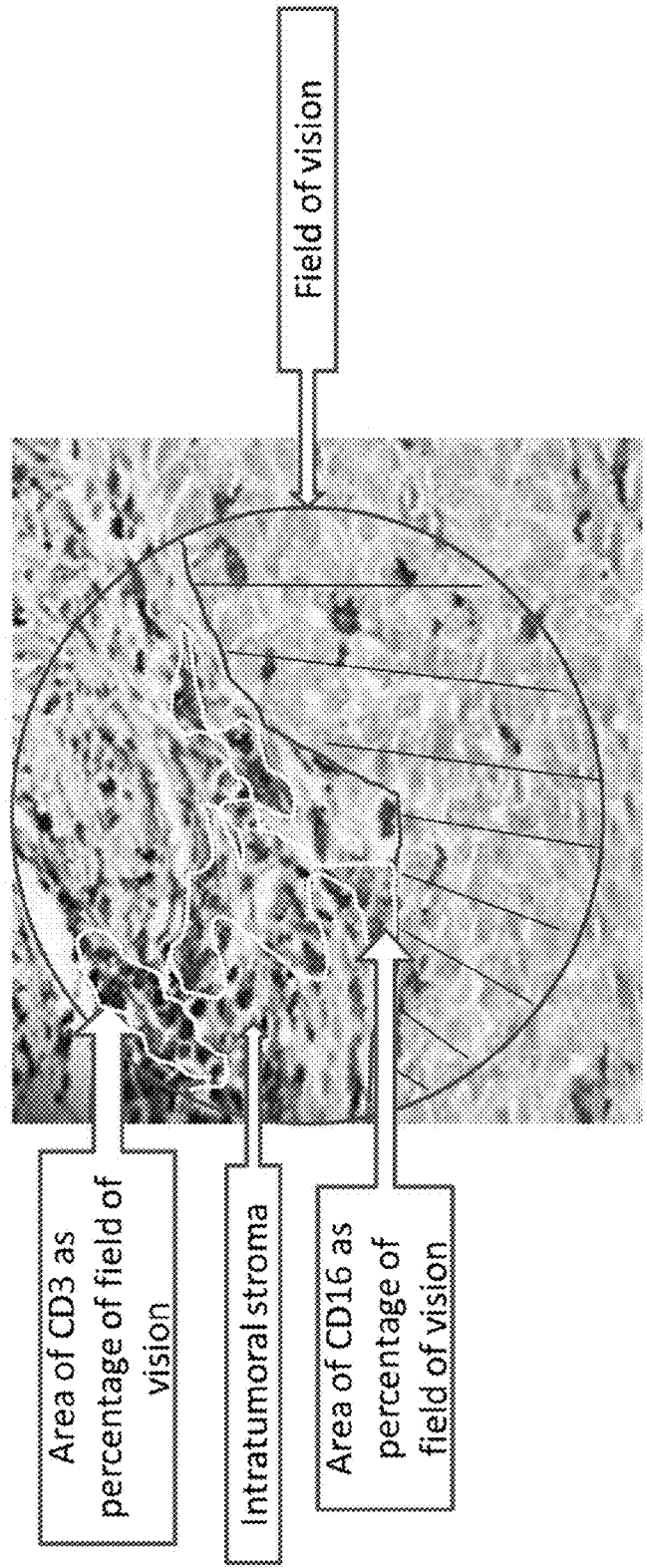
FIG. 28B CD3/CD16 scoring by using area of staining

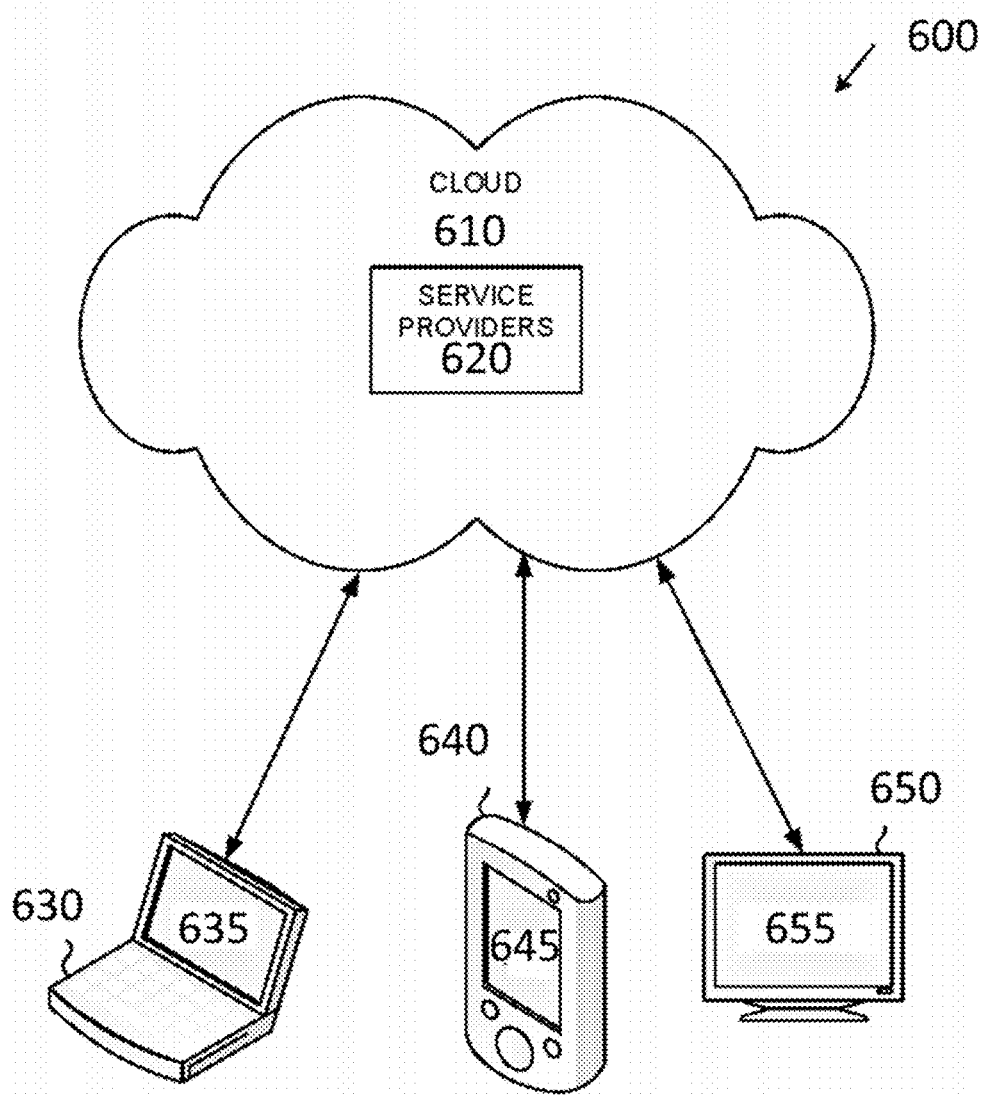

MULTIPLES MULTIPLEX IMMUNOHISTOCHEMICAL ASSAY USING PRIMARY ANTIBODIES OF THE SAME HOST SPECIES

CROSS-REFERENCE TO RELATED APPLICATIONS

This application is a continuation of U.S. Ser. No. 15/585,115, filed May 2, 2017, now issued as U.S. Pat. No. 9,874,571, which is a continuation of U.S. Ser. No. 14/914,345, filed Feb. 25, 2016, now issued as U.S. Pat. No. 9,689,875, which is a national stage entry of PCT/EP2014/067810, filed Aug. 21, 2014, which claims priority from U.S. 61/871,230, filed Aug. 28, 2013, the content of each of which is hereby incorporated by reference.

FIELD

This application relates to methods of detecting CD3 and CD16 proteins in a sample, for example in a cancer sample.

BACKGROUND

The cluster of differentiation, also called cluster of designation (CD) is a nomenclature system used for the identification and investigation of cell surface molecules, either receptors or ligands used for immunophenotyping of cells. T cell receptors (TCR), which reside on the cell surface of T cells, can combine with CD markers forming a complex[1,2]. This complex can classify the type of T cell and its stage in the cell development process. CD3 is a multimeric protein complex that contains one γ, one δ, two ε and two ζ chains, which associate with TCR to form TCR complex[2]. In early stages of T-cell development, CD3 is expressed in the cytoplasm and as the T cell matures, it migrates into the cell membrane[1,2]. CD3 is expressed in all T-cells during all stages of their development making it a specific marker for identification of T-cells[1,2].

CD16 is a member of the Fc receptor family which contributes to the protective functions of the immune system and has two subtypes FcγRIIIa (CD16a) and FcγRIIIb (CD16b). Fc receptors are designed to bind antibodies that are attached to foreign cell types[4]. CD16 is present on the surface of natural killer cells (NK), neutrophils, macrophages, monocytes, and in rare cases activated T cells[4]. CD16 on NK cells can induce antibody-dependent cell-mediated cytotoxicity (ADCC)[3,4,5]. Once the Fc receptor on an NK cell recognizes foreign IgG antibody, the NK cells releases cytokines that enter the foreign cell and promotes cell death by apoptosis[5].

GA201, which is a glycoengineered anti-EGFR human monoclonal antibody, enhances ADCC[6]. GA201 is an IgG1 molecule whose Fc region is glycosylated to increase its binding affinity for FcγRIIIa (CD16a) on immune effector cells. Since GA201 was engineered for high ADCC effectiveness, it has demonstrated increased affinity for low and high CD16 expressed on NK cells, macrophages, and T cell sub populations[6]. This allows CD16 to be used as indicator of the level of GA201 activity in patients with tumors[6]. CD3 has also been suggested to be linked in GA201 activity through triggering of adaptive immunity. This indicates that detecting CD3 and CD16 together can be used to predict a cancer's likely response to GA201[3].

Unfortunately reliable antibodies from different species for CD3 and CD16 are not available. This leads to undesirable cross-reactivity of secondary antibodies used to detect the CD3- and CD16-primary antibodies in a sample. Thus, methods are needed that permit detection of proteins using primary antibodies from the same species (e.g., mouse CD3 and mouse CD16 antibodies, or rabbit CD3 and rabbit CD16 antibodies).

SUMMARY

An automated immunohistochemistry (IHC) procedure for the detection of CD3 and CD16 as a dual IHC assay is provided. In some examples, the methods permits detection of CD3 and CD16 in formalin fixed, paraffin embedded tissues (FFPE), such as a cancer sample, such as a sample from a head/neck, colorectal, heptatocellular or non-small cell carcinomas. The disclosed methods can provide consistent staining across a variety of assay parameters, and offer desired levels of specificity, accuracy, and analytical precision. The disclosed methods permit the use of at least two different primary antibodies for CD3 and CD16 from the same host species (e.g., a rabbit CD3 primary antibody and a rabbit CD16 primary antibody). Methods to denature and block the first primary antibody contacted with the sample are provided.

Provided herein are methods of detecting CD3 protein and CD16 protein in a sample. One or more of the disclosed steps in the method can be automated, for example using a suitably programmed computer and/or other instrumentation. In particular examples, the methods include contacting the sample with a buffer comprising Tris, a preservative, wherein the buffer pH is about 8-9. In some examples, the buffer is CC1 (Ventana Medical Systems Inc., catalog #950-124). The sample is then contacted with a CD3 antibody (such as rabbit monoclonal antibody clone 2GV6 (Ventana Medical Systems Inc., catalog #790-4341). The sample is then contacted with a labeled secondary antibody to permit detection of the CD3 antibody (such as an anti-rabbit-HQ conjugate and an anti-HQ-HRP antibody). The sample is denatured by incubating the sample at about 80° C.-100° C. for at least 5 minutes. The sample is contacted sample with a blocking antibody, such as a chicken anti-rabbit antibody if the CD3 antibody is a rabbit antibody. Optionally, the method can include contacting the sample with a reaction buffer, for example a Tris buffer at a pH of about 7.6+/−0.2 (such as Ventana Medical Systems Inc., catalog #950-300), for at least 20 minutes to remove residual blocking antibody. The sample is then contacted with the buffer comprising Tris, a preservative, wherein the buffer pH is about 8-9. The sample is then contacted with a CD16 antibody (such as rabbit monoclonal antibody clone SP189, Spring Bioscience, catalog #M475). The sample is then contacted with a labeled secondary antibody to permit detection of the CD16 antibody (such as an anti-rabbit-AP multimer or an anti-mouse-AP multimer). It is then determine whether CD3 and/or CD16 are detected in the sample. It is determined that CD3 protein is present in the sample if the labeled secondary antibody to permit detection of the CD3 antibody is detected, and that CD16 protein is present in the sample if the labeled secondary antibody to permit detection of the CD16 antibody is detected.

In some examples, the method also includes scoring the presence of CD3 protein and CD16 protein. For example, if the sample is a tumor sample, the scoring can include determining an absolute number of cells staining with the CD3 antibody within the tumor cells of the sample using a 5×5 ocular grid with an area of 0.25 square millimeter, determining an absolute number of cells staining with the CD16 antibody within the tumor cells of the sample using a 5×5 ocular grid with an area of 0.25 square millimeter, extrapolating the absolute number of cells staining with the CD3 antibody to a number of cells in a 1 square millimeter region, and extrapolating the absolute number of cells staining with the CD16 antibody to a number of cells in a 1 square millimeter region, thereby generating a score of CD3 protein and CD16 protein. Thus, the absolute number of cells staining with CD3 and CD16 in the grid can be determined, and applied to a formula In another example, the scoring can include determining the area of staining with the CD3 antibody and the CD16 antibody within the intratumoral and contiguous peri-tumoral stroma of the sample (e.g., intratumoral stroma and contiguous peri-tumoral stroma), dividing the area of staining with the CD3 antibody in the intratumoral and contiguous peri-tumoral stroma by the area of total stroma (e.g., field of vision), thereby generating a score of CD3 protein for the stroma, and dividing the area of staining with the CD16 antibody in the intratumoral and contiguous peri-tumoral stroma by the area of total stroma (e.g., field of vision), thereby generating a score of CD16 protein for the stroma. Thus, the percent of CD3 and CD16 staining can be the area of intra-tumoral and peri-tumoral stroma that stains for CD3 or CD16 as percentage of total area of stroma.

In some examples, combinations of these scoring methods are used.

The disclosed methods in some examples are used to determine the likelihood that a tumor will respond to an anti-EGFR targeted therapeutic agent (such as GA201). In such examples, the method can further include determining that the tumor will respond to the anti-EGFR targeted therapeutic agent if the sample has an increased CD3 and/or CD16 score relative to a normal sample, or determining that the tumor will not respond to the anti-EGFR targeted therapeutic agent if the sample has a similar or decreased CD3 and/or CD16 score relative to a normal sample.

The disclosed methods in some examples are used to determine whether a tumor responded to an anti-EGFR targeted therapeutic agent (such as GA201). In such examples, the method can further include determining that the tumor responded to the anti-EGFR targeted therapeutic agent if the sample has a decreased CD3 and/or CD16 score relative to a normal sample (e.g., non-tumoral sample), or determining that the tumor responded to the anti-EGFR targeted therapeutic agent if the sample has a similar or decreased CD3 and/or CD16 score relative to a normal sample.

Also provided are one or more computer-readable storage media that include computer-executable instructions causing a computer to perform the methods provided herein.

A system for analyzing a sample is also provided. The system can include a means to store a plurality of samples, such as FFPE samples present on glass slides. The system can further include one or more dispensers, such as those for dispensing buffers, blocking antibodies, primary antibodies, secondary antibodies, and regents for detecting the antibodies (e.g., diaminobenzidine, napthol, alkaline phosphatase enhancer and fast red). The system can further include a means to detect the CD3 and CD16 staining, such as an imager and/or a detector configured to detect and display signals (e.g., labels) associated with the CD3 and CD16 primary antibodies. The system can further include a processor configured to collect (and in some example store) images showing CD3 and CD16 staining using the antibodies.

The foregoing and other objects and features of the disclosure will become more apparent from the following detailed description, which proceeds with reference to the accompanying figures.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 1A-1F is a series of digital images showing representative CD16 photomicrographs of tissues screened for appropriate localization and optimal background reactivity are shown. A, C, and E are H&E images, B, D, and F are CD16 antibody stained images. Photos were taken using a 40× objective.

FIGS. 2A-2F is a series of digital images showing a CD16 antibody titration series. Titration of the anti-CD16 antibody was performed on 90S-3514-C4B non-small cell lung cancer. A is an H&E image and B-F are CD16 antibody stained images. Photos were taken using a 40× objective.

FIGS. 3A-3F is a series of digital images showing representative photomicrographs of non-small cell lung cancer specimen 90S-3514-C4B screened for different CD16 antibody diluents. Photos were taken using a 40× objective.

FIGS. 4A-4F is a series of digital images showing analysis of CD16 antibody staining under optimized conditions. A, C, and E are H&E images, B, D, and F are CD16 antibody stained images. The assay was applied to 91S-4130-E1 head/neck cancer (A-B), 5931 colorectal cancer (C-D), and 90S-3514-C4B non-small cell lung cancer (E-F). Photos were taken using a 40× objective.

FIGS. 5A-5F are a series of digital images showing analysis of CD3/CD16 staining. A, C, and E are H&E images, B, D, and F are CD3/CD16 antibody stained images. Representative photomicrographs of tissues screened for appropriate localization and optimal background reactivity are shown (A-F). Photos were taken using a 40× objective.

FIGS. 6A-6D is a series of digital images showing different amounts of time under cell conditioning condition 1 (CC1) on CD3 staining. Representative photomicrographs of 90S-3514-C4B non-small cell lung cancer screened for appropriate epitope retrieval are shown. Photos were taken using a 40× objective.

FIGS. 7A-7C is a series of digital images showing different amounts of time under cell conditioning condition 1 (CC1) on CD16 staining. Representative photomicrographs of 90S-3514-C4B non-small cell lung cancer screened for appropriate epitope retrieval are shown. Photos were taken using a 40× objective.

FIGS. 8A-8C is a series of digital images showing effect of different lengths of denaturation time at 95° C. on removal of unbound CD3 antibody. Representative photomicrographs of 90S-3514-C4B non-small cell lung cancer screened for appropriate antibody denaturation. Photos were taken using a 40× objective FIGS. 9A-9D is a series of digital images showing different amounts of blocking antibody (chicken anti-rabbit antibody) in 5931 colorectal cancer. Photos were taken using a 40× objective.

FIGS. 10A-10F is a series of digital images showing CD3/CD16 DIHC using optimized conditions. The assay was applied to 91S-4130-E1 head/neck cancer (A-B), 5931 colorectal cancer (C-D), and 90S-3514-C4B non-small cell lung cancer (E-F). A, C, and E are H&E images, B, D, and F are CD3/CD16 antibody stained images. Photos were taken using a 40× objective.

FIGS. 11A-11F is a series of digital images showing CD3/CD16 expression in normal and neoplastic Tissues. A multi-tissue array was stained with the anti-CD3 and anti-CD16 antibody. Absolute cell counts are indicated in parentheses. A, C, and E are H&E images, B, D, and F are CD3/CD16 antibody stained images. Photos were taken using a 40× objective.

FIGS. 12A-12D are bar graphs showing the precision of CD3/CD16 detection by H score. Inter-run and inter-instrument membrane H scores measured by manual pathology reads are shown (A, B). Average H scores are plotted. The coefficient of variation (as a percentage) of image analysis for all slides was 4.2% (CD3)/1.7% (CD16) for inter-run precision and 13.7% (CD3)/10.3% (CD16) for inter-instrument precision.

FIGS. 13A-13E is a series of digital images showing inter-run assay consistency. Representative photomicrographs from three separate runs of non-small cell lung cancer 90S-3514-C4B stained with anti-CD3 and anti-CD16 antibody following the developed IHC protocol. The negative control slide stained with antibody diluent A is also shown. Photos were taken using a 40× objective.

FIGS. 14A-14E is a series of digital images showing inter-instrument assay consistency. Representative photomicrographs of slides from three separate runs on three separate instruments stained with the anti-CD3/CD16 antibodies following the developed IHC protocol are shown. Optical density scores are indicated in parentheses. Photos were taken using a 20× objective.

FIGS. 16A-16F is a series of digital images showing CD3/CD16 expression in cores from the head and neck cancer cores of HNT1021. A, C, and E are H&E images, B, D, and F are CD3/CD16 antibody stained images. CD3/CD16 cell counts are indicated in parentheses. The photomicrographs were taken using a 40× objective.

FIGS. 18A-18F is a series of digital images showing CD3/CD16 expression in cores from the colorectal cancer array COC1021. A, C, and E are H&E images, B, D, and F are CD3/CD16 antibody stained images. CD3/CD16 cell counts are indicated in parentheses. The photomicrographs were taken using a 40× objective.

FIGS. 20A-20F is a series of digital images showing CD3/CD16 expression in cores from the non-small cell lung cancer array LUC1021. A multi-tissue array was stained with the anti-CD3 and the anti-CD16 antibody. Absolute cell counts are indicated in parentheses. A, C, and E are H&E images, B, D, and F are CD3/CD16 antibody stained images. The photomicrographs were taken using a 40× objective.

FIGS. 22A-22F are digital images showing representative photomicrographs of Cores from the hepatocellular carcinoma (HCC) specimens. CD3/CD16 cell counts are indicated in parentheses. Photomicrographs were taken using a 40× objective.

FIGS. 23A-23B are digital images showing representative photomicrographs of accelerated stability testing of anti-CD3 and anti CD16 antibody. CD3/CD16 H-scores are indicated in parentheses. Photomicrographs were taken using a 20× objective.

FIGS. 27A and 27B show an exemplary scoring method for CD3 and CD16 by counting cells that are positive for CD3, CD16 or both, in a grid.

FIGS. 28A and 28B show an exemplary scoring method for CD3 and CD16 by determining the area of intra-tumoral and peri-tumoral stroma that stains for CD3 or CD16 presented as percentage of total area of stroma.

FIG. 30 is an exemplary cloud-support environment 600 that can be used in conjunction with the technologies described herein.

DETAILED DESCRIPTION

Figure 3B:
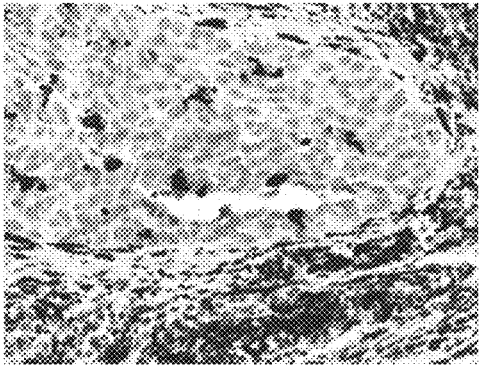
Figure 3C:
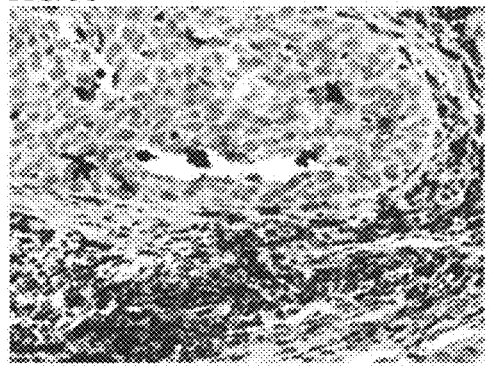
Figure 3D:
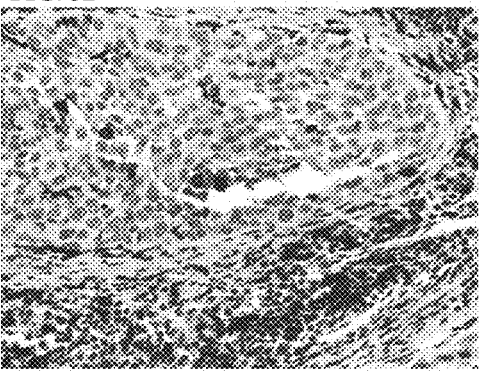
Figure 3E:
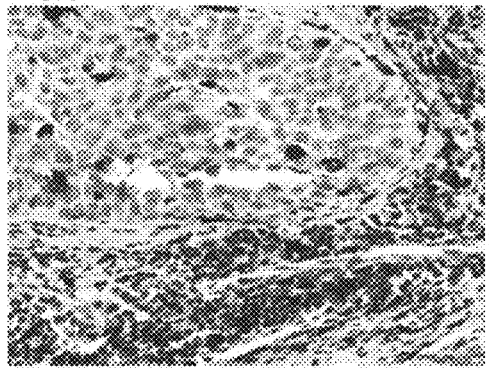
Figure 3F:
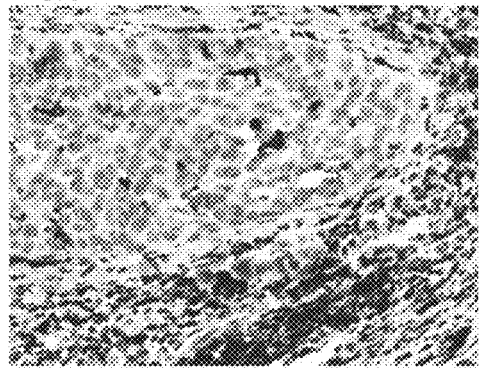
Figure 15A:
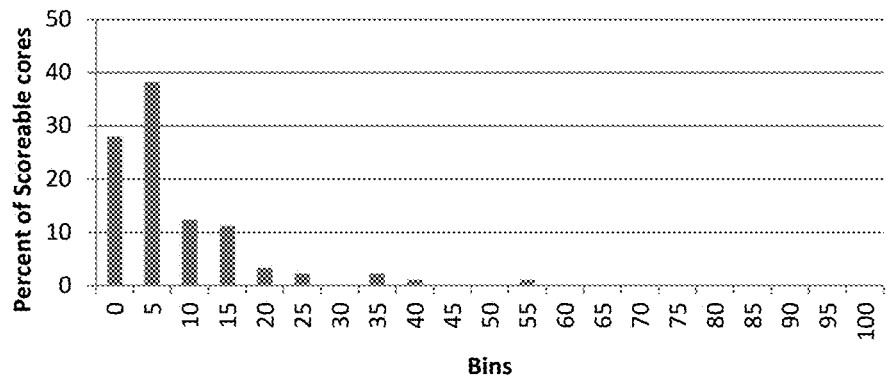
FIGS. 15A-15B are bar graphs showing the frequency distribution of Frequency Distribution of CD3 (A) and CD16 (B) cell counts for head and neck cancer cores of HNT1021.
Figure 15B:
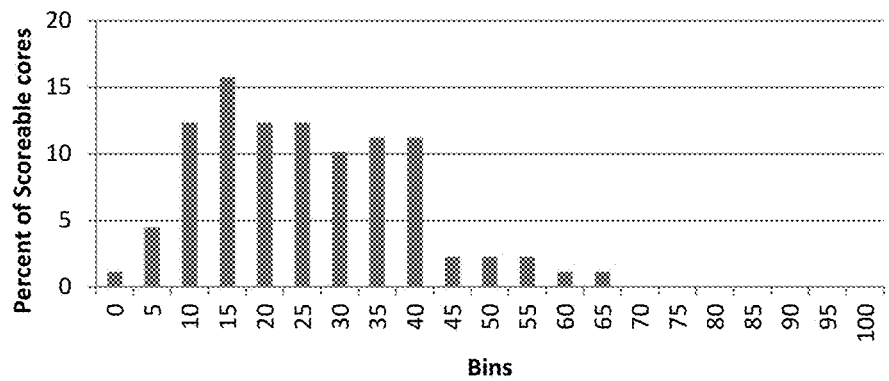
Figure 17A:
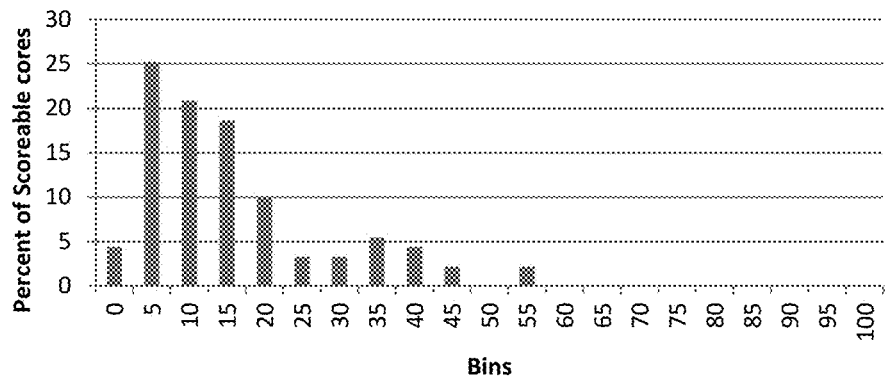
FIGS. 17A-17B are bar graphs showing the frequency distribution of CD3 (A) CD16 (B) cell counts for colorectal cancer cores of COC1021.
Figure 17B:
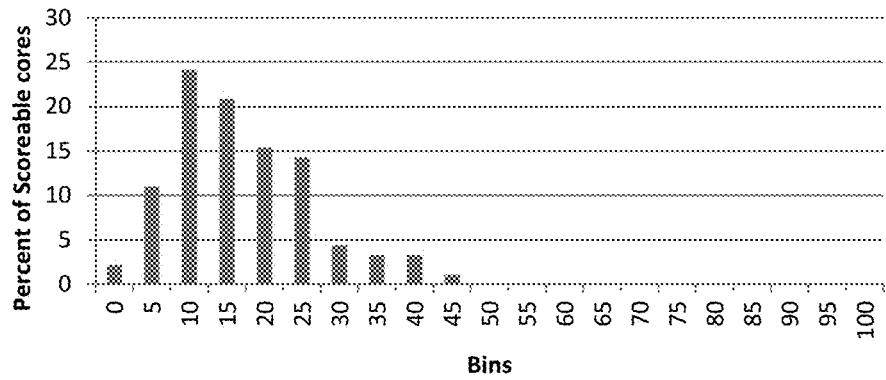
Figure 19A:
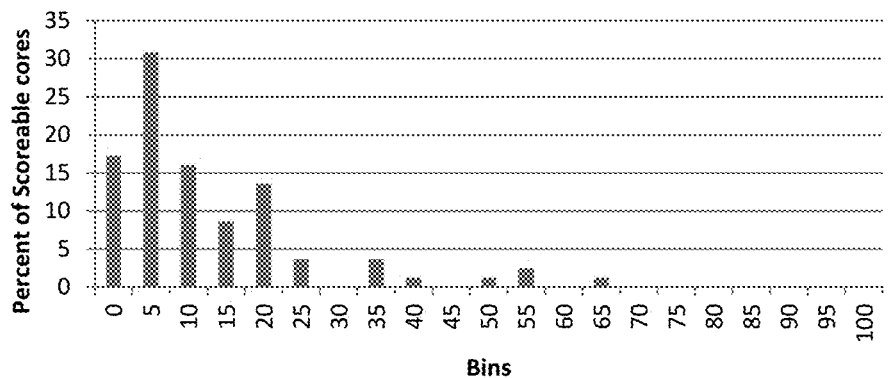
FIGS. 19A-19B are bar graphs showing the frequency distribution of CD3 (A) and CD16 (B) cell counts in non-small cell lung cancer cores of LUC1021.
Figure 19B:
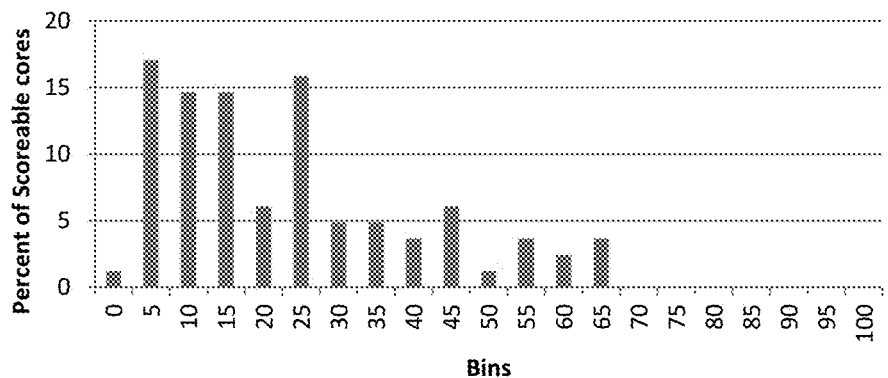

The following explanations of terms and methods are provided to better describe the present disclosure and to guide those of ordinary skill in the art in the practice of the present disclosure. The singular forms "a," "an," and "the" refer to one or more than one, unless the context clearly dictates otherwise. For example, the term "comprising a cell" includes single or plural cells and is considered equivalent to the phrase "comprising at least one cell." The term "or" refers to a single element of stated alternative elements or a combination of two or more elements, unless the context clearly indicates otherwise. As used herein, "comprises" means "includes." Thus, "comprising A or B," means "including A, B, or A and B," without excluding additional elements. Dates of GenBank® Accession Nos. referred to herein are the sequences available at least as early as Aug. 28, 2013. All references and GenBank® Accession numbers cited herein are incorporated by reference.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting.

In order to facilitate review of the various embodiments of the disclosure, the following explanations of specific terms are provided:

Antibody: Immunoglobulin molecules and immunologically active portions of immunoglobulin molecules, that is, molecules that contain an antigen binding site that specifically binds (immunoreacts with) an antigen (such as CD3 or CD16). Exemplary antibodies include monoclonal, polyclonal, and humanized antibodies, such as those that are specific for CD3 or CD16 (such as the antibodies listed in Table 3). In some examples, antibodies can be diagnostic, that is, use to detect the presence of a protein such as CD3 or CD16. In other examples, antibodies are therapeutic (such as GA201), for example to treat a cancer, such as an EGFR overexpressing cancer.

In some examples, an antibody has a high binding affinity for CD3 or CD16, such as a binding affinity of at least about $1 \times 10^{-8}$ M, at least about $1.5 \times 10^{-8}$, at least about $2.0 \times 10^{-8}$, at least about $2.5 \times 10^{-8}$, at least about $3.0 \times 10^{-8}$, at least about $3.5 \times 10^{-8}$, at least about $4.0 \times 10^{-8}$, at least about $4.5 \times 10^{-8}$, or at least about $5.0 \times 10^{-8}$ M. In certain embodiments, an antibody that binds to CD3 or CD16 has a dissociation constant (Kd) of ≤104 nM, ≤100 nM, ≤10 nM, ≤1 nM, ≤0.1 nM, ≤0.01 nM, or ≤0.001 nM (e.g., $10^{-8}$M or less, e.g., from $10^{-8}$M to $10^{-13}$M, e.g., from $10^{-9}$ M to $10^{-13}$ M). In one embodiment, Kd is measured by a radiolabeled antigen binding assay (RIA) performed with the Fab version of an antibody of interest and its antigen (see, e.g., Chen et al., *J. Mol. Biol.* 293:865-881, 1999). In another example, Kd is measured using surface plasmon resonance assays using a BIACORES-2000 or a BIACORES-3000 (BIAcore, Inc., Piscataway, N.J.) at 25° C. with immobilized antigen CMS chips at about 10 response units (RU).

A naturally occurring antibody (such as IgG, IgM, IgD) includes four polypeptide chains, two heavy (H) chains and two light (L) chains interconnected by disulfide bonds. As used herein, the term antibody also includes recombinant antibodies produced by expression of a nucleic acid that encodes one or more antibody chains in a cell (for example see U.S. Pat. No. 4,745,055; U.S. Pat. No. 4,444,487; WO 88/03565; EP 256,654; EP 120,694; EP 125,023; Faoulkner et al., Nature 298:286, 1982; *Morrison, J. Immunol.* 123: 793, 1979; Morrison et al., *Ann Rev. Immunol.* 2:239, 1984).

The term antibody also includes an antigen binding fragment of a naturally occurring or recombinant antibody. Specific, non-limiting examples of binding fragments encompassed within the term antibody include Fab, (Fab')$_2$, Fv, and single-chain Fv (scFv). Fab is the fragment that contains a monovalent antigen-binding fragment of an antibody molecule produced by digestion of whole antibody with the enzyme papain to yield an intact light chain and a portion of one heavy chain or equivalently by genetic engineering. Fab' is the fragment of an antibody molecule obtained by treating whole antibody with pepsin, followed by reduction, to yield an intact light chain and a portion of the heavy chain; two Fab' fragments are obtained per antibody molecule. (Fab')$_2$ is the fragment of the antibody obtained by treating whole antibody with the enzyme pepsin without subsequent reduction or equivalently by genetic engineering. F(Ab')$_2$ is a dimer of two FAb' fragments held together by disulfide bonds. Fv is a genetically engineered fragment containing the variable region of the light chain and the variable region of the heavy chain expressed as two chains. Single chain antibody ("SCA") is a genetically engineered molecule containing the variable region of the light chain, the variable region of the heavy chain, linked by a suitable polypeptide linker as a genetically fused single chain molecule. Methods of making these fragments are routine in the art.

Cluster of Differentiation 3 (CD3): A T cell co-receptor protein complex composed of four chains. In mammals, the complex contains a CD3γ chain (OMIM 186740), a CD3δ chain (OMIM 186790), and two CD3ε chains (OMIM 186830). These chains associate with the T-cell receptor (TCR) and the ζ-chain to generate an activation signal in T lymphocytes. The TCR, ζ-chain, and CD3 molecules together comprise the TCR complex, which can differentiate infiltrating T cells from other infiltrating cell types.

The present application provides methods of detecting CD3 expression. In such methods, any of the CD3γ chain, CD3δ chain, CD3ε chain, or combinations thereof, can be detected.

CD3 sequences are publically available, for example from GenBank® sequence database (e.g., amino acids 23-182 of Accession No. NP_000064 and Accession No. NM_000073.2, CD3γ chain protein and nucleic acid, respectively; amino acids 22-171 of Accession No. NP_000723 or amino acids 22-127 of Accession No. NP_001035741 and Accession Nos. NM_000732.4 or NM_001040651.1, CD3 δ chain protein and nucleic acid, respectively; and amino acids 23-207 of Accession No. NP_000724 and Accession No. NM_000733.3, CD3 ε chain protein and nucleic acid, respectively). One of ordinary skill in the art can identify additional CD3 nucleic acid and protein sequences, including CD3 variants.

Cluster of Differentiation 16 (CD16): A member of the Fc receptor family which contributes to the protective functions of the immune system and has two subtypes FcγRIIIa (CD16a, OMIM 146740) and FcγRIIIb (CD16b, OMIM 610665). CD16 is present on the surface of natural killer cells (NK), macrophages, monocytes, and in rare cases T cells. CD16 on NK cells can induce antibody-dependent cell-mediated cytotoxicity (ADCC).

The present application provides methods of detecting CD16 expression. In a specific example, FcγRIIIa is detected.

The genes encoding human CD16a and CD16b are on chromosome 1q23.3. CD16 sequences are publically available, for example from GenBank® sequence database (e.g., accession numbers NP_000560.5, NP_001121064.1, NP_001121067.1 and NP_001121068.1 (CD16a protein), and NM_000569.6, NM_001127592.1, NM_001127593.1, NM_001127595.1 and NM_001127596.1 (CD16a nucleic acid)). One of ordinary skill in the art can identify additional CD16 nucleic acid and protein sequences, including CD16 variants.

Contact: To bring one agent into close proximity to another agent, thereby permitting the agents to interact. For example, a CD3 antibody can be applied to a microscope slide or other surface containing a biological sample, thereby permitting detection of CD3 proteins in the sample that are specifically recognized by the CD3 antibody.

Detect: To determine if an agent is present or absent. In some examples this can further include quantification. For example, use of an antibody specific for a particular protein (e.g., CD3 or CD16) permits detection of the protein in a sample, such as a sample containing cancer tissue. In particular examples, an emission signal from a detectable label (such as an increase in the signal if the target is present) is detected. Detection can be in bulk, so that a macroscopic number of molecules can be observed simultaneously. Detection can also include identification of signals from single molecules using microscopy and such techniques as total internal reflection to reduce background noise.

EGFR-targeted therapy: Includes those agents that can be used to treat an EGFR-expressing tumor, for example by killing ore reducing growth of tumor cells that express EGFR. In some examples, such agents inhibit or decrease EGFR activity. In some examples, an EGFR-targeted therapy can include a small molecule, a protein (such as an antibody, or an antibody conjugated to a toxin), or a nucleic acid (such as an antisense molecule). In some examples, such molecules kill or reduce growth of EGFR-expressing cells (or CD3 and/or CD16 expressing tumor cells). 100% killing or inhibition of growth is not required. In some examples, an EGFR-targeted therapy kills at least 20%, at least 30%, at least 40%, at least 50%, at least 75%, at least 90%, at least 95%, or at least 99% of EGFR-expressing tumor cells (or CD3 and/or CD16 expressing tumor cells). A particular example of an EGFR-targeted therapy is an anti-EGFR-targeted therapy, such as an EGFR antibody, such as GA201. In some examples, such agents can be used to treat a tumor that overexpresses CD3 and/or CD16.

Label: An agent capable of detection, for example by spectrophotometry, flow cytometry, or microscopy (such as light microscopy). For example, one or more labels can be attached to an antibody, thereby permitting detection of the target protein (such as CD3 or CD16). Exemplary labels include radioactive isotopes, fluorophores, ligands, chemiluminescent agents, haptens, enzymes, and combinations thereof.

Normal cells or tissue: Non-tumor, non-malignant cells and tissue. In some examples normal cells or tissue are used as a control, for example are from the same tissue type as the tumor being analyzed (e.g., if the tumor is a NSCLC, the normal tissue or cell can be a normal non-cancerous lung tissue or cell).

Sample: A biological specimen containing genomic DNA, RNA (including mRNA), protein, intact cells (e.g., a tissue sample), or combinations thereof, obtained from a subject. Examples include a specimen containing at least one cancer cell (a cancer sample or cancer tissue sample), for example, a tissue or tumor biopsy, fine needle aspirate, bronchioalveolar lavage, pleural fluid, sputum, surgical specimen, lymph node, a metastasis, or autopsy material. In other examples, a sample includes a control sample, such as a non-cancerous cell or tissue sample. In one example the control is a negative control, such as a sample known to not include detectable CD3 protein, CD16 protein, or both. In another example, the control is a positive control, such as a sample known to include detectable CD3 protein, CD16 protein, or both.

Specific binding agent: An agent that binds substantially or preferentially only to a defined target such as a protein, for example a CD3 or CD16 protein.

A CD3 or CD16 protein-specific binding agent binds substantially only to CD3 or CD16 protein, respectively or to a specific region within the CD3 or CD16 protein, respectively. For example, a "CD3 specific binding agent" includes antibodies and other agents, such as aptamers, that bind substantially to a CD3 polypeptide. Antibodies can be monoclonal or polyclonal antibodies that are specific for the polypeptide, as well as immunologically effective portions ("fragments") thereof. The determination that a particular agent binds substantially only to a CD3 or CD16 polypeptide may readily be made by using or adapting routine procedures. One suitable in vitro assay makes use of the Western blotting procedure (described in many standard texts, including Harlow and Lane, Using Antibodies: A Laboratory Manual, CSHL, New York, 1999).

Subject: Living multi-cellular vertebrate organisms, a category that includes human and non-human mammals, such as veterinary subjects. In a particular example, a subject is one who has or is suspected of having cancer, such as a CD3/CD16-expressing cancer, for example head and neck cancer, colorectal cancer, HCC, or non-small cell lung cancer.

Therapeutically effective amount: A dose sufficient to prevent advancement, delay progression, or to cause regression of a disease, or which is capable of reducing symptoms caused by the disease, such as cancer, for example head and neck cancer, colorectal cancer, HCC, or non-small cell lung cancer. In one example, a therapeutically effective amount is an amount of a EGFR-targeted therapy sufficient to reduce the size or volume of a tumor, or the number of tumors (such as the number of metastases) by at least 10%, at least 20%, at least 50%, at least 70%, or at least 90%, such as reduce the size, volume or number (such as metastases) of a head and neck, colorectal, HCC or non-small cell lung carcinoma by at least 10%, at least 20%, at least 50%, at least 70%, or at least 90%.

Under conditions sufficient for: A phrase that is used to describe any environment that permits the desired activity. An example includes contacting an antibody with a biological sample sufficient to allow detection of one or more target proteins (e.g., CD3 and CD16) in the sample.

Overview

This disclosure provides methods and systems for an immunohistochemistry (IHC) assay to detect CD3 and CD16, such as a dual chromogenic IHC assay. This disclosed assay permits the use of at least two different primary antibodies from the same host species (e.g., a rabbit CD3 primary antibody and a rabbit CD16 primary antibody). In some examples, the method does not use single species multimer antibodies.

Figure 24A:
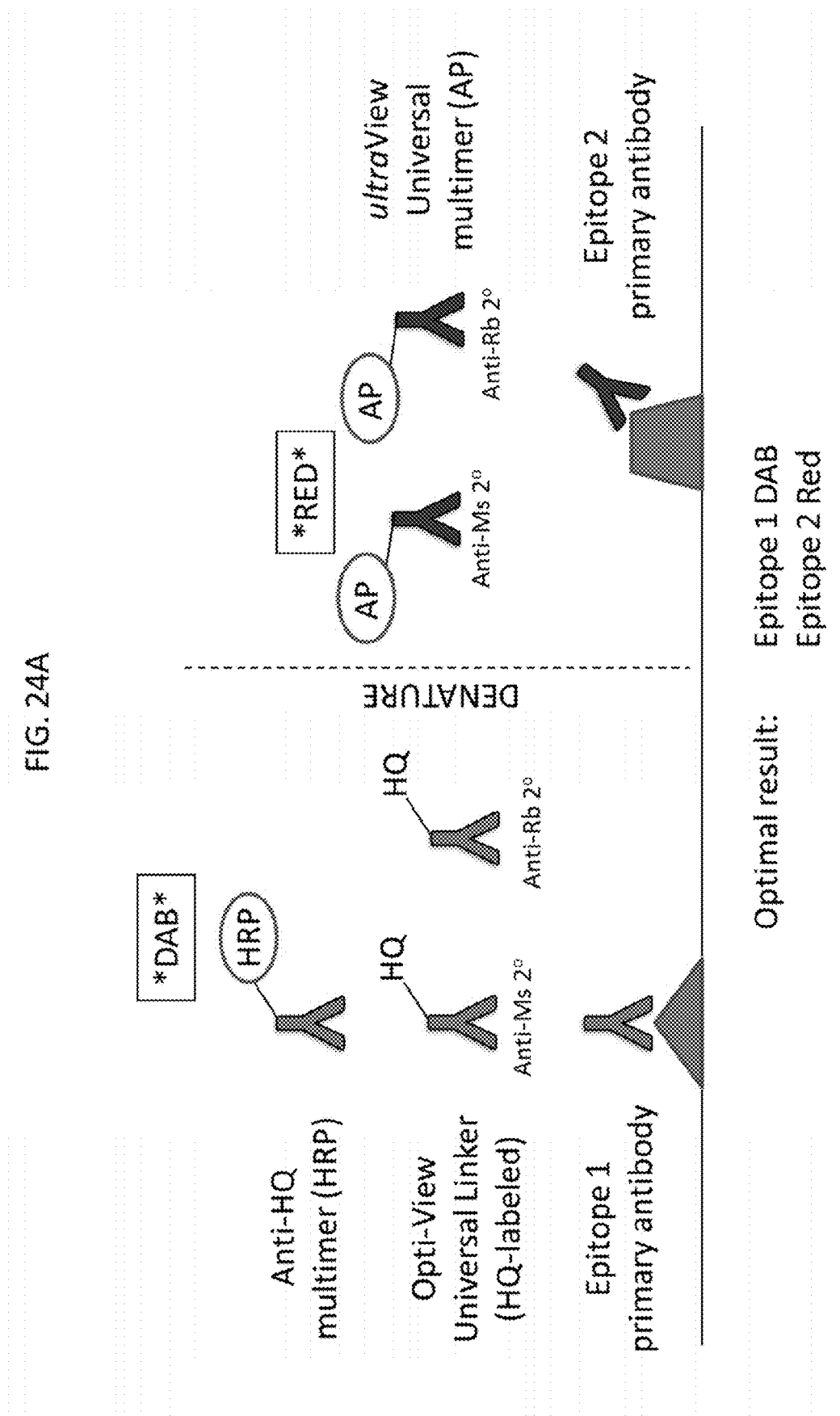
FIGS. 24A-24C are schematic drawings showing (A) detection of two different epitopes using different secondary antibody systems, (B) how undesired cross reactivity can result if both primary antibodies are from the same host species, and (C) how this cross-reactivity can be reduced using blocking antibodies.
Figure 24B:
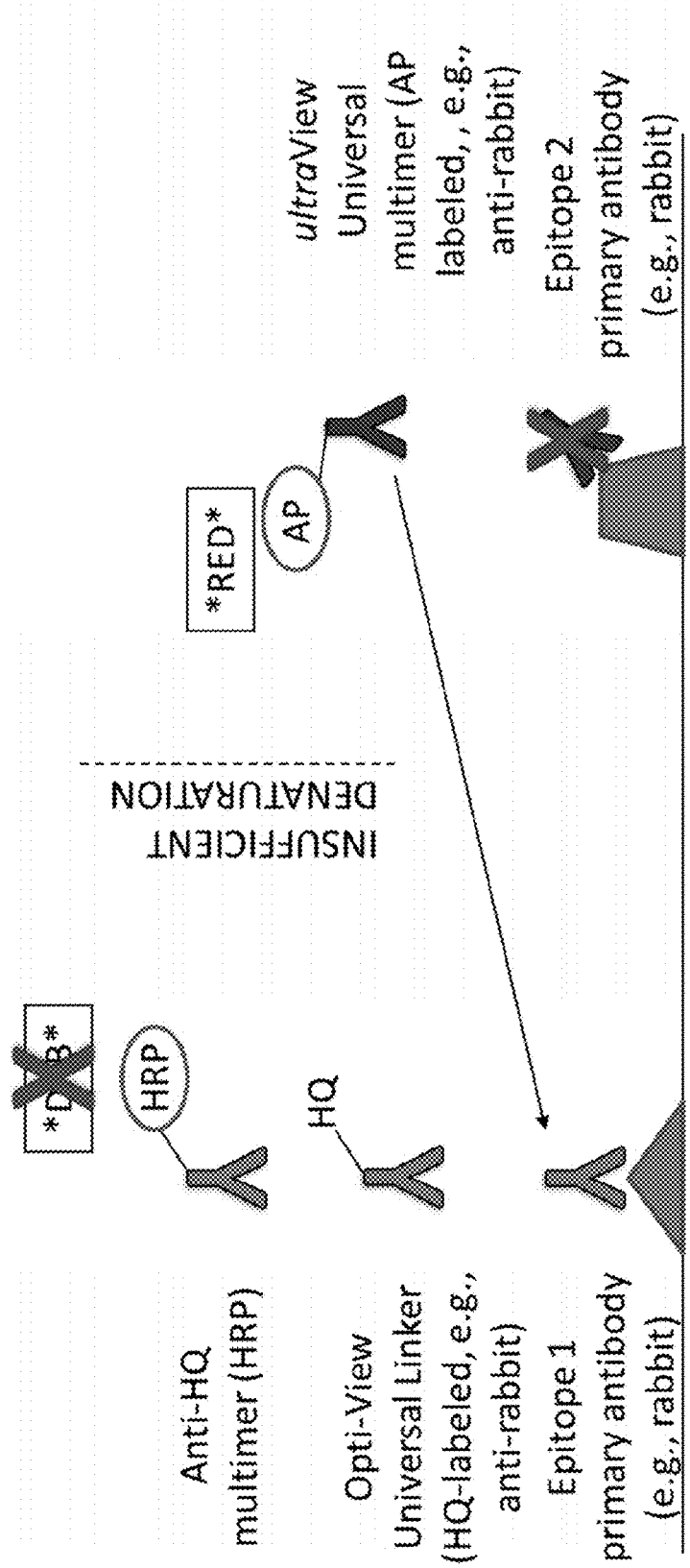
Figure 24C:
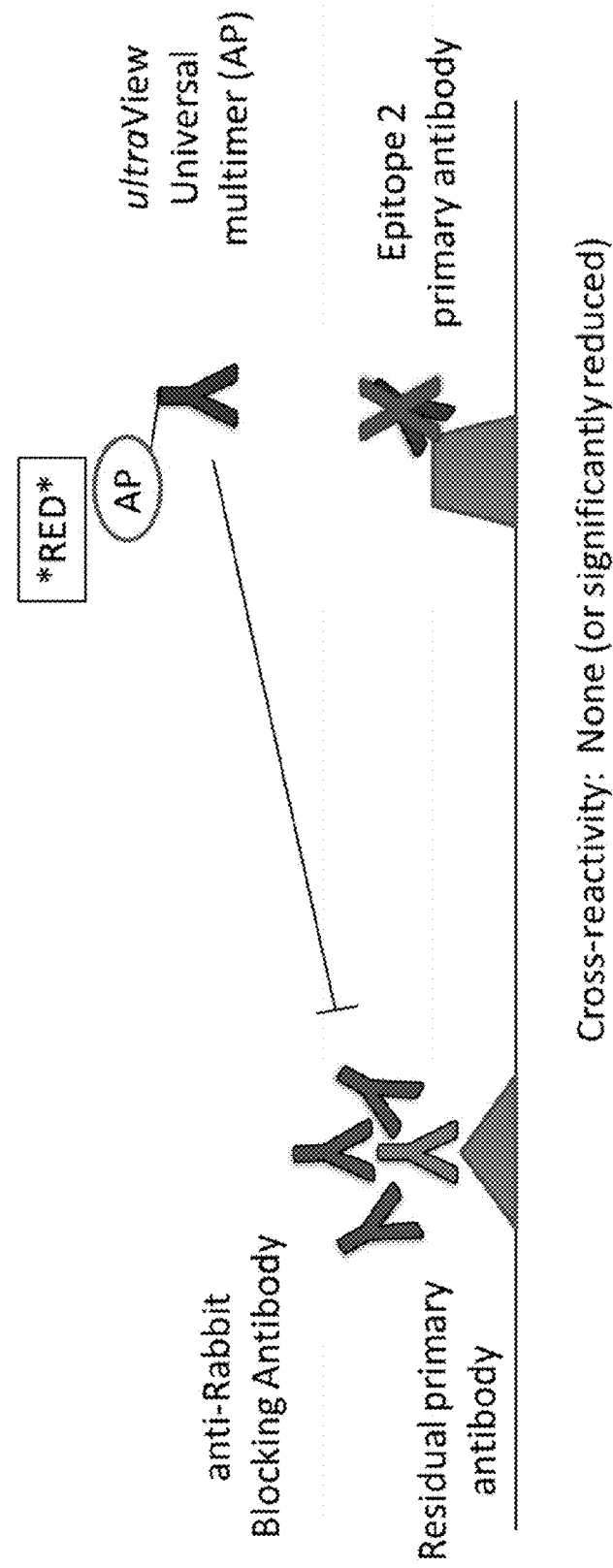

For example, as shown in FIG. 24A, the same sample or tissue section can be contacted with two different primary antibodies, which recognize different epitopes. Then using different secondary antibody detection systems, the signals due to the primary antibody can be distinguished. For example as shown in FIG. 24A, the first primary antibody (on the left) can be detected using an HQ-labeled secondary antibody, which is detected using an anti-HQ antibody labeled with HRP, which produces a detectable DAB signal. The second primary antibody (on the right) can be detected using an AP-labeled secondary antibody, which produces a detectable red signal. This system assumes though that the first and second primary antibodies are from different species (e.g., mouse and rabbit, respectively) and thus anti-mouse (Ms) secondary antibodies can be used in the first detection system, and anti-rabbit (Rb) secondary antibodies can be used in the second detection system. However, as shown in FIG. 24B, if both primary antibodies are from the same species (e.g., both rabbit antibodies), then undesirable cross reactivity can result between the secondary antibodies. The present application provides solutions to this problem. For example, as shown in FIG. 24C, after contacting the sample with the first primary antibody (and any secondary antibodies, not shown), the sample can be contacted with blocking antibodies and be subjected to denaturation (not shown) prior to contact with the second primary antibody. This reduces the available binding sites on the first primary antibody, and thus reduces cross-reactivity of the secondary antibody system used to detect the second primary antibody.

Multiple parameters were assessed. For example, the precision was confirmed by establishing reproducibility of staining across multiple runs on multiple instruments; specificity was demonstrated by recapitulating previously described tissue staining patterns and subcellular localizations in various specimens. The assay was applied to different tissue microarrays to evaluate applicability to head and neck, colorectal, and non-small cell lung cancer samples. In addition, thirty-five total whole tissue specimens and multi-tissue array cores of hepatocellular malignancies were examined to validate the assay for HCC. The staining data of the tissue microarrays as well as the whole tissue specimens reported herein give confidence in the use of this assay with tissues that express CD3 and CD16, such as head and neck, colorectal, HCC, and non-small cell lung carcinomas.

Based on these observations, provided herein are new methods and systems for detecting CD3 and CD16 proteins in a sample. Also provided are methods of scoring CD3 and CD16 in the sample, as well as using such information to predict whether a tumor will respond, or did respond, to an anti-EGFR therapy such as GA201.

Methods of Detecting CD3 and CD16 Proteins

Figure 25:
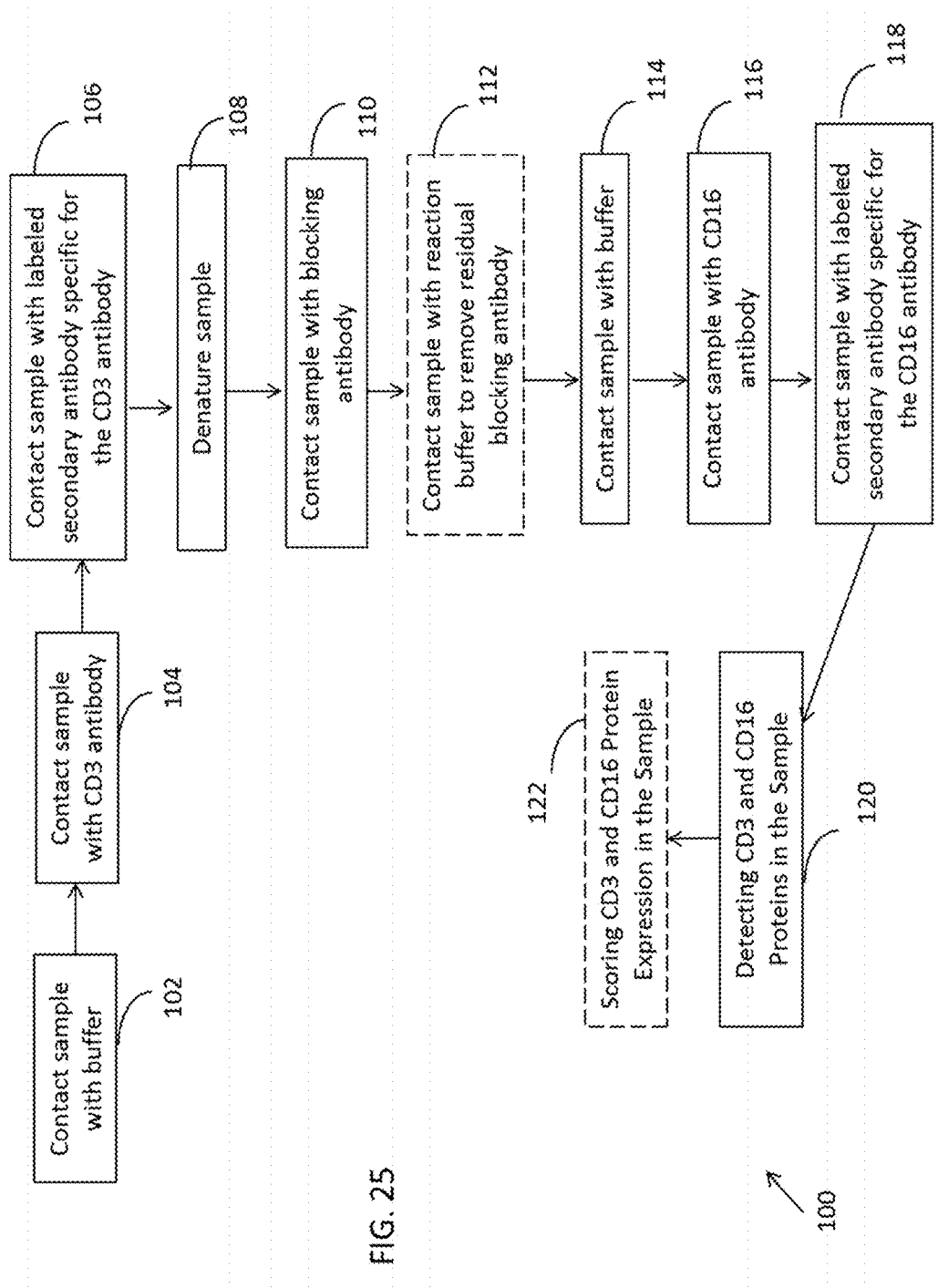
FIG. 25 is a flow chart an exemplary method 100 for analyzing CD3 and CD16 protein expression.

Provided herein are methods of detecting CD3 protein and CD16 protein in a sample. Such methods can be implemented at least in part by a computing system and/or automated instrumentation, such as using a suitably programmed computer. FIG. 25 is a flowchart of an exemplary method 100 of implementing detection of CD3 protein and CD16 protein and can be implemented, for example, in the system shown in FIG. 26. Although a particular order is shown in FIG. 25, one skilled in the art will appreciate that variations can be made. For example, in some examples the CD16 primary and secondary antibodies are contacted with the sample before the CD3 primary and secondary antibodies. In addition, the methods can include additional steps, such as additional washing or detection steps, as well as analysis of control samples (such as samples known to have or not have CD3 or CD16).

Referring to FIG. 25, the method 100 can include contacting the sample with a buffer 102, such as a buffer that can hydrolyze the covalent bonds formed by formalin in tissue. In one example, the buffer has a pH of about 8 to 9 (such as pH 8.2 to 8.7, pH 8.4 to 8.6, or pH 8.6), and includes Tris and a preservative (such as ProClin 5000 which contains the active ingredients 5-chloro-2-methyl-4-isothiazine-3-one and 2-methyl-4-isothiazolin-3-one). A specific example of the buffer used is cell conditioning 1 (CC1) (VMSI Catalog #950-124; Tris/Boric acid/EDTA, pH 8.6). The sample is incubated in the buffer for at least 30 minutes prior to contacting the sample with the first primary antibody (such as at least 35 minutes, at least 40 minutes, at least 45 minutes, or at least 50 minutes, for example 30-45 minutes, 38-42 minutes, 40 minutes, such as about 40 minutes). In some examples, this step is performed at a temperature above 37° C., such as at least 90° C., at least 95° C., or at least 100° C., such as about 100° C.

After incubating or contacting the sample with the buffer 102, the sample is contacted with a CD3 antibody 104. In one example the primary CD3 antibody is a rabbit monoclonal antibody, such as clone 2GV6 (VMSI Catalog No. 790-4341). The sample is incubated with the CD3 primary antibody for at least 3 minutes, such as at least 4, at least 5, at least 6, at least 7, at least 8, at least 9, at least 10, or at least 15 minutes, such as about 3, 4, 5, 6, 7, 8, 9, 10, 11, 12, 13, 14, 15, 16 or 20 minutes, such as 8 minutes. In some examples, the sample is incubated with the CD3 primary antibody at a temperature of about 37° C., such as 30-40° C., 35-38° C., such as 37° C. In a specific example, the sample is contacted with the CD3 antibody for 8 minutes at 37° C. In some examples, the CD3 antibody is clone 2GV6 (VMSI Catalog No. 790-4341) which is sold at a concentration of 0.4 µg/ml, which can be diluted to about 0.1 µg/ml on the slide. In some examples, the primary CD3 antibody is incubated with the sample in the presence of a reaction buffer (for example a Tris buffer at a pH of about 7.6+/−0.2, such as Ventana Medical Systems Inc., catalog #950-300).

After incubating or contacting the sample with the CD3 primary antibody 104, the sample is contacted with a labeled secondary antibody to permit detection of the CD3 antibody 106. In some examples, the sample is washed or rinsed prior to adding the secondary antibody to remove unbound CD3 primary antibody. For example, if the CD3 primary antibody is a rabbit antibody, a secondary antibody can be an anti-rabbit antibody, while if the CD3 primary antibody is a mouse antibody, the secondary antibody can be an anti-mouse antibody. The secondary antibody can be directly or indirectly labeled. In one example, the labeled secondary antibody that permits detection of the CD3 primary antibody includes an anti-rabbit-3-hydroxyquinoxaline-2-carboxylic acid (HQ) conjugate (or an anti-mouse-HQ conjugate) and an anti-HQ-HRP antibody. In such an example, the method further includes contacting the sample agents that permit detection of the HRP, such as contact with hydrogen peroxide in the presence of diaminobenzidine (DAB) and copper sulfate. One skilled in the art will appreciate that other labels and means of detection can be used. Such labeling permits detection of CD3 in the sample.

After incubating or contacting the sample with the labeled CD3 secondary antibody 106, the sample is incubated under denaturing conditions 108. For example, the sample can be incubated under denaturing conditions in order to denature or destroy CD3 primary antibody remaining on the slide. In some examples, the sample is denatured by incubating the sample at a temperature of at least 80° C., such as at least 90° C., at least 95° C., such as 80° C.-100° C., 90-100° C., or 92-98° C., for example about 95° C. In some examples, the sample is incubated at such a temperature for at least 5 minutes, such as at least 6, at least 7, at least 8, at least 9, at least 10, or at least 15 minutes, such as 5-15, 5-10, 6-9, or about 8 minutes. In a specific example, the sample is incubated at 95° C. for 8 minutes. In some examples, the denaturation is performed in the presence of a reaction buffer (for example a Tris buffer at a pH of about 7.6+/−0.2, such as Ventana Medical Systems Inc., catalog #950-300).

After denaturing the sample 108, the sample is contacted with a blocking antibody 110. This permits blocking of antigenic sites still available on the CD3 primary antibody, and reduces cross-reactivity with subsequent secondary antibodies (e.g., those used to detect CD16). For example, the blocking antibody can be a chicken anti-rabbit antibody if the CD3 primary antibody is a rabbit antibody, and the blocking antibody can be a chicken anti-mouse antibody if the CD3 primary antibody is a mouse antibody. The sample can be incubated with the blocking primary antibody for at least 10 minutes, such as at least 15, at least 16, at least 20, at least 25, at least 30, at least 31, at least 32, or at least 35 minutes (e.g., 20-40 minutes, 25-35 minutes, 30-34 minutes), such as about 25, 26, 27, 28, 29, 30, 31, 32, 33, 34, 35, 36, 37, 38, 39 or 40 minutes, such as 32 minutes. In some examples, the sample is incubated with the blocking antibody at a temperature of about 37° C., such as 30-40° C., 35-38° C., such as 37° C. In a specific example, the sample is contacted with the blocking antibody for 32 minutes at 37° C.

After contacting the sample with a blocking antibody 110, the sample can be optionally contacted with a reaction buffer to remove residual blocking antibody 112. The reaction buffer can be a Tris buffer, such as one having a pH of 7 to 8, such as 7.2-7.8 or about 7.6+/−0.2 (such as Ventana Medical Systems Inc., catalog #950-300). The sample can be incubated with the reaction buffer for at least 10 minutes, such as at least 15, at least 16, at least 20, at least 25, at least 30, at least 31, at least 32, or at least 35 minutes (e.g., 20-40 minutes, 25-35 minutes, 30-34 minutes), such as about 25, 26, 27, 28, 29, 30, 31, 32, 33, 34, 35, 36, 37, 38, 39 or 40 minutes, such as 32 minutes. In some examples, the sample is incubated with the reaction buffer at a temperature of about 37° C., such as 30-40° C., 35-38° C., such as 37° C. In a specific example, the sample is contacted with the reaction buffer for 32 minutes at 37° C.

After contacting the sample with a blocking antibody 110, or after contacting the sample with a reaction buffer 112 the sample can be contacted with a buffer 114, for example to provide conditioning for the CD16 primary antibody. In one example, the buffer has a pH of about 8 to 9 (such as pH 8.2 to 8.7, pH 8.4 to 8.6, or pH 8.6), and includes Tris and a preservative (such as ProClin 5000 which contains the active ingredients 5-chloro-2-methyl-4-isothiazine-3-one and 2-methyl-4-isothiazolin-3-one). A specific example of the buffer used is cell conditioning 1 (CC1) (VMSI Catalog #950-124; Tris/Boric acid/EDTA, pH 8.6). The reaction buffer can be used to provide enough liquid on the slide and to maintain a desired volume (e.g., 600 μl).

After incubating or contacting the sample with the buffer 114, the sample is contacted with a CD16 antibody 116. In one example the CD16 primary antibody is a rabbit monoclonal antibody, such as Spring Bioscience Catalog # No. M475 clone SP175. The sample is incubated with the CD16 primary antibody for at least 5 minutes, such as at least 6, at least 7, at least 8, at least 9, at least 10, at least 11, at least 12, at least 13, at least 14, at least 15, at least 16, at least 17, at least 18, at least 19, at least 20, at least 22, at least 25, or at least 30 minutes, such as about 8, 9, 10, 11, 12, 13, 14, 15, 16, 17, 18, 19, 20, 21, 22, 23, 24, 25, 26, 27, 28, 29, or 30 minutes, such as 10-20, 12-18, 15-17, or 16 minutes. In some examples, the sample is incubated with the CD16 primary antibody at a temperature of about 37° C., such as 30-40° C., 35-38° C., such as 37° C. In a specific example, the sample is contacted with the CD16 antibody for 16 minutes at 37° C. In some examples, the CD16 antibody is Spring Bioscience Catalog # No. M475 clone SP175, which is provided at a concentration of 0.136 μg/ml, which can be diluted to about 0.034 μg/ml on the slide. In some examples, the primary CD16 antibody is incubated with the sample in the presence of a reaction buffer (for example a Tris buffer at a pH of about 7.6+/−0.2, such as Ventana Medical Systems Inc., catalog #950-300).

After incubating or contacting the sample with the CD16 primary antibody 116, the sample is contacted with a labeled secondary antibody to permit detection of the CD16 antibody 118. In some examples, the sample is washed or rinsed prior to adding the secondary antibody to remove unbound CD16 primary antibody. For example, if the CD16 primary antibody is a rabbit antibody, a secondary antibody can be an anti-rabbit antibody, while if the CD16 primary antibody is a mouse antibody, the secondary antibody can be an anti-mouse antibody. The secondary antibody can be directly or indirectly labeled. In one example, the labeled secondary antibody that permits detection of the CD16 primary antibody includes an anti-rabbit-alkaline phosphatase (AP) multimer or an anti-mouse-AP multimer. In such an example, the method further includes contacting the sample with agents that permit detection of the AP, such as contact with napthol in the presence of alkaline phosphatase enhancer and fast red. One skilled in the art will appreciate that other labels and means of detection can be used. Such labeling permits detection of CD16 in the sample.

After labeling the sample with the antibodies that permit detection of the CD3 and CD16 antibodies, the sample is analyzed to detect CD3 and CD16 proteins in the sample 120. For example, it can be determined that that CD3 protein is present in the sample if the labeled secondary antibody to permit detection of the CD3 antibody is detected and it can be determining that CD16 protein is present in the sample if the labeled secondary antibody to permit detection of the CD16 antibody is detected. In some examples, the method includes determining the specific localization of CD3 and CD16. In some examples, the method includes determining how many cells are positive for CD3 and/or CD16 staining. In some examples, the signal from the CD3 and/or CD16 proteins are quantified. In some examples, microscopy, such as light or fluorescence microscopy, is used to detect the staining patterns. In some examples, an output showing an image with the CD3 and/or CD16 staining is provided (such as a digital image displayed on a screen).

Positive and negative controls can be stained at the same time as test samples, to verify satisfactory performance of IHC assays. The positive control can be selected based on a pattern of CD3/CD16 expression that is likely to reflect staining patterns in clinical trial specimens. A non-small cell lung cancer specimen—such as the one used herein, which has moderate to strong CD3/CD16 staining intensity—is an example of a positive control. Negative controls ensure absence of non-specific staining, and can also be used to compare background between different lots of antibody. In one example, the negative control is normal epithelial tissue, such as one found in a NSCLC specimen. A single specimen with positive and negative regions may be used as a dual control.

A. Detection of Proteins

In particular embodiments, a sample is analyzed to determine if it contains detectable CD3 and CD16, such as detectable levels of CD3 and CD16 proteins in one or more tumor cells. Thus, the sample can be analyzed to detect or measure the presence of CD3 and CD16 protein in the sample, for example a qualitative or semi-quantitative measurement. In particular embodiments, the disclosed methods utilize quantitative measurement of the presence of CD3 and CD16 protein in tumor cells in the sample.

IHC can be used to detect or measure CD3 and CD16 protein present in a sample from the subject. IHC can determine the presence or distribution of an antigen (such as a protein) in a sample (such as a tumor sample, for example, a portion or section of tissue including CD3 and/or CD16-expressing tumor cells or tissue) by detecting interaction of the antigen with a specific binding agent, such as an antibody or aptamer. A sample including an antigen (such as CD3 and/or CD16) is incubated with a CD3- or CD16-specific antibody under conditions permitting antibody-antigen binding. In some examples, both primary antibodies for CD3 and CD16 are from the same host species (e.g., both are rabbit antibodies, or both are mouse antibodies). Antibody-antigen binding can be detected by means of a detectable label conjugated to the antibody (direct detection) or by means of a detectable label conjugated to a secondary antibody, which is raised against the primary antibody (e.g., indirect detection). In other examples of indirect detection, antibody-antigen binding is detected by means of a detectable label conjugated to a tertiary antibody which is capable of binding to a secondary antibody (e.g., is raised against the secondary antibody or is raised against a molecule conjugated to the secondary antibody, such as a hapten). Exemplary detectable labels that can be used for IHC include, but are not limited to, radioactive isotopes, fluorochromes (such as fluorescein, fluorescein isothiocyanate, and rhodamine), haptens, enzymes (such as horseradish peroxidase or alkaline phosphatase), and chromogens (such as 3,3'-diaminobenzidine (DAB) or Fast Red). In some examples, detection of antigen-antibody binding also includes signal amplification (such as tyramide signal amplification or related methods). The signal amplification method may include methods described in U.S. Pat. Publ. No. 2012/0171668, incorporated by reference herein in its entirety.

In some examples, the CD3 or CD16 specific binding agent is an antibody, such as a polyclonal or monoclonal antibody, or fragment thereof. In some examples, the CD3 or CD16 antibody is a humanized antibody. In some examples, the CD3 or CD16 antibody is a chimeric antibody. The CD3 and CD16 antibodies can be detected with an appropriate labeled secondary antibody. In additional examples, the CD3 and CD16 antibodies are detected with an appropriate labeled tertiary antibody.

Primary antibodies that can be used to detect CD3 and CD16 expression are known. Particular non-limiting examples include those listed in Tables 1 and 3, as well as: CD3 antibodies from abcam, Cambridge, Mass. (e.g., catalog # ab5690), Novus Biologicals, Littleton, Colo. (e.g., catalog #NBP1-72167), and Santa Cruz Biotechnology, Dallas, Tex. (e.g., catalog # sc-20919) and CD16 antibodies from abcam, Cambridge, Mass. (e.g., catalog # ab94773), and Santa Cruz Biotechnology, Dallas, Tex. (e.g., catalog # sc-sc-20627). However, a person of ordinary skill in the art will appreciate that other antibodies can be used in the methods provided herein, including those now available or developed in the future. For example, methods of preparing antibodies against a specific target protein are well known in the art. A CD3 or CD16 protein or a fragment or conservative variant thereof can be used to produce antibodies which are immunoreactive or specifically bind to an epitope of the CD3 or CD16 protein. Polyclonal antibodies, antibodies which consist essentially of pooled monoclonal antibodies with different epitopic specificities, as well as distinct monoclonal antibody preparations are included. The preparation of polyclonal antibodies is well known to those skilled in the art. See, for example, Green et al., "Production of Polyclonal Antisera," in: *Immunochemical Protocols*, pages 1-5, Manson, ed., Humana Press, 1992; Coligan et al., "Production of Polyclonal Antisera in Rabbits, Rats, Mice and Hamsters," in: *Current Protocols in Immunology*, section 2.4.1, 1992. The preparation of monoclonal antibodies likewise is conventional (see, for example, Kohler & Milstein, Nature 256:495, 1975; Coligan et al., sections 2.5.1-2.6.7; and Harlow et al. in: *Antibodies: a Laboratory Manual*, page 726, Cold Spring Harbor Pub., 1988).

In some examples, a sample is obtained from a subject (such as a tumor sample that is known or suspected of overexpressing CD3 or CD16, such as an colorectal cancer, head and neck cancer, or lung cancer), and processed for IHC. For example, the sample can be fixed and embedded, for example with formalin and paraffin. The sample can then be mounted on a support, such as a glass microscope slide. For example, the sample can be sliced into a series of thin sections (for example, using a microtome), and the sections mounted onto a microscope slide. In some examples, a single slide includes multiple tissue sections from the same cancer sample or sections from the same cancer sample can be placed on different slides. In some examples, one section of the sample is stained with multiple markers, such as CD3 and CD16 antibodies. In other examples, different sections of the cancer (e.g., NSCLC tumor) sample can then be individually labeled with different antibodies, for example an anti-CD3 antibody, an anti-CD16 antibody, or a negative control antibody (for example, an antibody that does not specifically bind to an endogenous antigen in the sample). That is, one section can be labeled with an anti-CD3 antibody, another section can be labeled with an anti-CD16 antibody, and yet another section can be labeled with a negative control antibody (such as an antibody that binds to a target that does not occur endogenously in the sample). In some examples, a separate slide from the same subject is stained with H&E (such as an adjacent or serial section from the same tumor sample). In some examples, additional proteins of interest can be detected in the same or additional tissue samples by labeling with further antibodies (for example other tumor markers, such as anti-EGFR antibodies). In some examples, an automated slide stainer (such as BENCHMARK instruments from Ventana Medical Systems, for example BENCHMARK XT or BENCHMARK GX instruments) can be used to stain and process the slides.

In some examples, detecting CD3 and CD16 protein in the sample includes indirect detection of binding of the CD3 and CD16 antibodies to the sample (for example, the CD3 or CD16 (primary) antibody is not detectably labeled). For example, the sample is contacted with anti-CD3 or anti-CD16 antibodies (such as those listed in Table 3) under conditions sufficient for the CD3 or CD16 antibody to bind to CD3 or CD16 proteins, respectively, in the sample. The sample is then contacted with secondary antibodies that can specifically bind to the CD3 or CD16 antibody (such as an anti-rabbit antibody, if the CD3 antibody is a rabbit antibody or an anti-mouse antibody, if the CD3 antibody is a mouse antibody) under conditions sufficient for the secondary antibody to bind to the CD3 or CD16 antibody. The secondary antibody can be detectably labeled. The detectable label can be conjugated to the secondary antibody. In some examples, the detectable label conjugated to the secondary antibody can be directly detected (such as a fluorescent label, or an enzyme, which can produce a detectable reaction product in the presence of suitable substrate). In other examples, the secondary antibody is conjugated to one or more haptens (such as fluorescein, dinitrophenyl, biotin, or 3-hydroxyquinoxaline-2-carboxylic acid (HQ)). The sample is then contacted with a tertiary antibody that can specifically bind the hapten-conjugated secondary antibody (for example, an anti-hapten antibody, such as an anti-HQ antibody) under conditions sufficient for the tertiary antibody to bind to the hapten. In some examples, the tertiary antibody is conjugated to a detectable label, such as an enzyme (for example, horseradish peroxidase (HRP) or alkaline phosphatase (AP)). The sample is then contacted with one or more reagents that produce a detectable reaction product in the presence of the enzyme. In some examples, the sample is contacted with an HRP substrate (such as hydrogen peroxide) and a chromogen (such as DAB) that produces a visually detectable product in the presence of HRP. In some examples, detecting CD3 and CD16 protein in the sample is carried out using the OPTIVIEW DAB IHC Detection Kit (Ventana Medical Systems, Inc., Tucson, Ariz., Catalog No. 760-700) or the ultraView Detection Kit (Ventana Medical Systems, Inc., Tucson, Ariz., Catalog No. 760-500).

In particular embodiments, detecting CD3 and/or CD16 protein in the sample includes indirect detection including signal amplification. In some examples, signal amplification allows unequivocal detection of CD3 and/or CD16 positive specimens which may exhibit only weak staining without signal amplification. Signal amplification methods for IHC are known to one of ordinary skill in the art. In some examples, signal amplification includes CAtalyzed Reporter Deposition (CARD), also known as Tyramide Signal Amplification (TSA™). In one variation of this method an enzyme-conjugated secondary antibody (such as an HRP-conjugated secondary antibody) binds to the primary antibody. Next a substrate of biotinylated tyramide (tyramine is 4-(2-aminoethyl)phenol) is used, which presumably becomes a free radical when interacting with the HRP enzyme. The phenolic radical then reacts quickly with the surrounding material, thus depositing or fixing biotin in the vicinity. This process is repeated by providing more substrate (biotinylated tyramide) and building up more localized biotin. Finally, the "amplified" biotin deposit is detected with streptavidin attached to a fluorescent molecule. Alternatively, the amplified biotin deposit can be detected with avidin-peroxidase complex, which is then contacted with DAB to produce a brown color.

In other examples, signal amplification includes contacting the sample with hydrogen peroxide and a tyramide-HQ conjugate after contacting the sample with an HRP-conjugated tertiary antibody under conditions sufficient for depositing HQ at or near the site of the primary antibody bound to the sample. The sample is then contacted with an enzyme-conjugated antibody (such as an HRP- or AP-conjugated antibody) that specifically binds to HQ. In some examples, this enzyme-conjugated antibody is the same as the HRP-conjugated tertiary antibody. In other examples, the enzyme-conjugated antibody is a different antibody than the HRP-conjugated tertiary antibody. The sample is then contacted with one or more reagents that produce a detectable reaction product in the presence of the enzyme. In some examples, the sample is contacted with an HRP substrate (such as hydrogen peroxide) and a chromogen (such as DAB) that produces a visually detectable product in the presence of HRP. In some examples, signal amplification is carried out using OPTIVIEW Amplification Kit (Ventana Medical Systems, Inc., Tucson, Ariz., Catalog No. 760-099).

B. Samples

In some examples, the disclosed methods include the step of obtaining a sample, preparing the sample for analysis (for example fixing the sample, contacting it with CD3 and CD16 antibodies, H&E staining or combinations thereof), or both. Methods of obtaining a biological sample from a subject are known in the art. For example, methods of obtaining tissue, such as normal or cancerous lung tissue, ovarian tissue, pancreatic tissue, mesothelial tissue, colon or other gi tissue, head and neck tissue, breast tissue, liver tissue, kidney tissue, skin tissue, prostate tissue, uterine tissue, bone, brain tissue, lung cells, ovarian cells, pancreatic cells or mesothelial cells, colon cells, head and neck cells, breast cells, liver cells, kidney cells, skin cells, prostate cells, uterine cells, bone cells, brain cells, and lung cells are routine. For example, a sample from a lung, ovary, liver, or pancreas, or other tumor that contains cellular material, can be obtained by surgical excision of all or part of the tumor, by collecting a fine needle aspirate from the tumor, as well as other methods known in the art.

In some examples, the sample is obtained from a subject having or suspected to have cancer, such as lung cancer (such as NSCLC), colorectal cancer, HCC, or head and neck cancer. Other exemplary tumors that can be analyzed with the disclosed methods and systems include hematological tumors and solid tumors. Examples of hematological tumors include leukemias, including acute leukemias (such as acute lymphocytic leukemia, acute myelocytic leukemia, acute myelogenous leukemia and myeloblastic, promyelocytic, myelomonocytic, monocytic and erythroleukemia), chronic leukemias (such as chronic myelocytic (granulocytic) leukemia, chronic myelogenous leukemia, and chronic lymphocytic leukemia), polycythemia vera, lymphoma, Hodgkin's disease, non-Hodgkin's lymphoma (indolent and high grade forms), multiple myeloma, Waldenstrom's macroglobulinemia, heavy chain disease, myelodysplastic syndrome, hairy cell leukemia and myelodysplasia. Examples of solid tumors, such as sarcomas and carcinomas, include fibrosarcoma, myxosarcoma, liposarcoma, chondrosarcoma, osteogenic sarcoma, and other sarcomas, synovioma, mesothelioma, Ewing's tumor, leiomyosarcoma, rhabdomyosarcoma, colon carcinoma, lymphoid malignancy, pancreatic cancer, breast cancer, lung cancers (such as non-small cell lung cancer), ovarian cancer, prostate cancer, squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, and CNS tumors (such as a glioma, astrocytoma, medulloblastoma, craniopharyogioma, ependymoma, pinealoma, hemangioblastoma, acoustic neuroma, oligodendroglioma, menangioma, melanoma, neuroblastoma and retinoblastoma). Thus, a sample can be obtained from any such tumor.

In particular examples, the sample obtained from the subject includes tumor cells, such as at least a portion of a tumor. In some examples, the sample from the subject also includes normal (e.g., non-tumor) tissue or cells. In some examples, the tumor sample is placed in 10% neutral buffered formalin upon removal from the subject.

The sample can be fresh, frozen, or fixed. In some examples, samples are processed post-collection by fixation and in some examples are wax- (e.g., paraffin-) embedded. Fixatives for mounted cell and tissue preparations are well known in the art and include, without limitation, formalin fixative, 95% alcoholic Bouin's fixative; 95% alcohol fixative; B5 fixative, Bouin's fixative, Karnovsky's fixative (glutaraldehyde), Hartman's fixative, Hollande's fixative, Orth's solution (dichromate fixative), and Zenker's fixative (see, e.g., Carson, *Histotechology: A Self-Instructional Text*, Chicago:ASCP Press, 1997). Staining intensity may vary depending on the particular fixatives (such as 95% alcohol, AFA, B5, or Prefer) used. In particular examples, the sample is fixed in neutral buffered formalin (such as 10% neutral buffered formalin) or zinc formalin. In some examples, the sample is fixed for at least about 6 hours (for example, about 6-48 hours, 12-24 hours or about 6, 12, 16, 18, 24, 36, or 48 hours). In additional examples, the sample is placed in fixative within about 6 hours of collection (for example, within about 15 minutes, 30 minutes, 1, 2, 3, 4, 5, or 6 hours).

In some examples, the sample can be a fixed, wax-embedded tissue sample, such as a fixed, wax-embedded tissue sample including tumor cells. In some examples, the sample is a tissue section including tumor cells labeled with a primary antibody specific for CD3 and with a primary antibody specific for CD16, which may be labeled directly or indirectly (e.g., with a labeled secondary antibody), which in some examples is further stained with H&E (e.g., using an adjacent or serial section from the same sample).

In some examples, the sample (or a fraction thereof) is present on a solid support. Solid supports bear the biological sample and permit the convenient detection of components (e.g., proteins) in the sample. Exemplary supports or substrates include microscope slides (e.g., glass microscope slides or plastic microscope slides), coverslips (e.g., glass coverslips or plastic coverslips), tissue culture dishes, multi-well plates, membranes (e.g., nitrocellulose or polyvinylidene fluoride (PVDF)) or BIACORE™ chips.

C. Scoring CD3 Protein and CD16 Protein Expression

Figure 27A:
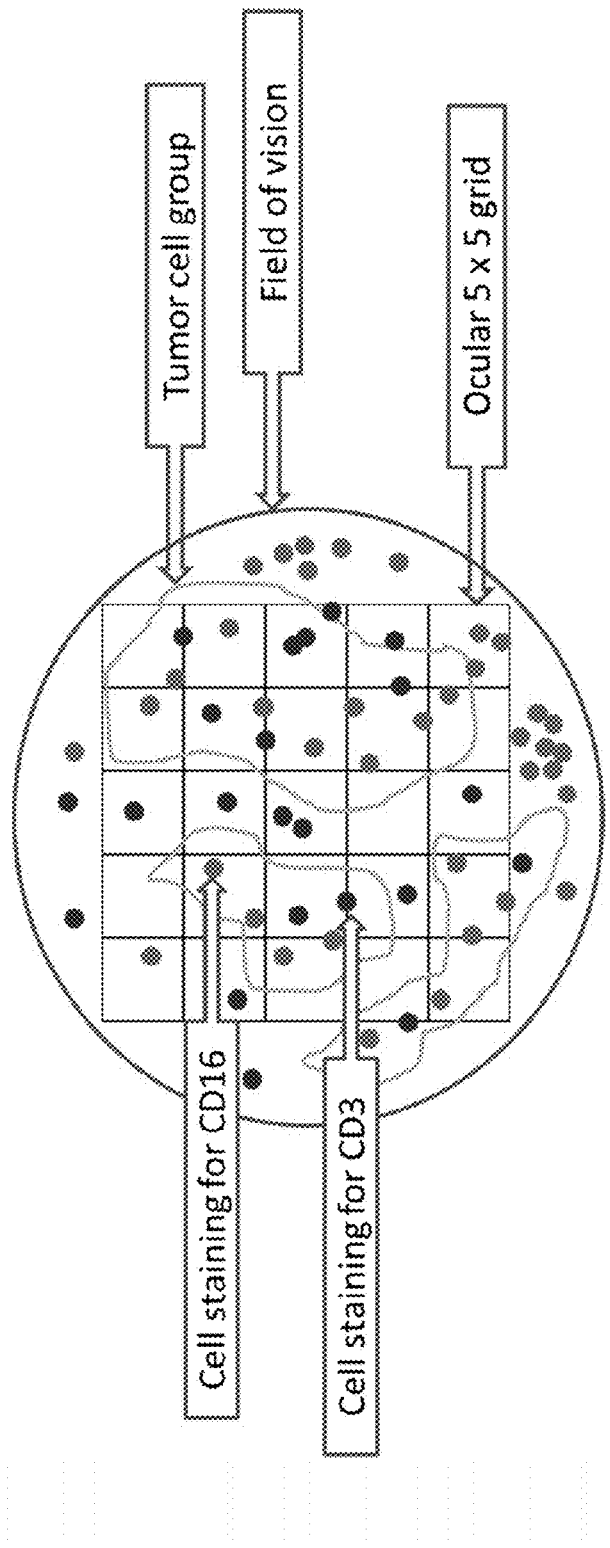
Figure 28A:
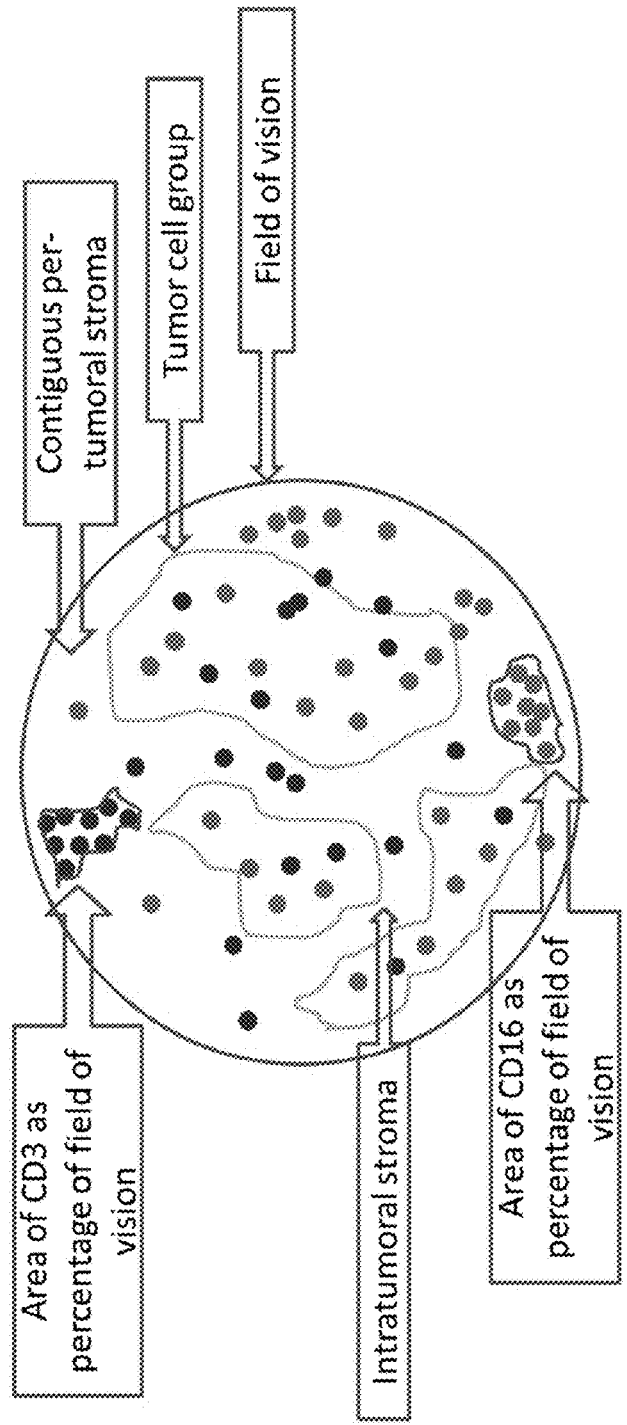

In some examples, the disclosed methods can include scoring the CD3 and CD16 protein detected in the sample (FIG. 25, 122). Examples are shown in FIGS. 27A-27B and 28A-28B. In a first example (FIGS. 27A and 27B), if the sample analyzed is a tumor sample, scoring the presence of CD3 protein and CD16 protein can include determining an absolute number of cells (such as immune cells that infiltrate the tumor) staining with the CD3 antibody in the sample using a 5×5 ocular grid with an area of 0.25 square millimeter, determining an absolute number of cells (such as immune cells that infiltrate the tumor) staining with the CD16 antibody in the sample using a 5×5 ocular grid with an area of 0.25 square millimeter, extrapolating the absolute number of cells staining with the CD3 antibody to a number of cells in a 1 square millimeter region, and extrapolating the absolute number of cells staining with the CD16 antibody to a number of cells in a 1 square millimeter region, thereby generating a score of CD3 protein and CD16 protein. Thus, the method can include counting the number of cells staining positive for CD3 and the number of cells staining positive for CD16 in the grid (such as CD3 and/or CD16 positive cells, such as immune cells that infiltrate the tumor). In one specific example, those values are inserted into the following formula: cell count/(0.0156×# of grids). This formula is dependent on the diameter of the objective which is variable between models even with equal magnification. Other formulas can be used if a different magnification or a different objective is used. In some examples, randomly selected regions of the sample containing the tumor are selected for scoring. Thus, as shown in FIG. 27A, each brown and red dot in the diagram represents cells staining with CD3 and CD16, respectively. Each cell with either CD3 or CD16 staining is counted. With this grid method, if the cells staining for CD3 or CD16 are in stroma, they are not counted; it includes only cells amongst the tumor cells.

In a second example (FIGS. 28A-28B), if the sample analyzed is a tumor sample, scoring the presence of CD3 protein and CD16 protein can include determining the area of staining with the CD3 antibody and the CD16 antibody in the intratumoral and contiguous peri-tumoral regions of the sample (e.g., intratumoral and contiguous peritumoral stroma), dividing the area of staining with the CD3 antibody in the intra-tumoral region and contiguous peri-tumoral stroma by the area of total stroma (e.g., in the field of vision), thereby generating a score of CD3 protein for the stroma, and dividing the area of staining with the CD16 antibody in the intra-tumoral and contiguous peri-tumoral stroma by the area of total stroma (e.g., in the field of vision), thereby generating a score of CD16 protein for the stroma.

In some examples, combinations of the first and second examples are used.

In some examples, scoring includes manual or automated scoring of CD3 and CD16 staining. In some examples, a modified H score (discussed below) or a percentage of each marker are used as the scoring method.

D. Methods of Prognosis

The disclosed embodiments can further include identifying and/or selecting subjects for treatment with an EGFR-targeted therapy (such as an anti-EGFR targeted therapy, for example GA201). For example, if the tumor sample obtained from the subject is analyzed or scored using the methods provided herein as having an increased CD3 and/or CD16 score relative to a normal sample (e.g., non-tumor sample of the same tissue type), the subject can be identified or selected as one having a tumor that will respond to the anti-EGFR therapy. For example, an increase of at least 20%, at least 40%, at least 50%, at least 75%, at least 80%, at least 90%, at least 100%, at least 200% or at least 500% (such as an increase of at least 2-fold, at least 5-fold, or at least 10-fold) in CD3 and/or CD16 expression or score in the tumor sample as compared to the CD3 and/or CD16 expression or score in a normal sample (such as a reference value or range of values for such a sample), indicates the tumor will respond to the anti-EGFR therapy. In contrast, if the tumor sample obtained from the subject is analyzed or scored using the methods provided herein as having a similar or decreased CD3 and/or CD16 score relative to a normal sample (e.g., non-tumor sample), the subject can be identified or selected as one having a tumor that will respond to the anti-EGFR therapy. For example, a difference of no more than 15%, no more than 10%, no more than 5%, no more than 1%, or no more than 0.5% (such as a difference of no more than 0.01-15%) in CD3 and/or CD16 expression or score in the tumor sample as compared to the CD3 and/or CD16 expression or score in a normal sample (such as a reference value or range of values for such a sample), indicates the tumor will not respond to the anti-EGFR therapy. In some examples, the disclosed methods can further include administering one or more EGFR-targeted therapies to the subject if the subject is identified or selected as one having a tumor that will respond to the anti-EGFR therapy. In contrast, if the subject is identified as one who will not likely benefit from treatment with an EGFR-targeted therapy, the methods can further include administering other non-EGFR-targeted therapies to the subject.

Also provided are methods of method of determining the likelihood that a tumor will respond to an EGFR targeted therapy (for example GA201). For example, if the tumor sample obtained from the subject is analyzed or scored using the methods provided herein as having an increased CD3 and/or CD16 score relative to a normal sample (e.g., non-tumor sample of the same tissue type), this indicates the tumor will respond to the anti-EGFR therapy. For example, an increase of at least 20%, at least 40%, at least 50%, at least 75%, at least 80%, at least 90%, at least 100%, at least 200% or at least 500% (such as an increase of at least 2-fold, at least 5-fold, or at least 10-fold) in CD3 and/or CD16 expression or score in the tumor sample as compared to the CD3 and/or CD16 expression or score in a normal sample (such as a reference value or range of values for such a sample), indicates the tumor will respond to the anti-EGFR therapy. In contrast, if the tumor sample obtained from the subject is analyzed or scored using the methods provided herein as having a similar or decreased CD3 and/or CD16 score relative to a normal sample (e.g., non-tumor sample), this indicates the tumor will not respond to the anti-EGFR therapy. For example, a difference of no more than 15%, no more than 10%, no more than 5%, no more than 1%, or no more than 0.5% (such as a difference of no more than 0.01-15%) in CD3 and/or CD16 expression or score in the tumor sample as compared to the CD3 and/or CD16 expression or score in a normal sample (such as a reference value or range of values for such a sample), indicates the tumor will not respond to the anti-EGFR therapy.

Also provided are methods of method of determining whether a tumor has responded to an EGFR targeted therapy (for example GA201). For example, if the tumor sample obtained from the subject is analyzed or scored using the methods provided herein as having an increased CD3 and/or CD16 score relative to a normal sample (e.g., non-tumor sample of the same tissue type), this indicates the tumor did not respond to the anti-EGFR therapy. For example, an increase of at least 20%, at least 40%, at least 50%, at least 75%, at least 80%, at least 90%, at least 100%, at least 200% or at least 500% (such as an increase of at least 2-fold, at least 5-fold, or at least 10-fold) in CD3 and/or CD16 expression or score in the tumor sample as compared to the CD3 and/or CD16 expression or score in a normal sample (such as a reference value or range of values for such a sample), indicates the tumor did not respond to the anti-EGFR therapy. In contrast, if the tumor sample obtained from the subject is analyzed or scored using the methods provided herein as having a similar or decreased CD3 and/or CD16 score relative to a normal sample (e.g., non-tumor sample), this indicates the tumor responded to the anti-EGFR therapy. For example, a difference of no more than 15%, no more than 10%, no more than 5%, no more than 1%, or no more than 0.5% (such as a difference of no more than 0.01-15%) in CD3 and/or CD16 expression or score in the tumor sample as compared to the CD3 and/or CD16 expression or score in a normal sample (such as a reference value or range of values for such a sample), indicates the tumor responded to the anti-EGFR therapy.

1. Exemplary EGFR-Targeted Therapies

EGFR-targeted therapies include therapeutic agents that when administered in therapeutically effective amounts induce the desired response (e.g., by reducing the size or volume of the tumor, or reducing the size, volume or number of metastases). In one example, EGFR-targeted therapies include EGFR-specific binding agents that bind with higher affinity to EGFR proteins or nucleic acids, than to other molecules. For example, an EGFR specific binding agent can be one that binds with high affinity to EGFR, but does not substantially bind to another gene or gene product. Examples of EGFR specific binding agents include antisense compounds (such as antisense oligonucleotides, siRNAs, miRNAs, shRNAs and ribozymes), antibodies, aptamers, aptazymes, ligands, recombinant proteins, and peptide mimetics. In some examples, such binding agents can be attached to other therapeutic molecules, such as a toxin, thereby killing the cell targeted by the specific binding agent.

In one example, an EGFR-targeted therapy increases killing of CD3 and CD16-expressing tumor cells (or reduces their viability). Such killing need not result in 100% reduction tumor cells; for example EGFR-targeted therapies that result in reduction in the number of viable tumor cells by at least 10%, at least 20%, at least 30%, at least 40%, at least 50%, at least 75%, at least 90%, or at least 95% (for example as compared to no treatment with the EGFR-targeted therapy) can be used in the methods provided herein. For example, the EGFR-targeted therapy can reduce the growth of tumor cells by at least 10%, at least 20%, at least 30%, at least 40%, at least 50%, at least 75%, at least 90%, or at least 95% (for example as compared to no treatment with the EGFR-targeted therapy).

In one example, an EGFR-targeted therapy decreases CD3 and/or CD16 expression or activity. Such inhibition need not result in 100% reduction of CD3 and/or CD16 expression or activity; for example EGFR-targeted therapies that result in reduction in CD3 and/or CD16 expression or activity by at least 10%, at least 20%, at least 30%, at least 40%, at least 50%, at least 75%, at least 90%, or at least 95% (for example as compared to no treatment with the EGFR-targeted therapy) can be used in the methods provided herein. For example, the EGFR-targeted therapy can interfere with gene expression (transcription, processing, translation, post-translational modification), such as, by interfering with the CD3 and/or CD16's mRNA and blocking translation of the gene product or by post-translational modification of a gene product, or by causing changes in intracellular localization.

2 Administration of EGFR-Targeted Therapy and Other Agents

In some examples, the disclosed methods include providing a therapeutically effective amount of one or more EGFR-targeted therapies to a subject having an elevated level of CD3 and/or CD16 protein in their tumor. Methods and therapeutic dosages of such agents and treatments are known to those of ordinary skill in the art, and for example, can be determined by a skilled clinician. In some examples, the disclosed methods further include providing surgery, radiation therapy, and/or chemotherapeutics to the subject in combination with the EGFR-targeted therapy (for example, sequentially, substantially simultaneously, or simultaneously). Administration can be accomplished by single or multiple doses. Methods and therapeutic dosages of such agents and treatments are known to those skilled in the art, and can be determined by a skilled clinician. The dose required will vary from subject to subject depending on the species, age, weight and general condition of the subject, the particular therapeutic agent being used and its mode of administration.

Therapeutic agents, including EGFR-targeted therapies, can be administered to a subject in need of treatment using any suitable means known in the art. Methods of administration include, but are not limited to, intradermal, transdermal, intramuscular, intraperitoneal, parenteral, intravenous, subcutaneous, vaginal, rectal, intranasal, inhalation, oral, or by gene gun. Intranasal administration refers to delivery of the compositions into the nose and nasal passages through one or both of the nares and can include delivery by a spraying mechanism or droplet mechanism, or through aerosolization of the therapeutic agent.

Administration of the therapeutic agents, including EGFR-targeted therapies, by inhalant can be through the nose or mouth via delivery by spraying or droplet mechanisms. Delivery can be directly to any area of the respiratory system via intubation. Parenteral administration is generally achieved by injection. Injectables can be prepared in conventional forms, either as liquid solutions or suspensions, solid forms suitable for solution of suspension in liquid prior to injection, or as emulsions. Injection solutions and suspensions can be prepared from sterile powders, granules, and tablets. Administration can be systemic or local.

Therapeutic agents, including EGFR-targeted therapies, can be administered in any suitable manner, for example with pharmaceutically acceptable carriers. Pharmaceutically acceptable carriers are determined in part by the particular composition being administered, as well as by the particular method used to administer the composition. Accordingly, there is a wide variety of suitable formulations of pharmaceutical compositions of the present disclosure. The pharmaceutically acceptable carriers (vehicles) useful in this disclosure are conventional. *Remington's Pharmaceutical Sciences*, by E. W. Martin, Mack Publishing Co., Easton, Pa., 15th Edition (1975), describes compositions and formulations suitable for pharmaceutical delivery of one or more therapeutic agents Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Formulations for topical administration can include ointments, lotions, creams, gels, drops, suppositories, sprays, liquids and powders. Conventional pharmaceutical carriers, aqueous, powder or oily bases, thickeners and the like may be necessary or desirable.

Therapeutic agents, including EGFR-targeted therapies, for oral administration include powders or granules, suspensions or solutions in water or non-aqueous media, capsules, sachets, or tablets. Thickeners, flavorings, diluents, emulsifiers, dispersing aids or binders may be desirable.

Therapeutic agents, including EGFR-targeted therapies, can be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

In some examples, for example if the subject is identified as one having a tumor that will not respond to an EGFR-targeted therapy, such subjects can be treated with non-EGFR cancer treatments (such as surgery, radiation therapy, and/or chemotherapy). In one example, the therapy includes one or more anti-tumor pharmaceutical treatments which can include radiotherapeutic agents, anti-neoplastic chemotherapeutic agents, antibiotics, alkylating agents and anti-oxidants, kinase inhibitors, and other agents. Particular examples of other therapeutic agents that can be used include alkylating agents, such as nitrogen mustards (for example, chlorambucil, chlormethine, cyclophosphamide, ifosfamide, and melphalan), nitrosoureas (for example, carmustine, fotemustine, lomustine, and streptozocin), platinum compounds (for example, carboplatin, cisplatin, oxaliplatin, and BBR3464), busulfan, dacarbazine, mechlorethamine, procarbazine, temozolomide, thiotepa, and uramustine; folic acid (for example, methotrexate, pemetrexed, and raltitrexed), purine (for example, cladribine, clofarabine, fludarabine, mercaptopurine, and tioguanine), pyrimidine (for example, capecitabine), cytarabine, fluorouracil, and gemcitabine; plant alkaloids, such as *podophyllum* (for example, etoposide, and teniposide); microtubule binding agents (such as paclitaxel, docetaxel, vinblastine, vindesine, vinorelbine (navelbine) vincristine, the epothilones, colchicine, dolastatin 15, nocodazole, podophyllotoxin, rhizoxin, and derivatives and analogs thereof), DNA intercalators or cross-linkers (such as cisplatin, carboplatin, oxaliplatin, mitomycins, such as mitomycin C, bleomycin, chlorambucil, cyclophosphamide, and derivatives and analogs thereof), DNA synthesis inhibitors (such as methotrexate, 5-fluoro-5'-deoxyuridine, 5-fluorouracil and analogs thereof); anthracycline family members (for example, daunorubicin, doxorubicin, epirubicin, idarubicin, mitoxantrone, and valrubicin); antimetabolites, such as cytotoxic/antitumor antibiotics, bleomycin, rifampicin, hydroxyurea, and mitomycin; topoisomerase inhibitors, such as topotecan and irinotecan; monoclonal antibodies, such as alemtuzumab, bevacizumab, cetuximab, gemtuzumab, rituximab, panitumumab, pertuzumab, and trastuzumab; photosensitizers, such as aminolevulinic acid, methyl aminolevulinate, porfimer sodium, and verteporfin, enzymes, enzyme inhibitors (such as camptothecin, etoposide, formestane, trichostatin and derivatives and analogs thereof), kinase inhibitors (such as imatinib, gefitinib, and erolitinib), gene regulators (such as raloxifene, 5-azacytidine, 5-aza-2'-deoxycytidine, tamoxifen, 4-hydroxytamoxifen, mifepristone and derivatives and analogs thereof); and other agents, such as alitretinoin, altretamine, amsacrine, anagrelide, arsenic trioxide, asparaginase, axitinib, bexarotene, bevacizumab, bortezomib, celecoxib, denileukin diftitox, estramustine, hydroxycarbamide, lapatinib, pazopanib, pentostatin, masoprocol, mitotane, pegaspargase, tamoxifen, sorafenib, sunitinib, vemurafinib, vandetanib, and tretinoin. Methods and therapeutic dosages of such agents are known to those skilled in the art, and can be determined by a skilled clinician. Other therapeutic agents, for example anti-tumor agents, that may or may not fall under one or more of the classifications above, also are suitable for administration. Selection and therapeutic dosages of such agents are known to those skilled in the art, and can be determined by a skilled clinician.

In some examples, the dose of an EGFR inhibitory nucleic acid (such as an antisense molecule, siRNA, shRNA, or miRNA) is about 1 mg to about 1000 mg, about 10 mg to about 500 mg, or about 50 mg to about 100 mg. In some examples, the dose of antisense compound is about 1 mg, about 10 mg, about 50 mg, about 100 mg, about 250 mg, about 500 mg or about 1000 mg. In some embodiments, the dose of a EGFR inhibitory nucleic acid is about 1.0 mg/kg to about 100 mg/kg, or about 5.0 mg/kg to about 500 mg/kg, about 10 mg/kg to about 100 mg/kg, or about 25 to about 50 mg/kg. In some examples, the dose of a EGFR inhibitory nucleic acid is about 1.0 mg/kg, about 5 mg/kg, about 10 mg/kg, about 12.5 mg/kg, about 15 mg/kg, about 20 mg/kg, about 25 mg/kg, about 30 mg/kg, about 35 mg/kg, about 40 mg/kg, about 45 mg/kg, about 50 mg/kg, about 60 mg/kg, about 70 mg/kg, about 80 mg/kg or about 100 mg/kg. It will be appreciated that these dosages are examples only, and an appropriate dose can be determined by one of ordinary skill in the art using only routine experimentation.

In some embodiments, the dose of an EGFR antibody or antibody conjugate is about 1 mg/kg to about 25 mg/kg, such as about 2 mg/kg to about 15 mg/kg, about 2 mg/kg to about 10 mg/kg, or about 2 mg/kg to about 8 mg/kg. In some examples, the dose of EGFR antibody is about 1 mg/kg, about 2 mg/kg, about 4 mg/kg, about 5 mg/kg, about 6 mg/kg, about 8 mg/kg, about 10 mg/kg, about 15 mg/kg, about 20 mg/kg, or about 25 mg/kg. In other embodiments, the dose of EGFR antibody is about 50 $mg/m^2$ to about 500 $mg/m^2$, such as about 50 $mg/m^2$ to about 400 $mg/m^2$, about 100 $mg/m^2$ to about 400 $mg/m^2$, or about 250 $mg/m^2$ to about 400 $mg/m^2$. In some examples, the dose is about 50 $mg/m^2$, about 100 $mg/m^2$, about 150 $mg/m^2$, about 200 $mg/m^2$, about 250 $mg/m^2$, about 300 $mg/m^2$, about 400 $mg/m^2$, or about 500 $mg/m^2$. It will be appreciated that these dosages are examples only, and an appropriate dose can be determined by one of ordinary skill in the art using only routine experimentation.

In a non-limiting example, a therapeutically effective amount of GA201 is administered to a subject having a tumor that is identified as having elevated CD3 and/or CD16 protein expression. In some examples, a therapeutically effective amount of a GA201 can be about 50-3000 mg (such as 700 to 2000 or 700 to 1400 mg), administered via injection (e.g., iv, im, ip) once-weekly (QW), biweekly (Q2 W), or every three weeks (Q3 W) (see for example Markman et al., *J. Clin. Oncol.* 28:2522, 2010, and Gerdes et al., *Clin. Can. Res.* 19:1126-38, 2013, both herein incorporated by reference). In a specific example, GA201 is administered at 1400 mg on days 1'8 followed by 1400 mg/q2 W. Dosages and dosing schedules of GA201 for a subject can be determined by a skilled clinician, taking into account additional factors such as tumor site, tumor stage, tumor grade, patient treatment history, patient performance and nutritional status, concomitant health problems, social and logistic factors, previous primary tumors, and patient preference.

E. Outputs

Following the detection of CD3 and CD16, the assay results, such as the CD3 and CD16 protein score, number of CD3 cells and CD16 cells (such as the number of cells in the tumor regions of the sample), findings, prognosis, predictions and/or treatment recommendations can be recorded and communicated to technicians, physicians and/or patients, for example. In certain embodiments, computers are used to communicate such information to interested parties, such as, patients and/or the attending physicians. Based on the prognosis of the tumor (such as whether the tumor is likely to respond to EGFR-targeted therapy), the subject from whom the sample was obtained can be assigned a treatment plan, such as treatment or not with an EGFR-targeted therapy (such as GA201).

Thus in some examples the method includes providing an output related to the scoring. For example, the output can be the number of CD3 cells and the number of CD16 cells counted in a grid (such as CD3 and/or CD16 positive immune cells that have infiltrated the tumor), the number of CD3 cells and the number of CD16 cells counted in a grid that has been normalized to 1 mm square region. In one example, the output can be an absolute number of cells staining with the CD3 antibody and the CD16 antibody within the tumor cells of the sample, an absolute number of cells staining with the CD3 antibody within the tumor cells of the sample, an absolute number of cells staining with the CD16 antibody within the tumor cells of the sample, an absolute number of cells staining with the CD3 antibody and the CD16 antibody in intratumoral and contiguous peri-tumoral stroma of the sample, an absolute number of cells staining with the CD3 antibody in intratumoral and contiguous peri-tumoral stroma of the sample, an absolute number of cells staining with the CD16 antibody in intratumoral and contiguous peri-tumoral stroma of the sample, or combinations thereof. In one example, the output can be a score of CD3 protein for the intra-tumoral region and the contiguous peri-tumoral stroma, a score of CD16 protein for the intra-tumoral region and the contiguous peri-tumoral stroma, or both. In one example, the output can be a score of CD3 protein for the stroma, a score of CD16 protein for the stroma, or both.

In one embodiment, a CD3/CD16 score, a prognosis, prediction and/or treatment recommendation based on the output value is communicated to interested parties as soon as possible after the assay is completed and the scoring and/or prognosis is generated. The results and/or related information may be communicated to the subject by the subject's treating physician. Alternatively, the results may be communicated directly to interested parties by any means of communication, including writing, such as by providing a written report, electronic forms of communication, such as email, or telephone. Communication may be facilitated by use of a suitably programmed computer, such as in case of email communications. In certain embodiments, the communication containing results of a prognostic test and/or conclusions drawn from and/or treatment recommendations based on the test, may be generated and delivered automatically to interested parties using a combination of computer hardware and software which will be familiar to artisans skilled in telecommunications. One example of a healthcare-oriented communications system is described in U.S. Pat. No. 6,283,761; however, the present disclosure is not limited to methods which utilize this particular communications system.

In certain embodiments of the methods of the disclosure, all or some of the method steps, including the assaying of samples, scoring of CD3 and CD16 protein expression, prognosis of the tumor, and communicating of assay results or prognosis, may be carried out in diverse (e.g., foreign) jurisdictions.

Systems

Figure 26:
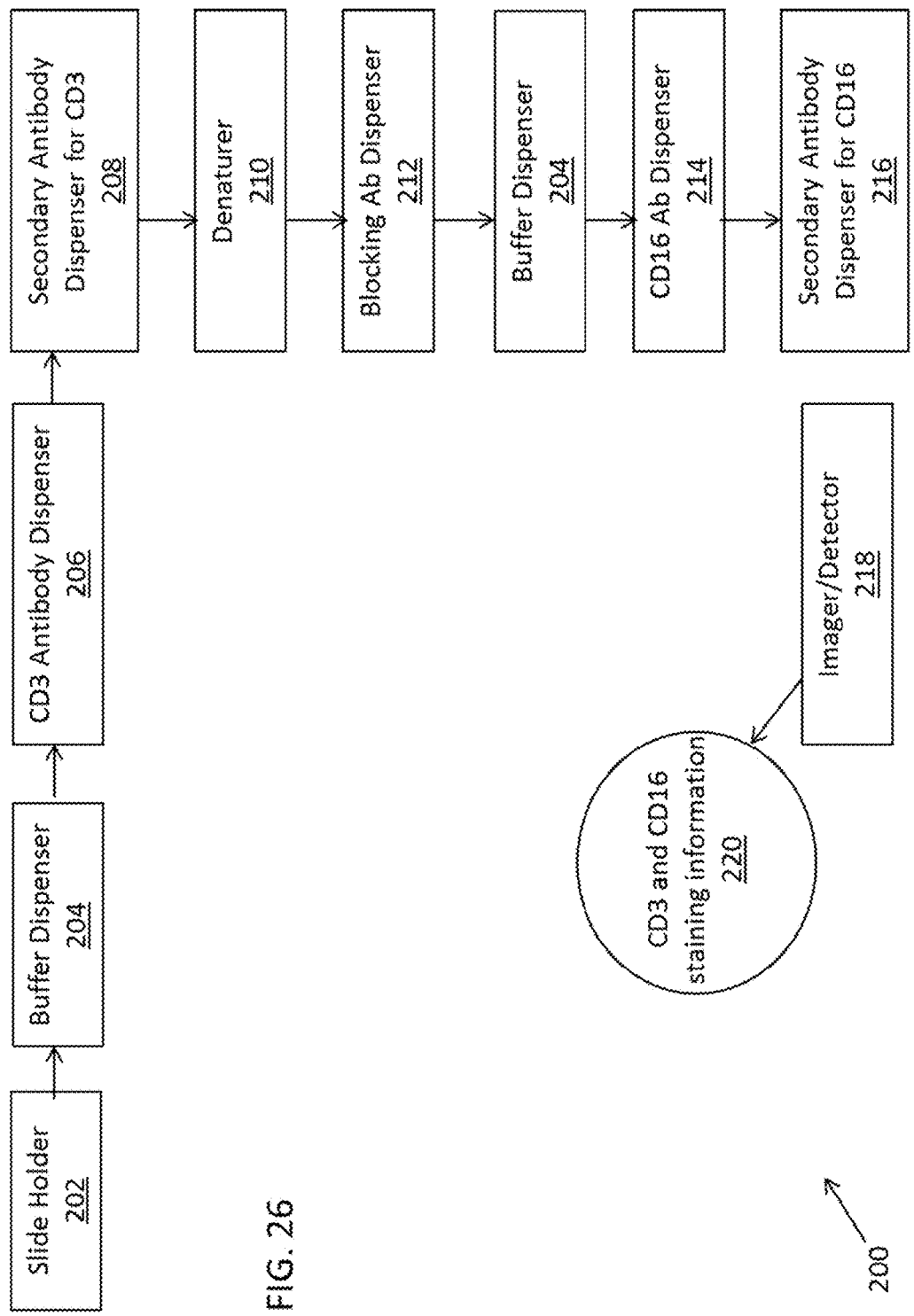
FIG. 26 is a block diagram of an exemplary system 200 implementing CD3 and CD16 protein expression analysis.

FIG. 26 is a block diagram of an exemplary system 200 implementing analysis of CD3 and CD16 protein expression using IHC as described herein.

In practice, the systems shown herein, such as system for analyzing CD3 and CD16 protein expression can be more complicated, with additional functionality.

Various other components, such as analog-to-digital converters, and the like are not shown but can be included to couple the components.

The system 200 and any of the other systems described herein can be implemented in conjunction with any of the hardware components described herein, such as the computing systems or mobile devices described below (e.g., including one or more processors, memory, and the like). In any of the examples herein, the CD3 and CD16 staining information 220 (which can include one or more of a CD3/CD16 score, number of positive cells, prognosis, histology data, digital histology images, outputs, and the like) and applications can be stored in one or more computer-readable storage media or computer-readable storage devices. The technologies described herein can be generic to the specifics of operating systems or hardware and can be applied in any variety of environments to take advantage of the described features.

Referring to FIG. 26, the system 200 can include a means or device to hold slides 202. For examples, the holder 202 can include a plurality of slides containing tissue samples, such as FFPE samples. In some examples, the slides include multiple sections of a tissue from one patient. In some examples, the slides include one or more sections of a tissue from one or more patients. In some examples, the system 200 can include a plurality of slide holders 202. Slides can include one tissue section, or a series of tissue sections.

The system can further include a plurality of dispensers 204, 206, 208, 214, 216 configured to dispense desired reagents onto the slides. For example, the dispensers 204, 206, 208, 214, 216 can store reagents needed for IHC, and be arranged such that appropriate amounts of reagents (such as a fluid) are allowed to sufficiently contact the sample on the slide. One skilled in the art will appreciate that the system 200 can include one or more other containers (not shown), for example containing agents to permit dilution of reagents in other dispensers (such as a buffer to dilute an antibody solution, such as a Tris buffer at a pH of about 7.6+/−0.2, such as Ventana Medical Systems Inc., catalog #950-300), to collect the reagents after they are applied to a slide (e.g., a waste container), or combinations thereof. In one example, the system includes buffer dispensers 204, such as those that contain a buffer of about pH 8-9 containing Tris and a preservative (such as the CC1 buffer described herein). In one example, the system includes antibody dispensers 206, 208, 214, 216 such as those that contain a CD3 primary antibody 206, CD3 secondary antibody 208, a blocking antibody 210, CD16 primary antibody 214, and CD16 secondary antibody 216. In some examples, the secondary antibody dispensers 208, 216 include a plurality of dispensers, each containing a reagent needed to permit detection of the primary antibody. For example, if the CD3 secondary antibody comprises an anti-rabbit-HQ conjugate (or an anti-mouse-HQ conjugate) and an anti-HQ-HRP antibody, the CD3 secondary antibody dispenser 208, can include a plurality of dispensers, such as one containing anti-rabbit-HQ conjugate or anti-mouse-HQ conjugate, one dispenser containing anti-HQ-HRP antibody, one dispenser containing hydrogen peroxide, one dispenser containing diaminobenzidine (DAB), and one dispenser containing copper sulfate. Similarly, if the CD16 secondary antibody comprises anti-rabbit-AP multimer or anti-mouse-AP multimer, the CD14 secondary antibody dispenser 216 can include a plurality of dispensers, such as one containing the anti-rabbit-AP multimer or anti-mouse-AP multimer, one containing napthol, one containing alkaline phosphatase enhancer, and one containing fast red.

The system can further include a denaturer 210 configured to allow denaturation of the first primary antibody (CD3 primary antibody shown in FIG. 26, but it can be the CD16 primary antibody if that is contacted with the sample before the CD3 primary antibody) after it is contacted with its corresponding secondary antibody. The denaturer can include a plurality of components, such as a means to heat the sample and a dispenser containing the desired denaturation buffer (such as reaction buffer; for example a Tris buffer at a pH of about 7.6+/−0.2, such as Ventana Medical Systems Inc., catalog #950-300).

The system can further include an imager and/or a detector 218 configured to collect CD3 and CD16 staining information. The imager and detector can be in a single device or divided into multiple devices. For example, the imager and/or detector 218 can be a microscope, such as a light microscope or fluorescent microscope. Such microscopes can be configured to detect signals (such as a label) associated with the CD3 and CD16 antibodies. Such a device permits imaging of the sample stained with the CD3 and CD16 primary and secondary antibodies. Thus, the device 218 permits for histological analysis of a sample, such as using IHC.

The system can further include a processor (not shown) configured to collect (and in some example store) images showing CD3 and CD16. Thus, in some examples system has a means (e.g., computer) to store the CD3 and CD16 staining data 220.

The disclosed system can include an automated slide stainer (such as BENCHMARK instruments from Ventana Medical Systems, for example BENCHMARK XT or BENCHMARK GX instruments). These stainers permit staining of the sample with appropriate antibodies, generation of images showing the location of the staining on the sample by the antibodies, as well as storage of such information.

The system can also include means to control the temperature at which a reaction occurs (not shown), such as a means to change the temperature or maintain a temperature for a desired amount of time. For example, in some parts of the method the slide is incubated at 37° C. (for example during incubation with antibodies), while other steps require other temperatures, such as an initial incubation at about 95° C. and denaturing at 80° C.-100° C. (such as 95° C.).

Computer-Readable Media

The disclosure provides one or more computer-readable storage media that include computer-executable instructions causing a computer to perform the methods provided herein.

Any of the computer-readable media herein can be non-transitory (e.g., memory, magnetic storage, optical storage, or the like).

Any of the storing actions described herein can be implemented by storing in one or more computer-readable media (e.g., computer-readable storage media or other tangible media).

Any of the things described as stored can be stored in one or more computer-readable media (e.g., computer-readable storage media or other tangible media).

Any of the methods described herein can be implemented by computer-executable instructions in (e.g., encoded on) one or more computer-readable media (e.g., computer-readable storage media or other tangible media). Such instructions can cause a computer to perform the method. The technologies described herein can be implemented in a variety of programming languages.

Any of the methods described herein can be implemented by computer-executable instructions stored in one or more computer-readable storage devices (e.g., memory, magnetic storage, optical storage, or the like). Such instructions can cause a computer to perform the method.

Any of the computer-readable media herein can be non-transitory (e.g., memory, magnetic storage, optical storage, or the like).

Any of the storing actions described herein can be implemented by storing in one or more computer-readable media (e.g., computer-readable storage media or other tangible media).

Any of the things described as stored can be stored in one or more computer-readable media (e.g., computer-readable storage media or other tangible media).

Exemplary Computing Systems

Figure 29:
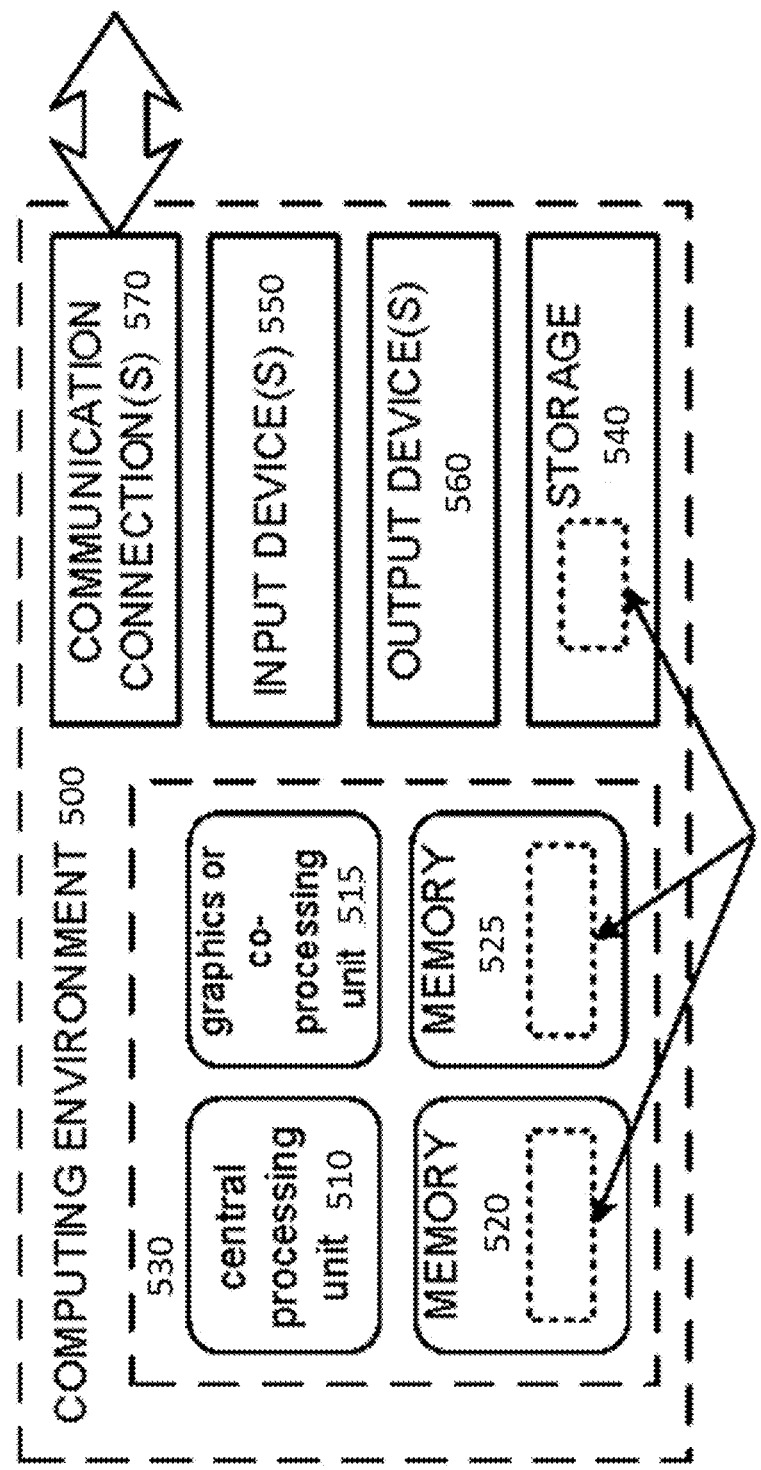
FIG. 29 is a diagram of an exemplary computing system 500 in which described embodiments can be implemented.

FIG. 29 illustrates a generalized example of a suitable computing system or environment 500 in which several of the described embodiments can be implemented. The computing system 500 is not intended to suggest any limitation as to scope of use or functionality, as the innovations may be implemented in diverse general-purpose or special-purpose computing systems. A communication device as described herein can take the form of the described computing system 500.

With reference to FIG. 29, the computing system 500 includes one or more processing units 510, 515 and memory 520, 525. In FIG. 29, this basic configuration 530 is included within a dashed line. The processing units 510, 515 execute computer-executable instructions. A processing unit can be a general-purpose central processing unit (CPU), processor in an application-specific integrated circuit (ASIC) or any other type of processor. In a multi-processing system, multiple processing units execute computer-executable instructions to increase processing power. For example, FIG. 29 shows a central processing unit 510 as well as a graphics processing unit or co-processing unit 515. The tangible memory 520, 525 may be volatile memory (e.g., registers, cache, RAM), non-volatile memory (e.g., ROM, EEPROM, flash memory, etc.), or some combination of the two, accessible by the processing unit(s). The memory 520, 525 stores software 580 implementing one or more innovations described herein, in the form of computer-executable instructions suitable for execution by the processing unit(s).

A computing system may have additional features. For example, the computing system 500 includes storage 540, one or more input devices 550, one or more output devices 560, and one or more communication connections 570. An interconnection mechanism (not shown) such as a bus, controller, or network interconnects the components of the computing system 500. Typically, operating system software (not shown) provides an operating environment for other software executing in the computing system 500, and coordinates activities of the components of the computing system 500.

The tangible storage 540 may be removable or non-removable, and includes magnetic disks, magnetic tapes or cassettes, CD-ROMs, DVDs, or any other medium which can be used to store information in a non-transitory way and which can be accessed within the computing system 500. The storage 540 stores instructions for the software 580 implementing one or more innovations described herein.

The input device(s) 550 may be a touch input device such as a keyboard, mouse, pen, or trackball, a voice input device, a scanning device, or another device that provides input to the computing system 500. For video encoding, the input device(s) 550 may be a camera, video card, TV tuner card, or similar device that accepts video input in analog or digital form, or a CD-ROM or CD-RW that reads video samples into the computing system 500. The output device(s) 560 may be a display, printer, speaker, monitor, CD-writer, or another device that provides output from the computing system 500.

The communication connection(s) 570 enable communication over a communication medium to another computing entity. The communication medium conveys information such as computer-executable instructions, audio or video input or output, or other data in a modulated data signal. A modulated data signal is a signal that has one or more of its characteristics set or changed in such a manner as to encode information in the signal. By way of example, and not limitation, communication media can use an electrical, optical, RF, or other carrier.

The innovations can be described in the general context of computer-readable media. Computer-readable media are any available tangible media that can be accessed within a computing environment. By way of example, and not limitation, with the computing system 500, computer-readable media include memory 520, 525, storage 540, and combinations of any of the above.

The innovations can be described in the general context of computer-executable instructions, such as those included in program modules, being executed in a computing system on a target real or virtual processor (e.g., which is ultimately executed in hardware). Generally, program modules include routines, programs, libraries, objects, classes, components, data structures, etc. that perform particular tasks or implement particular abstract data types. The functionality of the program modules may be combined or split between program modules as desired in various embodiments. Computer-executable instructions for program modules may be executed within a local or distributed computing system.

The terms "system" and "device" are used interchangeably herein. Unless the context clearly indicates otherwise, neither term implies any limitation on a type of computing system or computing device. In general, a computing system or computing device can be local or distributed, and can include any combination of special-purpose hardware and/or general-purpose hardware with software implementing the functionality described herein.

For the sake of presentation, the detailed description uses terms like "determine" and "use" to describe computer operations in a computing system. These terms are high-level abstractions for operations performed by a computer, and should not be confused with acts performed by a human being. The actual computer operations corresponding to these terms vary depending on implementation.

Exemplary Cloud-Supported Environment

FIG. 30 illustrates a generalized example of a suitable cloud-supported environment 600 in which several of the described embodiments can be implemented. In example environment 600, the cloud 610 provides services for connected devices 630, 640, 650 with a variety of screen capabilities. Connected device 630 represents a device with a computer screen 635 (e.g., a mid-size screen). For example, connected device 630 could be a personal computer such as desktop computer, laptop, notebook, netbook, or the like. Connected device 640 represents a device with a mobile device screen 645 (e.g., a small size screen). For example, connected device 640 could be a mobile phone, smart phone, personal digital assistant, tablet computer, and the like. Connected device 650 represents a device with a large screen 655. For example, connected device 650 could be a television screen (e.g., a smart television) or another device connected to a television (e.g., a set-top box or gaming console) or the like. One or more of the connected devices 630, 640, 650 can include touch screen capabilities. Touchscreens can accept input in different ways. For example, capacitive touchscreens detect touch input when an object (e.g., a fingertip or stylus) distorts or interrupts an electrical current running across the surface. As another example, touchscreens can use optical sensors to detect touch input when beams from the optical sensors are interrupted. Physical contact with the surface of the screen is not necessary for input to be detected by some touchscreens. Devices without screen capabilities also can be used in example environment 600. For example, the cloud 610 can provide services for one or more computers (e.g., server computers) without displays.

Services can be provided by the cloud 610 through service providers 620, or through other providers of online services (not depicted). For example, cloud services can be customized to the screen size, display capability, and/or touch screen capability of a particular connected device (e.g., connected devices 630, 640, 650).

In example environment 600, the cloud 610 provides the technologies and solutions described herein to the various connected devices 630, 640, 650 using, at least in part, the service providers 620. For example, the service providers 620 can provide a centralized solution for various cloud-based services. The service providers 620 can manage service subscriptions for users and/or devices (e.g., for the connected devices 630, 640, 650 and/or their respective users).

Exemplary Implementations

Although the operations of some of the disclosed methods are described in a particular, sequential order for convenient presentation, it should be understood that this manner of description encompasses rearrangement, unless a particular ordering is required by specific language set forth herein. For example, although staining with CD3 primary and secondary antibodies is usually listed herein prior to staining with CD16 primary and secondary antibodies, one skilled in the art that the order of such staining can be reversed. However, denaturation and use of the blocking antibody is done prior to contacting the sample with the second primary antibody. In addition, operations described sequentially may in some cases be rearranged or performed concurrently. Moreover, for the sake of simplicity, the attached figures may not show the various ways in which the disclosed methods can be used in conjunction with other methods.

Any of the disclosed methods can be implemented as computer-executable instructions stored on one or more computer-readable storage media (e.g., non-transitory computer-readable media, such as one or more optical media discs, volatile memory components (such as DRAM or SRAM), or nonvolatile memory components (such as hard drives)) and executed on a computer (e.g., any commercially available computer, including smart phones or other mobile devices that include computing hardware). Any of the computer-executable instructions for implementing the disclosed techniques as well as any data created and used during implementation of the disclosed embodiments can be stored on one or more computer-readable media (e.g., non-transitory computer-readable media). The computer-executable instructions can be part of, for example, a dedicated software application or a software application that is accessed or downloaded via a web browser or other software application (such as a remote computing application). Such software can be executed, for example, on a single local computer (e.g., any suitable commercially available computer) or in a network environment (e.g., via the Internet, a wide-area network, a local-area network, a client-server network (such as a cloud computing network), or other such network) using one or more network computers.

For clarity, only certain selected aspects of the software-based implementations are described. Other details that are well known in the art are omitted. For example, it should be understood that the disclosed technology is not limited to any specific computer language or program. For instance, the disclosed technology can be implemented by software written in C++, Java, Perl, JavaScript, Adobe Flash, or any other suitable programming language. Likewise, the disclosed technology is not limited to any particular computer or type of hardware. Certain details of suitable computers and hardware are well known and need not be set forth in detail in this disclosure.

Furthermore, any of the software-based embodiments (including, for example, computer-executable instructions for causing a computer to perform any of the disclosed methods) can be uploaded, downloaded, or remotely accessed through a suitable communication means. Such suitable communication means include, for example, the Internet, the World Wide Web, an intranet, software applications, cable (including fiber optic cable), magnetic communications, electromagnetic communications (including RF, microwave, and infrared communications), electronic communications, or other such communication means.

The disclosed methods, apparatus, and systems should not be construed as limiting in any way. Instead, the present disclosure is directed toward all novel and nonobvious features and aspects of the various disclosed embodiments, alone and in various combinations and subcombinations with one another. The disclosed methods, apparatus, and systems are not limited to any specific aspect or feature or combination thereof, nor do the disclosed embodiments require that any one or more specific advantages be present or problems be solved.

Methods in Computer-Readable Media

Any of the methods described herein can be implemented by computer-executable instructions in (e.g., encoded on) one or more computer-readable media (e.g., computer-readable storage media or other tangible media). Such instructions can cause a computer to perform the method. The technologies described herein can be implemented in a variety of programming languages.

Methods in Computer-Readable Storage Devices

Any of the methods described herein can be implemented by computer-executable instructions stored in one or more computer-readable storage devices (e.g., memory, magnetic storage, optical storage, or the like). Such instructions can cause a computer to perform the method.

The present disclosure is illustrated by the following non-limiting Examples.

Example 1

Development of Conditions to Detect CD16

This example provides the materials and methods used to identify CD16 staining conditions.

Three antibodies against CD16 were screened (Table 1). An assay using one of these antibodies, a rabbit monoclonal, J224H2L1 (Spring Bioscience, CA), was then developed with UltraView DAB detection system on a BenchMark XT platform (Ventana, Tucson, Ariz.). The performance of the assay was reviewed by a board certified pathologist.

TABLE 1

CD16 Antibodies Examined.

| Antibody Target | Vendor | Lot No. | Species | Ig Type | Clonality | Clone No. |
|---|---|---|---|---|---|---|
| CD16 | Spring | 120511-2 | Rabbit | IgG | Monoclonal | J224H2L1 |
| CD16 | Spring | 120526 | Rabbit | IgG | Monoclonal | J60H2L46 |
| CD16 | Spring | 120515 | Rabbit | IgG | Monoclonal | S52-246L3 |

Antibody diluent A (VMSI, 4% or ~6 mg/mL protein solution containing 1% non-ionic surfactant, Tris buffered to pH of 7.3 with ~0.4 M NaCl) was used as negative reagent control to examine the presence of secondary antibody and detection chemistry reactivity.

A panel of formalin-fixed, paraffin-embedded cancer tissues was used to screen the CD16 antibodies (Table 2). Representative photomicrographs from screening are shown in FIGS. 1A-F.

TABLE 2

Description of Tissue Controls Examined.

| Case ID | Origin | Tissue Type | Control Type |
|---|---|---|---|
| 91S-4130-E1 | Head/Neck | FFPE | Positive |
| 5931 | Colorectal | FFPE | Positive |
| 90S-3514-C4B | Non-small cell lung | FFPE | Positive |

91S-4130-E1 head/neck cancer (FIGS. 1A-B), 5931 colorectal cancer (FIGS. 1C-D), and 90S-3514-C4B non-small cell lung cancer (FIGS. 1E-F) were selected to use as the development tissues. The observed expression patterns were similar to what was expected based on a survey of the literature showing variable percentage of infiltrating CD16 cells with membrane staining. Also, these cases demonstrated a limited range of intensity, and therefore can provide insight to the performance of the assay across tissues expressing a limited range of antigen levels.

Antigen retrieval, primary antibody concentration, and diluent were evaluated to optimize staining quality.

Antigen retrieval was analyzed using a variety of cell conditioning buffers and incubation times. Cell conditioning 1 (CC1) buffer is a TRIS based buffer of alkaline pH (Ventana Medical Systems, Inc., Catalog #950-124; Tris/Boric acid/EDTA, pH 8.6). CC1 is an exemplary cell conditioning composition, which includes Tris borate-ethylene diamine tetraacetic acid (EDTA) buffer, at a slightly basic pH. The preservative in CC1 is 0.05% ProClin 5000, containing the active ingredients 5-chloro-2-methyl-4-isothiazine-3-one and 2-methyl-4-isothiazolin-3-one. It is not diluted before use. CC1, at elevated temperatures, is capable of hydrolyzing the covalent bonds formed by formalin in tissue. Removing these bonds allows renaturation of protein molecules and increases antibody accessibility.

CC1 was tested at two incubation times, "mild" (32 minutes) and "standard" (60 minutes). Of these conditions, CC1 "standard" incubation time (60 minutes) yielded results that were superior to the other conditions tested. This was selected as the antigen retrieval parameter for the final assay.

The intensity of staining at different titers of the CD16 antibody was evaluated by the pathologist to select the titer for validation. Titration of the CD16 antibody was performed in the range of 1:2000 to 1:10000 dilutions of the supplied stock. An automatically dispensed titer of 1:5000 was selected for validation based on the pathologist's interpretation of relevant positive staining and non-specific background reactivity. Representative photomicrographs from the titration series are shown in FIGS. 2A-2F.

Five internal diluents (A-E) were screened and evaluated for staining quality (FIGS. 3A-3F). Diluent A (FIG. 3B) was selected for the final assay.

FIGS. 4A-4F show analysis of CD16 antibody staining under optimized conditions.

Example 2

Dual Immunohistochemistry (DIHC) Assay for CD3 and CD16

A dual chromogenic IHC assay using a CD3 rabbit monoclonal antibody from Ventana Medical Systems (VMSI, Cat No. 790-4341 Clone ID 2GV6) and a CD16 antibody from Spring Bioscience (Spring Bioscience, CA, Clone ID J224H2L1), was developed and validated. The anti-CD3 antibody is a rabbit IgG at a stock concentration of 0.4 ug/ml. The performance of the assay was reviewed by a board certified pathologist.

Hematoxylin and Eosin (H&E) stains were performed on tissues and cell lines to examine specimen quality and appropriateness.

The CD3 and CD16 analyses were carried out using Ventana's BenchMark ULTRA staining platform with the antibodies shown in Table 3.

TABLE 3

CD3 and CD16 Antibodies Examined.

| Antibody Target | Vendor | Catalog No. | Lot No. | Species | Ig Type | Clonality | Clone No. |
|---|---|---|---|---|---|---|---|
| CD3 | VMSI | 790-4341 | CO3820 | Rabbit | IgG | Monoclonal | 2GV6 |
| CD16 | Spring | N/A | 120511-2 | Rabbit | IgG | Monoclonal | J224H2L1 |

Antibody diluent A (VMSI) was used as a negative reagent control to examine the presence of secondary antibody and detection chemistry reactivity. A panel of formalin-fixed, paraffin-embedded cancer tissues was used to screen the CD16 and CD3 antibodies (Table 4).

TABLE 4

Description of Tissue Controls Examined.

| Case ID | Origin | Tissue Type | Control Type |
|---|---|---|---|
| 91S-4130-E1 | Head/Neck | FFPE | Positive |
| 5931 | Colorectal | FFPE | Positive |
| 90S-3514-C4B | Non-small cell lung | FFPE | Positive |

A panel of formalin-fixed, paraffin-embedded tissues (head/neck, colorectal, and non-small cell lung cancer samples) was examined throughout the screening, development, and validation processes.

90S-3514-C4B non-small cell lung cancer was selected as the specimen on which to validate the assay, based on the staining characteristics of the tissue. Generally, a tissue exhibiting high overall staining intensity is preferred to reduce the inflation of coefficient of variation values during precision analysis. Conversely, an extremely high staining tissue is not acceptable since it is difficult to measure variations in staining if the signal is saturated. It is also best to use a tissue that exhibits a full range of staining in order to gauge the performance of the assay across the range of expression levels encountered. Finally, a large positively staining tumor area ensures that adequate region is available as the tissue is sectioned throughout the course of analysis.

A fifty-nine core multi-organ tissue array (SuperBioChips, Seoul, South Korea, Catalog No. BC8) was evaluated to verify localization of CD3 and CD16 in normal and neoplastic human tissues.

Three multi-tissue arrays of head/neck, colorectal, and non-small cell lung malignancies were examined to validate the assay (Pantomics, Catalog Nos. HNT1021, COC1021, and LUC1021 respectively). Thirty-five total whole tissue specimens and multi-tissue array cores of hepatocellular malignancies were examined to validate the assay for this intended indication (Biomax, Catalog No. LV8012).

Initial screens were performed to select the development and validation tissue(s), to identify an appropriate instrument and detection chemistry, and to approximate a base protocol from which the final assay would be generated. A limited titration series was also performed. Combinations of assay conditions which were successfully employed in previous assays were used in the initial screens. The assay passed screening by meeting minimum performance standards, such as a threshold for staining intensity, the expected tissue and cell type reactivity, correct subcellular localization, and upper limits on acceptable background staining.

The screening assay was further refined to optimize the combination of conditions to produce the most reliable and robust assay possible. The assay parameters that were optimized included titration of the antibody, epitope unmasking conditions, antibody denaturation, and cross reactivity examination. The background (nonspecific staining) of the assay was also examined, as were the maintenance of cell and tissue morphology, and the demonstration of proper cell type and cell localization staining.

Although antibodies are typically raised against well-defined antigens, cross reactivity is not uncommon. Staining characteristics were therefore analyzed to provide evidence for the specificity of antigen staining. These characteristics included:

Staining patterns in tissues examined that match those described in the literature.
Cell type and subcellular localization of staining consistent with published reports.
Intensity of staining in control specimens that reflects what is known about the antigen's expression level.
Negative control stains that demonstrate acceptable background.

To ensure the consistency of the assay, intra-run, inter-run, and inter-instrument precisions were analyzed. These assays were performed on the same tissue specimen using serial sections.

Precision runs were performed on the highest quality tissue available (which may not be representative of samples in a retrospective study). In addition to yielding easily interpretable, clean staining, tissue should arise from a reliable source utilizing preferred procurement methodology. This was done to facilitate interpretation of the experimental results.

Federal guidelines for the validation of analytical procedures indicate that overall variation in assay performance should be less than 15% expressed as a coefficient of variation. The coefficient of variation statistically increases at the lowest values in the range of detection of a system. Consequently, samples selected for precision validation are not in this low range.

The range of the assay was examined to assess the ability of the assay to detect varying amounts of analyte using the same assay conditions and antibody concentration; analytical procedures should be able to detect analyte over a meaningful range of expression levels to be biologically useful.

The linearity of the assay was examined to assess the ability of the assay to demonstrate varying staining intensities in the same specimen with differing concentrations of the primary detection antibody. Immunohistochemistry procedures are not absolutely linear—at high levels of antigen staining may plateau due to saturation of the detection reaction, and low antigen levels may result in artificially elevated staining due to signal amplification. However, within a given range, semi-quantitative measurements are possible, as reflected in the traditional pathology intensity scores of 0 (negative), 1, 2, and 3.

To examine the robustness of the assay, staining was assessed in a large set of tumor samples yielding a population-level understanding of variations in staining among specimens of the same tumor type. Additionally, during development assay parameters are evaluated and changed in order to achieve optimal staining. The degree of consistency in staining observed across a variety of assay parameters provides some indication of assay robustness.

Scoring of tissues stained for precision: A modified H score method was used to assess slides stained for assessing precision of CD3/CD16 dual IHC assay. The total number of cells staining for each marker was used as the denominator and % of cells staining at intensities 1, 2, and 3 were scored. An intensity of 1 was given to a tissue showing light red membrane staining above the level of background. A score of 3 was given to a tissue showing dark red membrane staining and a score of 2 to a tissue with an intensity between 1 and 3. Similarly, for CD3, an intensity of 1 was given to a tissue showing light brown membrane staining above the level of background, a score of 3 to a tissue showing dark brown staining often with black tint. A score of 2 was given to a tissue showing intensity between 1 and 3. Modified H score was calculated using the following formula:

$$1*(\text{percentage of cells staining at } 1+\text{intensity}) +$$
$$2*(\text{percentage of cells staining at } 2+\text{intensity}) +$$
$$3*(\text{percentage of cells staining at } 3+\text{intensity}) = \text{Modified } H \text{ score}.$$

Scoring of multi-tissue arrays: Evaluation of multi-tissue arrays was done with the use of a 5×5 grid at 40× magnification (0.75 Olympus BX51). The number of CD3 and CD16 positive cells is counted in fields or fields of view (FOV) in up to 5 randomly selected fields. The cells were counted using a cell counter and are expressed as absolute count. Tumor cell region was used for scoring whenever possible, but when stromal tissue was present in the field, it was included. Thus, immune cells among the tumor cells were counted.

The mean and standard deviation of each scored specimen were calculated and used to determine the coefficient of variation (CV), defined as:

$$CV(\%) = (\text{standard deviation/mean})*100.$$

Results

A panel of formalin-fixed, paraffin-embedded tissues was examined using CD3 and CD16 antibodies. Representative photomicrographs from screening are shown in FIGS. 5A-5F.

90S-3514-C4B was used as the development tissue. The observed expression patterns were similar to what was expected based on a survey of the literature showing variable percentage of infiltrating CD16 cells with membrane staining. Also, these cases demonstrated a limited range of intensity, and therefore provided insight to the performance of the assay across tissues expressing a variety of levels of antigen.

During development cell conditioning for CD3 and CD16 antibodies, denaturation and cross-reactivity experiments were evaluated to optimize staining quality in head/neck, colorectal, and non-small cell lung cancer.

Antigen retrieval was optimized by evaluating a variety of cell conditioning buffers and incubation times. Cell conditioning 1 (CC1) buffer is a TRIS based buffer of alkaline pH. The first cell condition screen for CD3 was completed in a range of 32 to 56 minutes in 8 minute intervals (FIGS. 6A-6D). The second cell conditioning screen for CD16 was completed in a range of no cell condition to 16 minutes in 8 minute intervals (FIGS. 7A-7C). A first cell conditioning of 40 minutes for CD3 (FIG. 6C) followed by a second cell conditioning of 8 minutes for CD16 (FIG. 7B) was selected as optimal. Cell conditioning was performed at 100° C.

Denaturation was used to help prevent in unbound first primary antibody (CD3) remaining on the slide. A denaturation screening was completed at a temperature of 95° C. at 4, 8, and 12 minutes (FIGS. 8A-8C). 8 minutes at 95° C. was chosen for the denaturation step (FIG. 8B). Denaturation was performed using reaction buffer (VMSI, Catalog No. 950-300).

The denaturation experiment revealed that denaturation alone was not enough to adequately remove unbound first primary antibody. A chicken anti-rabbit antibody blocker was used to resolve the observed cross-reactivity. The antibody blocker titration was tested using dilutions of 1:10 to 1:100, with 1:50 selected for further experiments (FIGS. 9A-9D).

Thus, in the final dual IHC assay, antigen recovery of CD3 was conducted with use of Cell Conditioner 1 buffer (VMSI, Catalog No. 950-124) for 40 minutes. Slides were then incubated at a stock antibody concentration of 0.4 ug/ml for 8 minutes at 37° C. Stock antibody concentration refers to the concentration at which the antibody is sold commercially, as concentrations of commercial antibodies are not always made available by manufacturers.

The CD3 antibody was detected using the OptiView detection kit (VMSI, Catalog No. 760-700). Primary antibody detection of anti-CD3 was accomplished with an anti-species-HQ conjugate, followed by detection with an anti-HQ-HRP antibody. Enzymatic detection proceeded in which the HRP conjugate was developed with hydrogen peroxide in the presence of diaminobenzidine (DAB) and copper sulfate.

Denaturation was then applied to the slides for 8 minutes at 95° C. Upon completion of the denaturation, a chicken anti-rabbit antibody at a dilution of 1:50 was applied to the slides and incubated for 32 minutes followed by Reaction Buffer (VMSI, Catalog No. 950-300) incubated on the slides for 32 minutes in order to rise off any residual antibody from the previous step.

Antigen recovery of CD16 was then conducted with use of Cell Conditioner 1 buffer (VMSI, Catalog No. 950-124) for 8 minutes. Slides were then incubated at a CD16 antibody clone J224H2L1 at a dilution of 1/5000 for 16 minutes at 37° C.

The CD16 antibody was detected using the UltraView Red detection kit (VMSI, Catalog No. 760-501). Primary antibody detection of anti-CD16 was accomplished with an anti-species-AP multimer. Enzymatic detection proceeded in which the UV Red universal multimer conjugate was developed with napthol in the presence of Alkaline Phosphatase enhancer (AP) and fast red.

The details of the protocol are presented Table 5 below.

TABLE 4

Assay Summary

| Antibody | Conditioning/Incubations |
| --- | --- |
| Primary Antibodies:<br>Anti-CD3 (VMSI, Catalog No. 790-4341)<br>Anti-CD16 (Clone: J224H2L1)<br>Background Control<br>Antibody Diluent A (VMSI) | CC1 40 minutes (VMSI, Catalog No. 950-124)<br>Primary antibody incubation conditions 8 min/37° C.<br>Concentration in dispenser = 0.4 µg/ml<br>Concentration on slide ~0.1 µg/ml<br>OptiView Detection Kit (VMSI, Catalog No. 760-700)<br>CC1 8 minutes (VMSI, Catalog No. 950-124)<br>Primary antibody incubation conditions: 1/5000; diluent; 16 min/37° C.<br>Concentration in dispenser = .136 µg/ml<br>Concentration on slide ~.034 µg/ml<br>UltraView Red Detection Kit (VMSI, Catalog No. 760-501) |

Anti-CD3 and anti-CD16 antibodies showed membrane localization, often with granular quality. Staining of macrophages with anti-CD16 antibody often appears as granular processes without apparent nuclei. Cells with only clearly visible nuclei were counted for CD16 scoring. Tissues stained with CD3/CD16 dual IHC assay often show slightly distorted morphology due to dual cell conditioning and denaturation steps. Scoring of tissues stained for precision analysis done using a modified H score method whereas multi-tissue arrays were scored using a grid method as described under methods section.

Three multi-tissue arrays of head/neck, colorectal, and non-small cell lung malignancies and normal morphology of the body were used for evaluation of CD3/CD16 staining. In addition, thirty-five total whole tissue specimens and multi-tissue array cores of hepatocellular malignancies were examined to validate the assay for this intended indication (Biomax, Catalog No. LV8012).

FIGS. 10A-10F show analysis of CD3/CD16 DIHC using optimized conditions.

TABLE 5

General Assay Performance Characteristics.

| Parameter | Result |
| --- | --- |
| Cell type specificity | As expected |
| Subcellular localization | Membrane |
| Staining pattern in tissue (focal or diffuse) | Diffuse |
| Staining pattern in cell (focal or diffuse) | Circumferential |
| Cell and tissue morphology | Maintained |
| Staining intensity | Acceptable range |
| Percentage of positive cells | As expected |
| Background | Low |
| Contrast to background | High |

Analyte Specificity

The localization of anti-CD3 and anti-CD16 antibodies reactivity to the membrane in head/neck, colorectal, and non-small cell lung cancer was consistent with the expected staining pattern (FIGS. 5B, 5D, and 5F).

The subcellular localization pattern was consistent across the specimens in a multi-tissue array (FIGS. 11A-11F). Moreover, the tissue distribution of CD3 and CD16 expression was similar to that expected from a survey of the literature.

A 59 core multi-organ tissue array (SuperBioChips, Seoul, South Korea, Catalog No. BC8) was evaluated to verify localization of the test antigen in normal and neoplastic human tissues. Of the specimens examined, 52 out of the 59 (88%) cores were able to be evaluated at five fields of area. The seven cores that were not able to be evaluated either had less than five fields evaluated or staining was not present on the core.

High visual contrast was observed between staining in the expected localization and background staining, which was low. This provides additional evidence for antibody specificity. Representative photomicrographs of tissues from the multi-tissue array are shown in FIGS. 11A-11F.

Precision

Inter-run and inter-instrument of anti-CD3 and antiCD16 staining intensities were consistent by pathologist evaluation (FIGS. 12A-12D, Table 7). These results are shown in photomicrographs of 90S-3514-C4B non-small cell lung cancer (FIGS. 13A-13E, FIGS. 14A-14E). The staining intensity of the negative control was minimal to none.

TABLE 6

Assay Precision Scores.

| Precision | Date of Run | Slide | CD3 H Score | CD16 H Score |
|---|---|---|---|---|
| Inter-Run | 24-SEP-2012 | Run 1, Slide 1 | 270 | 285 |
|  |  | Run 1, Slide 2 | 280 | 300 |
|  |  | Run 1, Slide 3 | 275 | 300 |
|  | 24-SEP-2012 | Run 2, Slide 1 | 280 | 300 |
|  |  | Run 2, Slide 2 | 295 | 300 |
|  |  | Run 2, Slide 3 | 300 | 300 |
|  | 24-SEP-2012 | Run 3, Slide 1 | 300 | 300 |
|  |  | Run 3, Slide 2 | 300 | 300 |
|  |  | Run 3, Slide 3 | 295 | 300 |
|  |  | negative control | negative | nd |
| Inter-Instrument | 24-SEP-2012 | Instrument 1, Slide 1 | 270 | 285 |
|  |  | Instrument 1, Slide 2 | 280 | 300 |
|  |  | Instrument 1, Slide 3 | 275 | 300 |
|  | 26-SEP-2012 | Instrument 2, Slide 1 | 270 | 280 |
|  |  | Instrument 2, Slide 2 | 295 | 300 |
|  |  | Instrument 2, Slide 3 | 180 | 210 |
|  | 26-SEP-2012 | Instrument 3, Slide 1 | 300 | 300 |
|  |  | Instrument 3, Slide 2 | 300 | 300 |
|  |  | Instrument 3, Slide 3 | 300 | 300 |

The coefficient of variation (expressed as a percentage) of the modified H scores for the CD3/CD16 assay was 4.2% (CD3)/1.7% (CD16) for inter-run precision and 13.7% (CD3)/10.3% (CD16) for inter-instrument precision. Pathologists were not blinded during the reading of precision slides.

Linearity and Range

Detection of the antibody-antigen complex produced observable staining in an IHC assay. With a linear assay, a decrease in antigen or antibody should be directly proportional to a decrease in signal. An optimal antibody titer for the CD16 of 1:5000 was selected based on the onset of observable decrease in signal approximately following this concentration (FIGS. 2A-2F). CD3 did not have an optimal antibody titer chosen since it is a pre formulated product. Incremental decreases in antibody concentration resulted in proportional decreases in staining intensity, confirming the linearity of the assay.

The multi-tissue array contains single cores, in which CD3 and CD16 staining was demonstrated (FIGS. 11B, 11D and 11F). Additionally, the intended use tissues examined demonstrated a limited range of staining intensities as expected for CD markers. This indicates that a limited range of physiologically relevant expression levels can be measured using the disclosed methods.

Robustness

The staining intensities within a single specimen across a number of different runs and with different instruments remained consistent, indicating that this assay is capable of producing consistent and reliable staining result (FIGS. 13A-13E, FIGS. 14A-14E). These results indicate that this assay is robust and resistant to variations in run conditions.

Example 3

CD3/CD16 Expression in Tumor Array

Three multi-tissue arrays of head/neck, colorectal, and non-small cell lung malignancies were examined to validate the assay (Pantomics, Catalog Nos. HNT1021, COC1021, and LUC1021 respectively). In addition, thirty-five total whole tissue specimens and multi-tissue array cores of hepatocellular malignancies were examined to validate the assay for this intended indication (Biomax, Catalog No. LV8012) in order to examine the applicability of the assay to these cancer types. Tissues were analyzed with the optimized conditions described in Example 2.

Head and Neck Array

Frequency distribution of CD3 and CD16 cell counts in head and neck cancer cores and representative micrographs from this array are given in FIGS. 15A-15B and FIGS. 16A-16F. Cell counts for this array are listed in Table 8.

TABLE 8

CD3/CD16 Cell Counts of Cores on Head/Neck Array HNT1021.

| | | | | Membrane | | |
|---|---|---|---|---|---|---|
| Core No. | Tissue | Diagnosis | Stage (TNM) | CD3 | CD16 | Fields |
| A01 | Normal skin | | | NA | NA | |
| A02 | Schwannoma | | | NA | NA | |
| A03 | Pleomorphic adenoma | | | NA | NA | |
| A04 | Inflammation | | | NA | NA | |
| A05 | Inflammation | | | NA | NA | |
| A06 | Pleomorphic adenoma | | | NA | NA | |
| A07 | Squamous cell carcinoma | I | T2N0M0 | 1 | 32 | 5 fields |
| A08 | Squamous cell carcinoma | I | T2N0M0 | 0 | 0 | 5 fields |
| A09 | Squamous cell carcinoma | I | T4N0M0 | 0 | 8 | 5 fields |

TABLE 8-continued

CD3/CD16 Cell Counts of Cores on Head/Neck Array HNT1021.

| Core No. | Tissue | Diagnosis | Stage (TNM) | Membrane CD3 | CD16 | Fields |
|---|---|---|---|---|---|---|
| A10 | Squamous cell carcinoma | I | T2N1M0 | 1 | 14 | 5 fields |
| A11 | Squamous cell carcinoma | I | T2N0M0 | 7 | 41 | 5 fields |
| A12 | Squamous cell carcinoma | I | T1N0M0 | 3 | 13 | 5 fields |
| A13 | Squamous cell carcinoma | I | T2N0M0 | 4 | 14 | 5 fields |
| B01 | Squamous cell carcinoma | I | T3N1M0 | 1 | 14 | 5 fields |
| B02 | Squamous cell carcinoma | I | T2N0M0 | 3 | 40 | 5 fields |
| B03 | Squamous cell carcinoma | I | T2N1M0 | 6 | 31 | 5 fields |
| B04 | Squamous cell carcinoma | I | T1N1M0 | 6 | 19 | 5 fields |
| B05 | Squamous cell carcinoma | I | T2N0M0 | 5 | 11 | 3 fields |
| B06 | Squamous cell carcinoma | I | T1N0M0 | 4 | 46 | 5 fields |
| B07 | Squamous cell carcinoma | I | T3N1M0 | 4 | 16 | 5 fields |
| B08 | Squamous cell carcinoma | I | T3N1M0 | 2 | 50 | 5 fields |
| B09 | Squamous cell carcinoma | I | T3N1M0 | 5 | 16 | 5 fields |
| B10 | Squamous cell carcinoma | I | T1N2M0 | 2 | 14 | 5 fields |
| B11 | Squamous cell carcinoma | I | T2N0M0 | 65 | 45 | 2 fields |
| B12 | Squamous cell carcinoma | I | T3N2M0 | 0 | 14 | 5 fields |
| B13 | Squamous cell carcinoma | I | T3N0M0 | 13 | 25 | 5 fields |
| C01 | Squamous cell carcinoma | I | T2N0M0 | 15 | 40 | 5 fields |
| C02 | Squamous cell carcinoma | I | T4N1M0 | 1 | 26 | 5 fields |
| C03 | Squamous cell carcinoma | I | T2N0M0 | 0 | 40 | 5 fields |
| C04 | Squamous cell carcinoma | I | T3N0M0 | 66 | 68 | 5 fields |
| C05 | Squamous cell carcinoma | I | T1N0M0 | 44 | 46 | 5 fields |
| C06 | Squamous cell carcinoma | I | T3N1M0 | 8 | 18 | 5 fields |
| C07 | Squamous cell carcinoma | I | T2N2M0 | 0 | 35 | 5 fields |
| C08 | Squamous cell carcinoma | I | T2N0M0 | 0 | 7 | 5 fields |
| C09 | Squamous cell carcinoma | I | T3N0M0 | 15 | 50 | 5 fields |
| C10 | Squamous cell carcinoma | I | T2N0M0 | 8 | 21 | 5 fields |
| C11 | Squamous cell carcinoma | I | T4N2M0 | 17 | 48 | 5 fields |
| C12 | Squamous cell carcinoma | I~II | T2N1M0 | 2 | 13 | 5 fields |
| C13 | Squamous cell carcinoma | I~II | T2N1M0 | 9 | 7 | 5 fields |
| D01 | Squamous cell carcinoma | I~II | T2N0M0 | 4 | 12 | 5 fields |
| D02 | Squamous cell carcinoma | I~II | T2N1M0 | 30 | 59 | 5 fields |
| D03 | Squamous cell carcinoma | I~II | T1N0M0 | 23 | 53 | 4 fields |
| D04 | Squamous cell carcinoma | I~II | T2N1M0 | 1 | 21 | 5 fields |
| D05 | Squamous cell carcinoma | I~II | T2N0M0 | 3 | 45 | 5 fields |
| D06 | Squamous cell carcinoma | I~II | T3N0M0 | 10 | 60 | 5 fields |
| D07 | Squamous cell carcinoma | I~II | T3N1M0 | 2 | 26 | 5 fields |
| D08 | Squamous cell carcinoma | I~II | T3N1M0 | 0 | 20 | 5 fields |
| D09 | Squamous cell carcinoma | II | T3N0M0 | 0 | 5 | 5 fields |
| D10 | Squamous cell carcinoma | II | T2N1M0 | 2 | 30 | 5 fields |
| D11 | Squamous cell carcinoma | II | T2N0M0 | 31 | 45 | 5 fields |
| D12 | Squamous cell carcinoma | II | T3N1M0 | 1 | 39 | 5 fields |
| D13 | Squamous cell carcinoma | II | T2N1M0 | 4 | 8 | 5 fields |
| E01 | Squamous cell carcinoma | II | T2N1M0 | 0 | 11 | 5 fields |
| E02 | Squamous cell carcinoma | II | T2N0M0 | 14 | 18 | 5 fields |
| E03 | Squamous cell carcinoma | II | T3N2M0 | 9 | 43 | 5 fields |
| E04 | Squamous cell carcinoma | II | T2N0M0 | 7 | 53 | 5 fields |
| E05 | Squamous cell carcinoma | II | T3N0M0 | 0 | 11 | 5 fields |
| E06 | Squamous cell carcinoma | II | T3N0M0 | 0 | 6 | 5 fields |
| E07 | Squamous cell carcinoma | II | T4N0M0 | 14 | 39 | 5 fields |
| E08 | Squamous cell carcinoma | II | T2N0M0 | 1 | 19 | 5 fields |
| E09 | Squamous cell carcinoma | II | T1N0M0 | 1 | 21 | 5 fields |
| E10 | Squamous cell carcinoma | II | T3N0M0 | 9 | 19 | 5 fields |
| E11 | Squamous cell carcinoma | II | T4N2M0 | 2 | 6 | 5 fields |
| E12 | Squamous cell carcinoma | II | T1N2M0 | 7 | 22 | 5 fields |
| E13 | Squamous cell carcinoma | II | T3N0M0 | 3 | 31 | 5 fields |
| F01 | Squamous cell carcinoma | II~III | T3N1M0 | 23 | 34 | 5 fields |
| F02 | Squamous cell carcinoma | II~III | T2N1M0 | 2 | 37 | 5 fields |
| F03 | Squamous cell carcinoma | II~III | T2N1M0 | 2 | 21 | 5 fields |
| F04 | Squamous cell carcinoma | II~III | T1N1M0 | 0 | 26 | 5 fields |
| F05 | Squamous cell carcinoma | II~III | T3N0M0 | 0 | 22 | 5 fields |
| F06 | Squamous cell carcinoma | II~III | T4N0M0 | 20 | 46 | 5 fields |
| F07 | Squamous cell carcinoma | II~III | T4N1M0 | 16 | 51 | 5 fields |
| F08 | Squamous cell carcinoma | II~III | T3N1M0 | 6 | 30 | 5 fields |
| F09 | Squamous cell carcinoma | III | T1N1M0 | 0 | 29 | 5 fields |
| F10 | Squamous cell carcinoma | III | T2N2M0 | 8 | 81 | 5 fields |
| F11 | Squamous cell carcinoma | III | T2N0M0 | 0 | 2 | 5 fields |
| F12 | Squamous cell carcinoma | III | T2N1M0 | 4 | 36 | 5 fields |
| F13 | Squamous cell carcinoma | III | T2N2M0 | 40 | 71 | 5 fields |
| G01 | Squamous cell carcinoma | III | T1N1M0 | 38 | 37 | 5 fields |
| G02 | Squamous cell carcinoma | III | T2N0M0 | 0 | 18 | 5 fields |

Colorectal Cancer Array

Frequency distribution of CD3 and CD16 cell counts in colorectal cancer cores and representative micrographs from this array are given in FIGS. 17A-17B and FIGS. 18A-18F. Cell counts for this array are listed in Table 9.

TABLE 9

CD3/CD16 Cell Counts of Cores on Colorectal Array COC1021.

| Core No. | Tissue | Diagnosis | Stage (TNM) | Membrane CD3 | CD16 | Fields |
|---|---|---|---|---|---|---|
| A01 | Normal | | | NA | NA | |
| A02 | Normal | | | NA | NA | |
| A03 | Congenital megacolon | | | NA | NA | |
| A04 | Adenoma | | | NA | NA | |
| A05 | Tubular adenoma | | | NA | NA | |
| A06 | Papillary adenocarcinoma | | T3N1M0 | 14 | 2 | entire tumor |
| A07 | Mucinous adenocarcinoma | | T2N0M0 | 4 | 19 | entire tumor |
| A08 | Papillary adenocarcinoma | | T3N0M0 | 18 | 16 | entire tumor |
| A09 | Papillary adenocarcinoma | | T3N0M0 | 42 | 13 | entire tumor |
| A10 | Mucinous adenocarcinoma | | T2N0M0 | 5 | 9 | entire tumor |
| A11 | Mucinous adenocarcinoma | | T3N0M0 | 6 | 5 | entire tumor |
| A12 | Mucinous adenocarcinoma | | T3N1M0 | 1 | 21 | entire tumor |
| A13 | Mucinous adenocarcinoma | | T3N0M0 | 4 | 5 | entire tumor |
| B01 | Mucinous adenocarcinoma | | T3N1M0 | 35 | 21 | 5 fields |
| B02 | Mucinous adenocarcinoma | | T2N0M0 | 3 | 1 | entire tumor |
| B03 | Mucinous adenocarcinoma | | T3N1M0 | 1 | 9 | 4 fields |
| B04 | Adenocarcinoma | I | T3N0M0 | 31 | 15 | 5 fields |
| B05 | Adenocarcinoma | I | T3N0M0 | 16 | 31 | 5 fields |
| B06 | Adenocarcinoma | I | T2N0M0 | 17 | 7 | 5 fields |
| B07 | Adenocarcinoma | I | T3N1M0 | 25 | 26 | 3 fields |
| B08 | Adenocarcinoma | I~II | T3N0M0 | 6 | 29 | 4 fields |
| B09 | Adenocarcinoma | I~II | T3N1M0 | 9 | 40 | 5 fields |
| B10 | Adenocarcinoma | II | T2N0M0 | 33 | 26 | 5 fields |
| B11 | Adenocarcinoma | I~II | T3N0M0 | 47 | 36 | 5 fields |
| B12 | Adenocarcinoma | I~II | T3N0M0 | 20 | 11 | 5 fields |
| B13 | Adenocarcinoma | I~II | T3N0M0 | 21 | 17 | 5 fields |
| C01 | Adenocarcinoma | I~II | T2N0M0 | 2 | 12 | 5 fields |
| C02 | Adenocarcinoma | I~II | T3N1M0 | 2 | 13 | 5 fields |
| C03 | Adenocarcinoma | I~II | T3N0M0 | 17 | 7 | 5 fields |
| C04 | Adenocarcinoma | I~II | T2N0M0 | 18 | 11 | 5 fields |
| C05 | Adenocarcinoma | I~II | T4N0M0 | 4 | 11 | entire tumor |
| C06 | Adenocarcinoma | I~II | T3N0M0 | 13 | 12 | 5 fields |
| C07 | Adenocarcinoma | I~II | T3N0M0 | 7 | 32 | 5 fields |
| C08 | Adenocarcinoma | I~II | T3N1M0 | 10 | 20 | 5 fields |
| C09 | Adenocarcinoma | I~II | T2N0M0 | 39 | 28 | 5 fields |
| C10 | Adenocarcinoma | I~II | T3N0M0 | 11 | 24 | 5 fields |
| C11 | Adenocarcinoma | I~II | T3N0M0 | 14 | 21 | 5 fields |
| C12 | Adenocarcinoma | I~II | T2N0M0 | 6 | 10 | 5 fields |
| C13 | Adenocarcinoma | I~II | T3N0M0 | 11 | 15 | 5 fields |
| D01 | Adenocarcinoma | I~II | T3N1M0 | 2 | 3 | 5 fields |
| D02 | Adenocarcinoma | I~II | T3N0M0 | 55 | 27 | 5 fields |
| D03 | Adenocarcinoma | I~II | T3N0M0 | 53 | 52 | 5 fields |
| D04 | Adenocarcinoma | I~II | T2N0M0 | 64 | 45 | 5 fields |
| D05 | Adenocarcinoma | I~II | T3N0M0 | 9 | 8 | 5 fields |
| D06 | Adenocarcinoma | I~II | T2N0M0 | 67 | 22 | 5 fields |
| D07 | Adenocarcinoma | I~II | T1N0M0 | 31 | 28 | 5 fields |
| D08 | Adenocarcinoma | I~II | T2N0M0 | 9 | 10 | 5 fields |
| D09 | Adenocarcinoma | I~II | T3N1M0 | 14 | 13 | 5 fields |
| D10 | Adenocarcinoma | II | T3N0M0 | 12 | 18 | 5 fields |
| D11 | Adenocarcinoma | II | T2N0M0 | 7 | 22 | 5 fields |
| D12 | Adenocarcinoma | II | T2N1M0 | 22 | 15 | 5 fields |
| D13 | Adenocarcinoma | II | T2N0M0 | 27 | 25 | 5 fields |
| E01 | Adenocarcinoma | II | T2N0M0 | 22 | 17 | 5 fields |
| E02 | Adenocarcinoma | II | T2N0M0 | 13 | 18 | 5 fields |
| E03 | Adenocarcinoma | II | T3N0M0 | 9 | 10 | 5 fields |
| E04 | Adenocarcinoma | II | T3N0M0 | 1 | 7 | entire tumor |
| E05 | Adenocarcinoma | II | T3N1M0 | 6 | 14 | 5 fields |
| E06 | Adenocarcinoma | II | T2N0M0 | 3 | 8 | 5 fields |
| E07 | Adenocarcinoma | II | T2N0M0 | 8 | 7 | 5 fields |
| E08 | Adenocarcinoma | II | T3N0M0 | 9 | 25 | 5 fields |
| E09 | Adenocarcinoma | II | T2N0M0 | 15 | 31 | 5 fields |
| E10 | Adenocarcinoma | II | T3N1M0 | 15 | 15 | 5 fields |
| E11 | Adenocarcinoma | II | T3N1M0 | 8 | 14 | 5 fields |
| E12 | Adenocarcinoma | II | T3N1M0 | 22 | 11 | 5 fields |
| E13 | Adenocarcinoma | II | T3N0M0 | 7 | 13 | 5 fields |
| F01 | Adenocarcinoma | II | T3N0M0 | 5 | 11 | 5 fields |
| F02 | Adenocarcinoma | II | T3N1M0 | 14 | 20 | 5 fields |

TABLE 9-continued

CD3/CD16 Cell Counts of Cores on Colorectal Array COC1021.

| Core No. | Tissue | Diagnosis | Stage (TNM) | Membrane CD3 | CD16 | Fields |
|---|---|---|---|---|---|---|
| F03 | Adenocarcinoma | II | T3N0M0 | 25 | 46 | 5 fields |
| F04 | Adenocarcinoma | II | T3N0M0 | 24 | 9 | 5 fields |
| F05 | Adenocarcinoma | II | T3N1M0 | 48 | 22 | 5 fields |
| F06 | Adenocarcinoma | II | T3N0M0 | 10 | 26 | 5 fields |
| F07 | Adenocarcinoma | II | T3N1M0 | 4 | 13 | 5 fields |
| F08 | Adenocarcinoma | II | T3N1M0 | 12 | 2 | 5 fields |
| F09 | Adenocarcinoma | II | T2N0M0 | 0 | 0 | entire tumor |
| F10 | Adenocarcinoma | II | T3N1M0 | 34 | 28 | 5 fields |
| F11 | Adenocarcinoma | II | T3N0M0 | 14 | 6 | 5 fields |
| F12 | Adenocarcinoma | II | T3N1M0 | 0 | 5 | 5 fields |
| F13 | Adenocarcinoma | II | T3N0M0 | 6 | 10 | 5 fields |
| G01 | Adenocarcinoma | II | T3N0M0 | 45 | 27 | 5 fields |
| G02 | Adenocarcinoma | II | T3N1M0 | 11 | 8 | 5 fields |

Non-Small Cell Lung Cancer Array

Frequency distribution of CD3 and CD16 cell counts in non-small cell lung cancer cores and representative micrographs from this array are given in FIGS. 19A-19B and FIGS. 20A-20F. Cell counts for this array are listed in Table 10.

TABLE 70

CD3/CD16 Cell Counts of Cores on Lung Array LUC1021.

| Core No. | Tissue | Diagnosis | Stage (TNM) | Membrane CD3 | CD16 | Fields |
|---|---|---|---|---|---|---|
| A01 | Normal | | | NA | NA | |
| A02 | Normal | | | NA | NA | |
| A03 | Normal | | | NA | NA | |
| A04 | Tuberculosis, TB granuloma | | | NA | NA | |
| A05 | Tuberculosis, TB granuloma | | | NA | NA | |
| A06 | Papillary adenocarcinoma | | T4N0M0 | 10 | 35 | 5 fields |
| A07 | Clear cell carcinoma | | T2N0M0 | 0 | 10 | 5 fields |
| A08 | Carcinoid | | T2N0M0 | 0 | 8 | 5 fields |
| A09 | Adenocarcinoma | III | T3N1M0 | NA | NA | No tumor |
| A10 | Small cell carcinoma | | T2N0M0 | 4 | 16 | 5 fields |
| A11 | Small cell carcinoma | | T2N0M0 | 6 | 17 | 5 fields |
| A12 | Small cell carcinoma | | T3N1M0 | 0 | 5 | 5 fields |
| A13 | Bronchioloalveolar carcinoma | | T2N1M0 | 30 | 42 | 5 fields |
| B01 | Bronchioloalveolar carcinoma | | T2N1M0 | 6 | 18 | 5 fields |
| B02 | Bronchioloalveolar carcinoma | | T2N0M0 | 17 | 42 | 5 fields |
| B03 | Bronchioloalveolar carcinoma | | T4N0M0 | 76 | 52 | 5 fields |
| B04 | Bronchioloalveolar carcinoma | | T3N0M0 | 11 | 46 | 5 fields |
| B05 | Bronchioloalveolar carcinoma | | T2N0M0 | 16 | 1 | 5 fields |
| B06 | Adenocarcinoma | II | T2N0M0 | 24 | 48 | 5 fields |
| B07 | Bronchioloalveolar carcinoma | | T2N0M0 | 3 | 16 | 5 fields |
| B08 | Bronchioloalveolar carcinoma | | T3N1M0 | 25 | 31 | 5 fields |
| B09 | Bronchioloalveolar carcinoma | | T2N1M0 | 0 | 6 | 5 fields |
| B10 | Bronchioloalveolar carcinoma | | T3N0M0 | 15 | 36 | 5 fields |
| B11 | Adenocarcinoma | II | T2N1M0 | 10 | 11 | 5 fields |
| B12 | Adenocarcinoma | II | T2N1M0 | 4 | 26 | 5 fields |
| B13 | Adenocarcinoma | II | T2N0M0 | NA | NA | Speckling and very weak staining |
| C01 | Adenocarcinoma | II | T2N1M0 | 24 | 29 | 5 fields |
| C02 | Adenocarcinoma | II | T3N1M0 | 11 | 41 | 5 fields |
| C03 | Adenocarcinoma | II | T2N2M0 | 17 | 8 | 2 fields |
| C04 | Adenocarcinoma | II | T2N0M0 | 20 | 36 | 5 fields |
| C05 | Bronchioloalveolar carcinoma | | T2N1M0 | 9 | 21 | 5 fields |
| C06 | Adenocarcinoma | II~III | T3N0M0 | 0 | 0 | 5 fields |
| C07 | Adenocarcinoma | II~III | T2N0M0 | 10 | 15 | 5 fields |
| C08 | Adenocarcinoma | II~III | T3N0M0 | 19 | 79 | 5 fields |
| C09 | Adenocarcinoma | II~III | T2N2M0 | 22 | 24 | 3 fields |
| C10 | Adenocarcinoma | III | T2N1M0 | 18 | 63 | 5 fields |
| C11 | Adenocarcinoma | III | T2N1M0 | NA | NA | Anthracotic pigment interferes with scoring |

TABLE 70-continued

CD3/CD16 Cell Counts of Cores on Lung Array LUC1021.

| Core No. | Tissue | Diagnosis | Stage (TNM) | Membrane CD3 | CD16 | Fields |
|---|---|---|---|---|---|---|
| C12 | Squamous cell carcinoma | I | T2N1M0 | 0 | 7 | 5 fields |
| C13 | Squamous cell carcinoma | I | T3N0M0 | 0 | 10 | 5 fields |
| D01 | Squamous cell carcinoma | I | T4N0M0 | 12 | 29 | 5 fields |
| D02 | Squamous cell carcinoma | I | T2N0M0 | 2 | 32 | 5 fields |
| D03 | Squamous cell carcinoma | I~II | T2N1M0 | 23 | 52 | 5 fields |
| D04 | Squamous cell carcinoma | I~II | T2N1M0 | 3 | 16 | 3 fields |
| D05 | Squamous cell carcinoma | II | T3N3M0 | 19 | 27 | 5 fields |
| D06 | Squamous cell carcinoma | I~II | T2N0M0 | 1 | 23 | 5 fields |
| D07 | Squamous cell carcinoma | I~II | T2N1M0 | 26 | 30 | 5 fields |
| D08 | Squamous cell carcinoma | II | T2N2M0 | 17 | 27 | 5 fields |
| D09 | Squamous cell carcinoma | II | T3N1M0 | 1 | 13 | 5 fields |
| D10 | Squamous cell carcinoma | II | T2N1M0 | 21 | 26 | 5 fields |
| D11 | Squamous cell carcinoma | II | T2N0M0 | 3 | 15 | 5 fields |
| D12 | Squamous cell carcinoma | II | T2N0M0 | 0 | 16 | 5 fields |
| D13 | Squamous cell carcinoma | II | T2N0M0 | 3 | 14 | 5 fields |
| E01 | Squamous cell carcinoma | II | T2N0M0 | 3 | 21 | 5 fields |
| E02 | Squamous cell carcinoma | II | T2N1M0 | 1 | 2 | 5 fields |
| E03 | Squamous cell carcinoma | II | T2N1M0 | 2 | 3 | 5 fields |
| E04 | Squamous cell carcinoma | II | T2N1M0 | 8 | 10 | 5 fields |
| E05 | Squamous cell carcinoma | II~III | T2N1M0 | 5 | 8 | 5 fields |
| E06 | Squamous cell carcinoma | II~III | T3N1M0 | 26 | 28 | 5 fields |
| E07 | Squamous cell carcinoma | II~III | T2N0M0 | 9 | 11 | 5 fields |
| E08 | Squamous cell carcinoma | II~III | T3N1M0 | 0 | 8 | 5 fields |
| E09 | Squamous cell carcinoma | II~III | T3N1M0 | 1 | 15 | 5 fields |
| E10 | Squamous cell carcinoma | II~III | T2N0M0 | 15 | 26 | 5 fields |
| E11 | Squamous cell carcinoma | II~III | T2N1M0 | 23 | 53 | 5 fields |
| E12 | Squamous cell carcinoma | II~III | T2N0M0 | 1 | 21 | 5 fields |
| E13 | Squamous cell carcinoma | III | T2N0M0 | 6 | 7 | 5 fields |
| F01 | Squamous cell carcinoma | III | T2N0M0 | 9 | 30 | 5 fields |
| F02 | Squamous cell carcinoma | III | T2N0M0 | 6 | 6 | 5 fields |
| F03 | Squamous cell carcinoma | III | T2N1M0 | 39 | 56 | 5 fields |
| F04 | Squamous cell carcinoma | III | T4N1M0 | 67 | 58 | 5 fields |
| F05 | Squamous cell carcinoma | III | T2N0M0 | 160 | 51 | 5 fields |
| F06 | Squamous cell carcinoma | III | T2N1M0 | 5 | 27 | 5 fields |
| F07 | Squamous cell carcinoma | III | T2N0M0 | 8 | 9 | 5 fields |
| F08 | Squamous cell carcinoma | III | T2N1M0 | 0 | 2 | 5 fields |
| F09 | Squamous cell carcinoma | III | T2N1M0 | 60 | 67 | 5 fields |
| F10 | Squamous cell carcinoma | III | T2N1M0 | 1 | 1 | 5 fields |
| F11 | Squamous cell carcinoma | III | T2N0M0 | 0 | 2 | 5 fields |
| F12 | Squamous cell carcinoma | III | T2N0M0 | 0 | 8 | 5 fields |
| F13 | Squamous cell carcinoma | III | T2N1M0 | 1 | 6 | 5 fields |
| G01 | Squamous cell carcinoma | III | T2N0M0 | 14 | 40 | 5 fields |
| G02 | Squamous cell carcinoma | III | T2N0M0 | 64 | 70 | 5 fields |

Hepatocellular Carcinoma (HCC) Whole Tissue Specimens and Array Cores

Figure 21A:
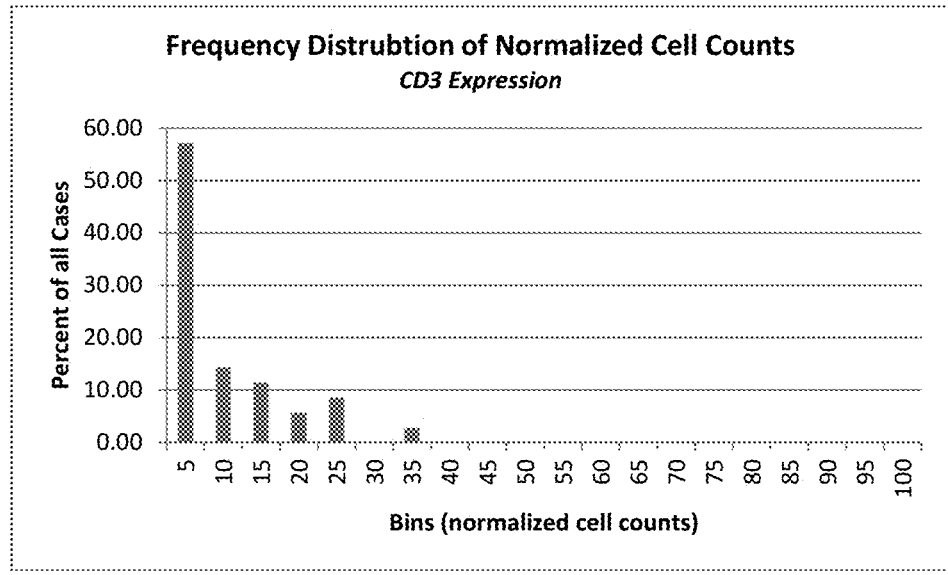
FIGS. 21A-21B are bar graphs showing the frequency distribution of (A) CD3 and (B) CD16 cell counts for HCC Specimens.
Figure 21B:
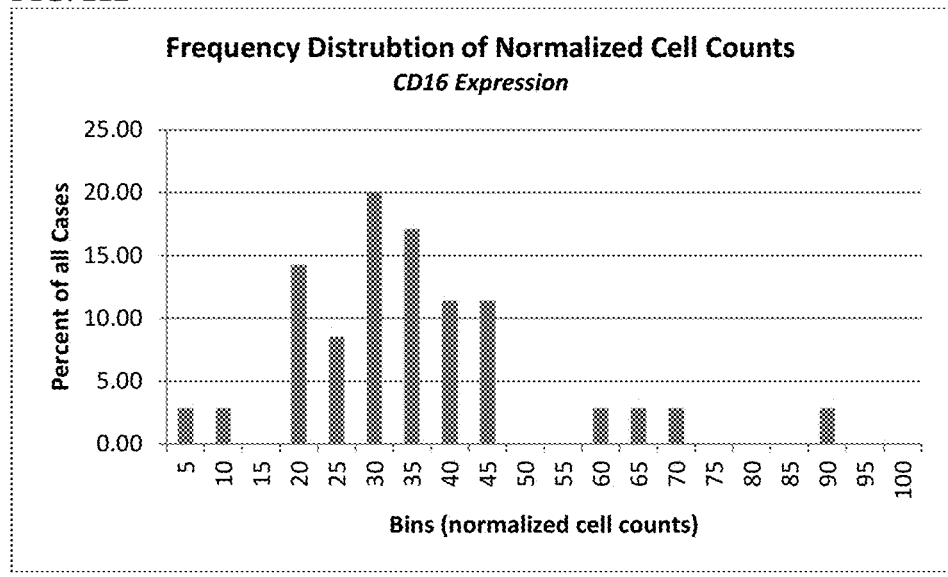

Frequency distribution of CD3 and CD16 cell counts in HCC whole tissue specimens and array cores are shown in FIGS. 21A-21B. HCC specimens showed minimal desmoplastic stroma. CD16 staining observed in the sinusoids of both normal and tumor can be attributed to Kupffer cell staining. Kupffer cell staining if present in the tumor was scored as part of the stromal staining. Representative micrographs from these specimens are shown in FIGS. 22A-F. Cell Counts for these specimens are listed in Table 11.

TABLE 11

CD3/CD16 Cell Counts of Hepatocellular Carcinoma Specimens.

| Tissue ID | Membrane CD3 | CD16 | Fields | Comments |
|---|---|---|---|---|
| 93S2460 C3 | 12 | 27 | 5 | 80% necrotic tumor |
| S96-6008 1 | 20 | 20 | 5 | |
| HCC5 | 20 | 20 | 5 | Multiple tumor nodules - only contiguous stroma adjacent to nodules was counted |
| VR-15-09-39 | 7 | 30 | 5 | |
| 1375-08 4 | 21 | 30 | 5 | |
| HCC17 | 24 | 32 | 5 | |
| VR-384-10-35 | 9 | 66 | 5 | |
| WD-11008-A | 3 | 30 | 5 | Heterogeneous CD16 expression (different morphology) |
| WD-10819-A | 14 | 45 | 5 | |
| 3112865 A2 | 4 | 33 | 5 | |
| WD-10943 | 13 | 44 | 5 | |
| LV8012 A1 | 34 | 32 | 5 | |
| LV8012 A2 | 1 | 19 | 5 | |
| LV8012 A3 | 9 | 38 | 5 | |
| LV8012 A4 | 7 | 22 | 5 | Hemosiderin pigment |
| LV8012 A5 | 0 | 32 | 5 | |
| LV8012 A6 | 0 | 27 | 5 | |
| LV8012 A7 | 0 | 10 | 5 | |
| LV8012 A8 | 2 | 43 | 5 | |
| LV8012 A9 | 9 | 21 | 5 | |
| LV8012 A10 | 2 | 37 | 5 | |

TABLE 11-continued

CD3/CD16 Cell Counts of Hepatocellular Carcinoma Specimens.

| Tissue ID | Membrane | | | |
|---|---|---|---|---|
| | CD3 | CD16 | Fields | Comments |
| LV8012 B1 | 0 | 65 | 5 | |
| LV8012 B3 | 0 | 37 | 5 | |
| LV8012 B4 | 11 | 87 | 5 | |
| LV8012 B5 | 5 | 39 | 5 | |
| LV8012 B8 | 1 | 19 | 5 | |
| LV8012 B9 | 0 | 26 | 5 | |
| LV8012 B10 | 0 | 33 | 5 | |
| LV8012 C2 | 1 | 28 | 5 | |
| LV8012 C5 | 3 | 42 | 5 | |
| LV8012 C6 | 23 | 58 | 5 | |
| LV8012 D7 | 0 | 33 | 5 | |
| LV8012 D8 | 2 | 19 | 5 | |
| LV8012 E8 | 0 | 1 | 5 | |
| LV8012 E10 | 0 | 24 | 5 | |

Example 4

Antibody Stability

Stability is the ability of an antibody to retain performance characteristics under extended periods of storage. This parameter was evaluated by preparing a dispenser containing the working dilution of the antibody. At day zero, positive control slides are stained with the dual IHC assay described in Example 2. A negative control was also stained at this time. The dispenser was placed in an incubator set at 45° C. for one week. At day seven, positive slides were stained and compared to the day zero slides by a qualified reader. A difference less than or equal to one staining intensity point is considered passing. Additionally, background staining less than or equal to 0.5 points is considered passing. A passing score here designates an expiration date of 1-year from the preparation date at 4° C. If the antibody does not pass the 1-year evaluation listed above, the experiment is repeated at 37° C. A passing score following 37° C. accelerated stability analysis designates an expiration date of 6-months from the preparation date when stored at 4° C. If necessary, real-time stability at 4° C. may be assessed.

CD3/CD16 staining showed that signal intensity was substantially maintained after 7 days at 45° C. (FIGS. 23A-23B). These results support the assignment of a 1-year expiration date to the primary antibody at the working concentration.

REFERENCES

1. DeJarnette et al., "Specific Requirement for CD3 in T Cell Development." Immunology 95 (1998): 14909-4914.
2. Dietrich et al., "Role of CD3/in T Cell Receptor Assembly." JCB 132 (1995): 299-310.
3. Bojarska-Junak et al., "Natural Killer-like T CD3+/CD16+CD56+ Cells in Chronic Lymphocytic Leukemia: Intracellular Cytokine Expression and Relationship with Clinical Outcome." Oncology Reports 24.3 (2010): 803-10.
4. Sconocchia et al., "Tumor Infiltration by FccRIII (CD16)+ Myeloid Cells Is Associated with Improved Survival in Patients with Colorectal Carcinoma." IJC 128 (2010): 2663-672.
5. Carrega et al., "Natural Killer Cells Infiltrating Human Nonsmall-cell Lung Cancer Are Enriched in CD56brightCD16− Cells and Display an Impaired Capability to Kill Tumor Cells." Cancer 112 (2008): 863-75.
6. Gerdes et al., "GA201 (RG7160): A Novel, Humanised, Glycoengineered Anti-EGFR Antibody with Enhanced ADCC and Superior in Vivo Efficacy Compared with Cetuximab." AACR Journals (2012): 1-32.
7. Lanier et al., "Functional Properties of a Unique Subset of Cytotoxic CD3+T Lymphocytes That Express Fc Receptors for IgG (CD16/LEU-11 Antigen)." The Rockefeller University Press 162 (1985): 2089-106.
8. Nimmerjahn et al., "Translating Basic Mechanisms of IgG Effector Activity." Cancer Immunity 12 (2012): 13-20.
9. Shibuya et al., "Clinical Significance of Poor CD3 Response in Head." Clinical Cancer Research 8 (2002): 745-51.
10. Galon et al., "Type, Density, and Location of Immune Cells Within Human Colorectal Tumors Predict Clinical Outcome." Science 313 (2006): 1960-964.

In view of the many possible embodiments to which the principles of the disclosure may be applied, it should be recognized that the illustrated embodiments are only examples of the disclosure and should not be taken as limiting the scope of the invention. Rather, the scope of the invention is defined by the following claims. We therefore claim as our invention all that comes within the scope and spirit of these claims.

We claim:
1. A method comprising:
contacting a colorectal tumor sample, a sample of a tumor of the head or of the neck, or a lung tumor sample with a buffer comprising Tris and a preservative, wherein the pH of the buffer is about 8-9;
contacting the sample with a first primary antibody, wherein the first primary antibody is immunoreactive with either human CD3 protein or human CD16 protein;
contacting the sample with a first secondary antibody having a first label conjugated thereto, wherein the first secondary antibody is immunoreactive with the first primary antibody;
contacting the sample with a set of reagents reactive with the first secondary antibody to generate a first detectable signal in proximity to the first epitope in the sample;
denaturing the sample by incubating the sample at 80° C.-100° C. for at least 5 minutes;
contacting the sample with a blocking antibody;
contacting the sample with the buffer;
contacting the sample with a second primary antibody, wherein the second primary antibody is immunoreactive with the other of human CD3 or human CD16, and further wherein the first primary antibody and the second primary antibody are from the same host species;
contacting the sample with a second secondary antibody having a second label conjugated thereto, wherein the second labeled secondary antibody is immunoreactive with the second primary antibody; and
contacting the sample with a set of reagents reactive with the second label to generate a second detectable signal in proximity to the second epitope in the sample, wherein the first detectable signal and the second detectable signal are different.
2. The method of claim 1, wherein the sample is contacted with the buffer for at least 30 minutes prior to contacting the sample with the first primary antibody.

3. The method of claim 1, wherein the sample is contacted with the buffer for 40 minutes prior to contacting the sample with the first primary antibody.

4. The method of claim 1, wherein the sample is contacted with the first primary antibody for at least 5 minutes at 37° C.

5. The method of claim 1, wherein the sample is contacted with the first primary antibody for 8 minutes at 37° C.

6. The method of claim 1, wherein the denaturing the sample comprises incubating the sample at 95° C. for at least 8 minutes.

7. The method of claim 1, wherein the blocking antibody comprises an antibody reactive with the host species of the first primary antibody.

8. The method of claim 1, wherein the method further comprises contacting the sample with a reaction buffer comprising Tris for at least 20 minutes to remove residual blocking antibody.

9. The method of claim 1, wherein:
the first label comprises a hapten, and the set of reagents reactive with the first label comprises: a tertiary antibody conjugated to a first enzyme, wherein the tertiary antibody is immunoreactive with the hapten, and one or more reagents that produce a first detectable reaction product in the presence of the enzyme, wherein the detectable reaction product generates the first detectable signal; and
the second label comprises a second enzyme, and the set of reagents reactive with the second label comprises one or more reagents that produce a second detectable reaction product in the presence of the second enzyme, wherein the second detectable reaction product generates the second detectable signal.

10. The method of claim 1, wherein:
the first label comprises a first enzyme, and the set of reagents reactive with the first label comprises one or more reagents that produce a first detectable reaction product in the presence of the first enzyme, wherein the second detectable reaction product generates the second detectable signal; and
the second label comprises a hapten, and the set of reagents reactive with the second label comprises: a tertiary antibody conjugated to a second enzyme, wherein the tertiary antibody is immunoreactive with the hapten, and one or more reagents that produce a second detectable reaction product in the presence of the enzyme, wherein the detectable reaction product generates the second detectable signal.

11. The method of claim 1, wherein the sample is a formalin fixed, paraffin embedded (FFPE) sample.

12. The method of claim 1, wherein the tumor sample is selected from the group consisting of a non-small cell lung cancer sample, a head and neck cancer sample, and a colorectal cancer sample.

13. The method of claim 1, wherein:
the first primary antibody is an anti-human CD3 monoclonal antibody, and the second primary antibody is an anti-human CD16 monoclonal antibody; or
the first primary antibody is an anti-human CD16 monoclonal antibody, and the second primary antibody is an anti-human CD3 monoclonal antibody.

14. The method of claim 13, wherein:
the label of the secondary antibody that is immunoreactive with the anti-CD3 monoclonal antibody comprises a hapten selected from the group consisting of fluorescein, dinitrophenyl, biotin, and 3-hydroxyquinoxaline-2-carboxylic acid (HQ), and the set of reagents reactive with the label of the secondary antibody immunoreactive with the anti-CD3 monoclonal antibody comprises:
a tertiary antibody comprising a detectable label, wherein the tertiary antibody is immunoreactive with the hapten;
the label of the secondary antibody that is immunoreactive with the anti-CD16 monoclonal antibody comprises an alkaline phosphatase (AP) multimer, and the set of reagents reactive with the label of the secondary antibody that is immunoreactive with the anti-CD16 monoclonal antibody comprises: napthol, an alkaline phosphatase enhancer, and fast red.

15. The method of claim 13, wherein the CD3 antibody and the CD16 antibody are from the same host species, the host species being a mouse or a rabbit.

16. The method of claim 13, further comprising scoring the presence of CD3 protein and CD16 protein.

17. The method of claim 16, wherein scoring the presence of CD3 protein and CD16 protein comprises:
a) determining an absolute number of cells staining with the CD3 antibody in the sample using a 5×5 ocular grid with an area of 0.25 square millimeter, determining an absolute number of cells staining with the CD16 antibody in the sample using a 5×5 ocular grid with an area of 0.25 square millimeter, extrapolating the absolute number of cells staining with the CD3 antibody to a number of cells in a 1 square millimeter region, and extrapolating the absolute number of cells staining with the CD16 antibody to a number of cells in a 1 square millimeter region, thereby generating a score of CD3 protein and CD16 protein; or
b) determining the area of staining with the CD3 antibody within the intratumoral and contiguous peri-tumoral stroma of the sample, determining the area of staining with the CD16 antibody within the intratumoral and contiguous peri-tumoral stroma of the sample, dividing the area of staining with the CD3 antibody in the intratumoral and contiguous peri-tumoral stroma by the area of total stroma, thereby generating a score of CD3 protein for the stroma, and dividing the area of staining with the CD16 antibody in the intratumoral and contiguous peri-tumoral stroma by the area of total stroma, thereby generating a score of CD3 protein for the stroma; or
c) a combination of a and b.

18. The method of claim 17, wherein 1 to 15 randomly selected regions of the sample containing the tumor are selected for scoring.

19. The method of claim 17, wherein the region of the tumor consists of tumor cells only, stroma only or tumor and stroma.

20. The method of claim 16, wherein the method further comprises producing an output of the number of CD3 cells and CD16 cells.

21. The method of claim 17, wherein one or more of the steps are performed by a suitably programmed computer.

22. The method of claim 16, wherein the method is a method of determining the likelihood that the tumor will respond to an anti-EGFR targeted therapeutic agent, and the method further comprises:
determining that the tumor will respond to the anti-EGFR targeted therapeutic agent if the sample has an increased CD3 and/or CD16 score relative to a normal sample, or determining that the tumor will not respond to the anti-EGFR targeted therapeutic agent if the sample has a similar or decreased CD3 and/or CD16 score relative to a normal sample.

23. The method of claim 22, wherein the anti-EGFR targeted therapeutic agent comprises GA201.

24. The method of claim 16, wherein the sample comprises a tumor sample and the method is a method of determining whether the tumor responded to an anti-EGFR targeted therapeutic agent, and the method further comprises determining that the tumor responded to the anti-EGFR targeted therapeutic agent if the sample has an increased CD3 and/or CD16 score relative to a normal sample, or determining that the tumor did not respond to the anti-EGFR targeted therapeutic agent if the sample has a similar or decreased CD3 and/or CD16 score relative to a normal sample.

25. The method of claim 24, wherein the anti-EGFR targeted therapeutic agent comprises GA201.

* * * * *